(12) United States Patent
Noel et al.

(10) Patent No.: US 9,783,615 B2
(45) Date of Patent: Oct. 10, 2017

(54) COMBINATION TREATMENT OF CANCER

(71) Applicant: UNIVERSITÉ DE LIÈGE, Angleur (BE)

(72) Inventors: Agnès Noel, Liège (BE); Nor Eddine Sounni, Liège (BE); Alexandra Paye, Liège (BE)

(73) Assignee: UNIVERSITE DE LIEGE, Angleur (BE)

( * ) Notice: Subject to any disclaimer, the term of this patent is extended or adjusted under 35 U.S.C. 154(b) by 0 days.

(21) Appl. No.: 14/425,158

(22) PCT Filed: Sep. 2, 2013

(86) PCT No.: PCT/EP2013/068120
§ 371 (c)(1),
(2) Date: Mar. 2, 2015

(87) PCT Pub. No.: WO2014/037316
PCT Pub. Date: Mar. 13, 2014

(65) Prior Publication Data
US 2015/0232572 A1 Aug. 20, 2015

(30) Foreign Application Priority Data
Sep. 7, 2012 (EP) .................................. 12183618

(51) Int. Cl.
| | | |
|---|---|---|
| *C07K 16/18* | (2006.01) | |
| *C07K 16/40* | (2006.01) | |
| *A61K 39/395* | (2006.01) | |
| *A61K 31/517* | (2006.01) | |
| *A61K 31/381* | (2006.01) | |
| *G01N 33/574* | (2006.01) | |

(52) U.S. Cl.
CPC ............ *C07K 16/40* (2013.01); *A61K 31/381* (2013.01); *A61K 31/517* (2013.01); *A61K 39/39558* (2013.01); *G01N 33/57484* (2013.01); *C07K 2317/622* (2013.01); *C07K 2317/76* (2013.01); *G01N 2333/71* (2013.01); *G01N 2333/912* (2013.01); *G01N 2333/96486* (2013.01)

(58) Field of Classification Search
CPC .... C07K 16/18; C07K 16/40; C07K 2317/50; C07K 2317/515; C07K 2317/622; A61K 39/395; A61K 39/39533; A61K 39/3955; A61K 2039/505
See application file for complete search history.

(56) References Cited

U.S. PATENT DOCUMENTS

2006/0177448 A1   8/2006  Carey et al.
2015/0232572 A1   8/2015  Noel et al.

FOREIGN PATENT DOCUMENTS

EP   2892925 A1    7/2015
WO   2014037316 A1  3/2014

OTHER PUBLICATIONS

Durkin, A.J., et al., Journal of Surgical Research, 135: 195-201, 2006.*
Wang, Y. et al., The Journal of Biological Chemistry, 274(46): 33043-33049, 1999.*
Dong, J., et al., Proc. Natl. Acad. Sci. USA, 96: 6235-6240, 1999.*
Chabottaux, V., et. al. Membrane-Type 4 Matrix Metalloproteinase Promotes Breast Cancer Growth and Metastases. Cancer Res., 66(10):5165-5172 (2006).
Devy, L., et. al. Selective Inhibition of Matrix Metalloproteinase-14 Blocks Tumor Growth, Invasion, and Angiogenesis. Cancer Res., 69(4):1517-1526, Feb. 15, 2009.
Flynn, J. F., et. al. Anti-EGFR Therapy: Mechanism arid Advances in Clinical Efficacy in Breast Cancer. Journal of Oncology, 2009:16 pages.
Host, L., et. al. The Proteolytic Activity of MT4-MMP is Required for its Pro-Angiogenic and Pro-Metastatic Promoting Effects. International Journal of Cancer, 131:1537-1548, 2012.
International Preliminary Report on Patentability issued in PCTIEP2013/068120, dated Mar. 19, 2015, 9 pages.
International Search Report and Written Opinion issued in PCT/EP2013/068120, dated Nov. 20, 2013, 14 pages.
Seshacharyulu, P., et. al. Targeting the EGFR Signaling Pathway in Cancer Therapy. Expert Opin. Ther. Targets, 16(1):15-31, Jan. 2012.
Winding, B., et. al. Synthetic Matrix Metalloproteinase Inhibitors Inhibit Growth of Established Breast Cancer Osteolytic Lesions and Prolong Survival in Mice. Clinical Cancer Research, 8:1932-1939, Jun. 2002.

* cited by examiner

*Primary Examiner* — Misook Yu
*Assistant Examiner* — Anne Holleran
(74) *Attorney, Agent, or Firm* — Barnes & Thornburg LLP

(57) ABSTRACT

The present invention provides MT4-MMP inhibitor and EGFR inhibitor for use in the treatment of cancer, wherein said MT4-MMP inhibitor and EGFR inhibitor are different from each other. MT4-MMP (MMP-17) is a glycosylphosphatidyl inositol (GPI) anchored MMP produced by cancer cells that promotes tumor vascularization and metastases. The present invention found that MT4-MMP expression promotes cancer cell proliferation. These effects involve retinoblastoma protein (Rb) inactivation, cyclin dependent kinase CDK4 activation and Epidermal Growth Factor Receptor (EGFR) signaling. Co-immuno-precipitations indicate the existence of protein complexes harboring MT4-MMP and EGFR. The present invention further found a novel mechanism of MT4-MMP action through an outside-in signaling involving EGFR. An unexpected crosstalk between an MMP and EGFR was identified and recognized as a key driver of cancer cell biology.

5 Claims, 30 Drawing Sheets

A

B

Figure 1:
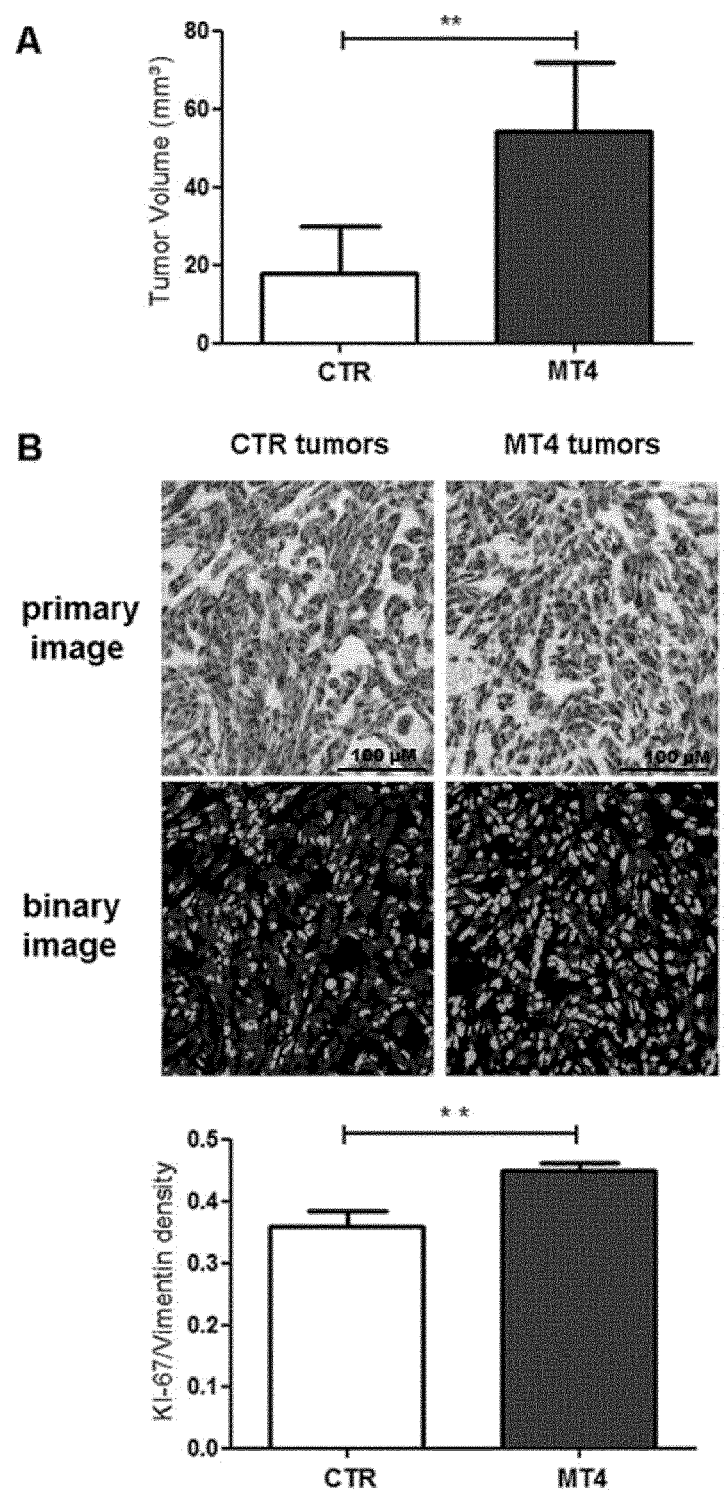
Figure 2A:
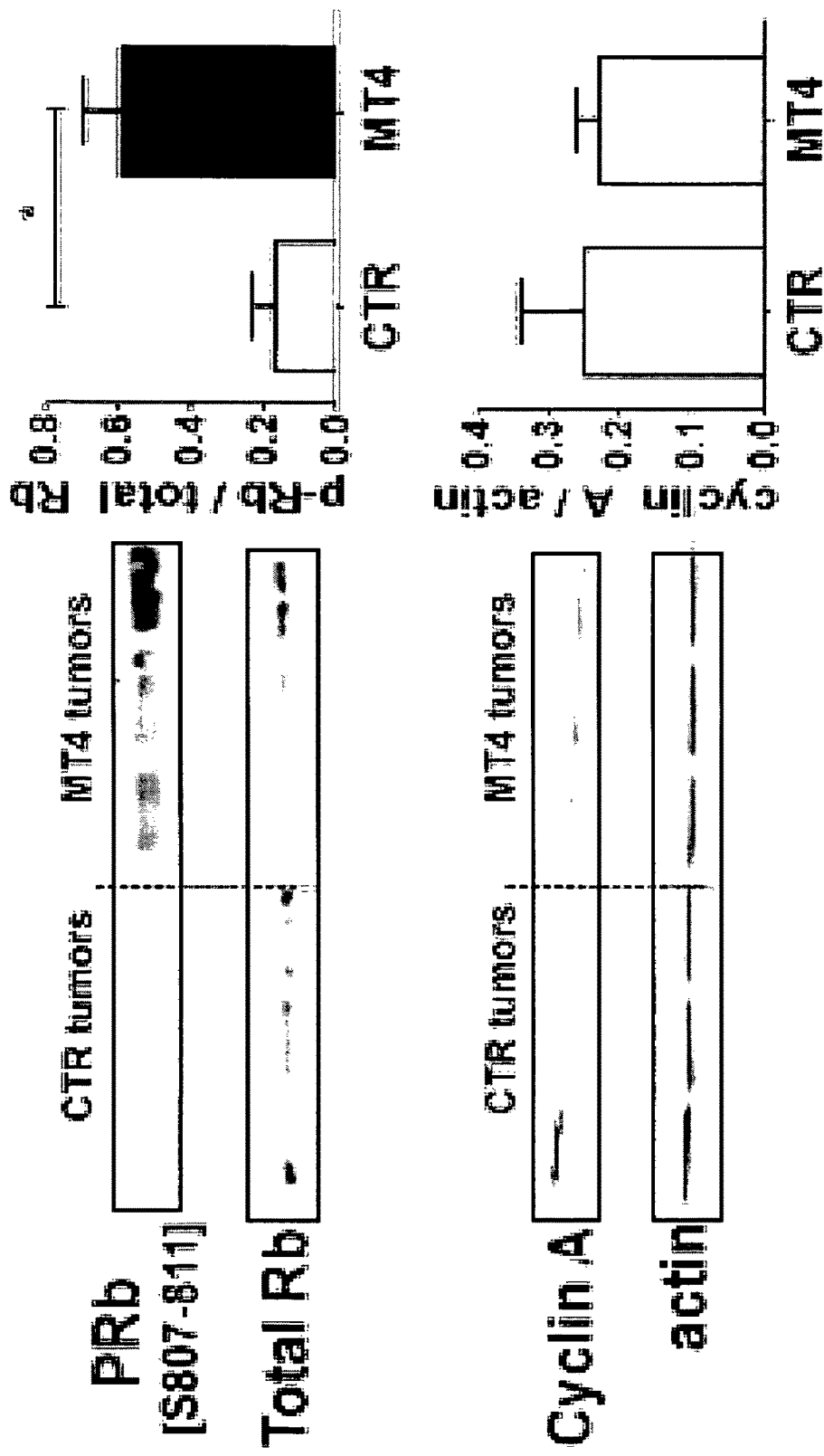
Figure 2B:
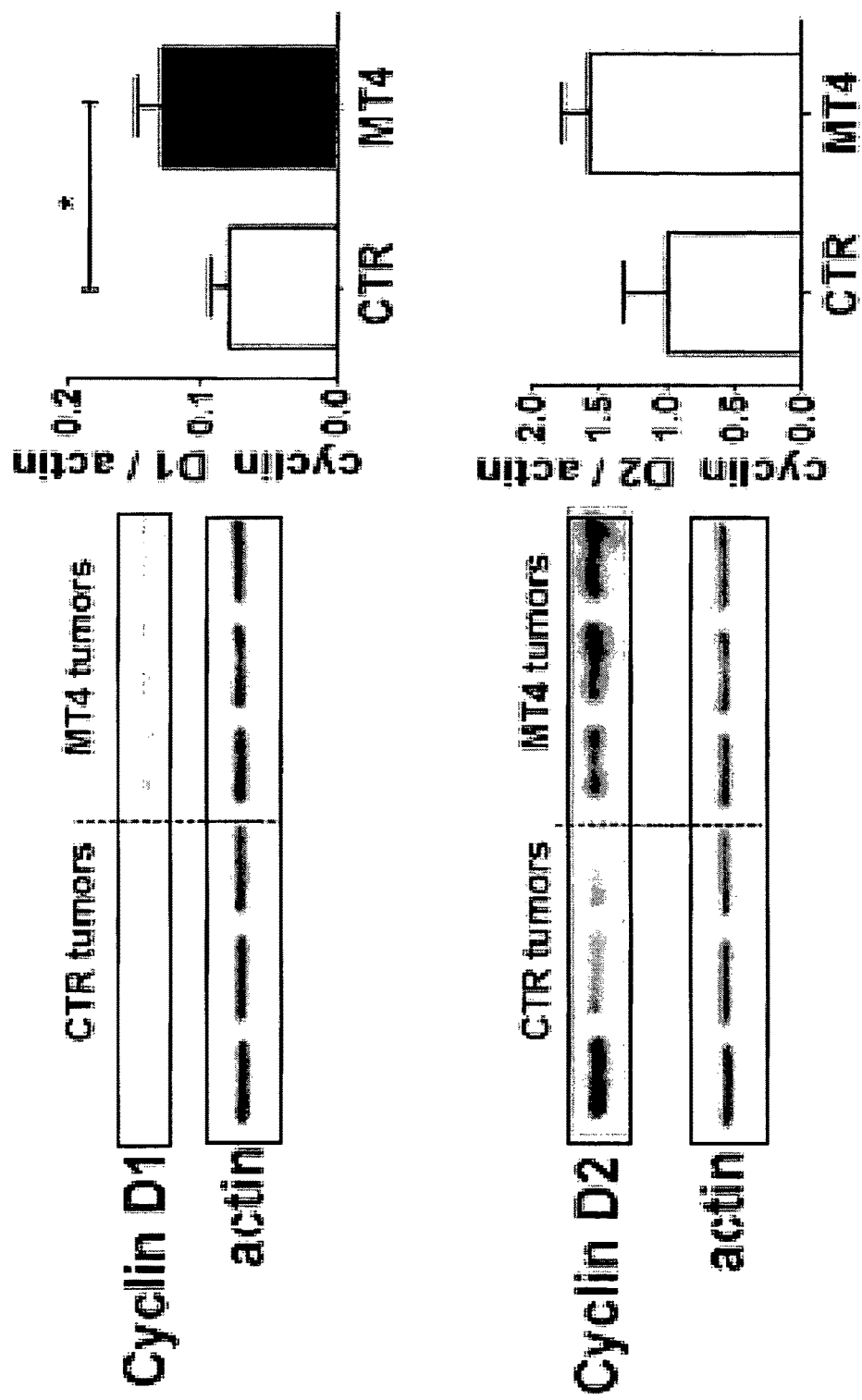
Figure 2C:
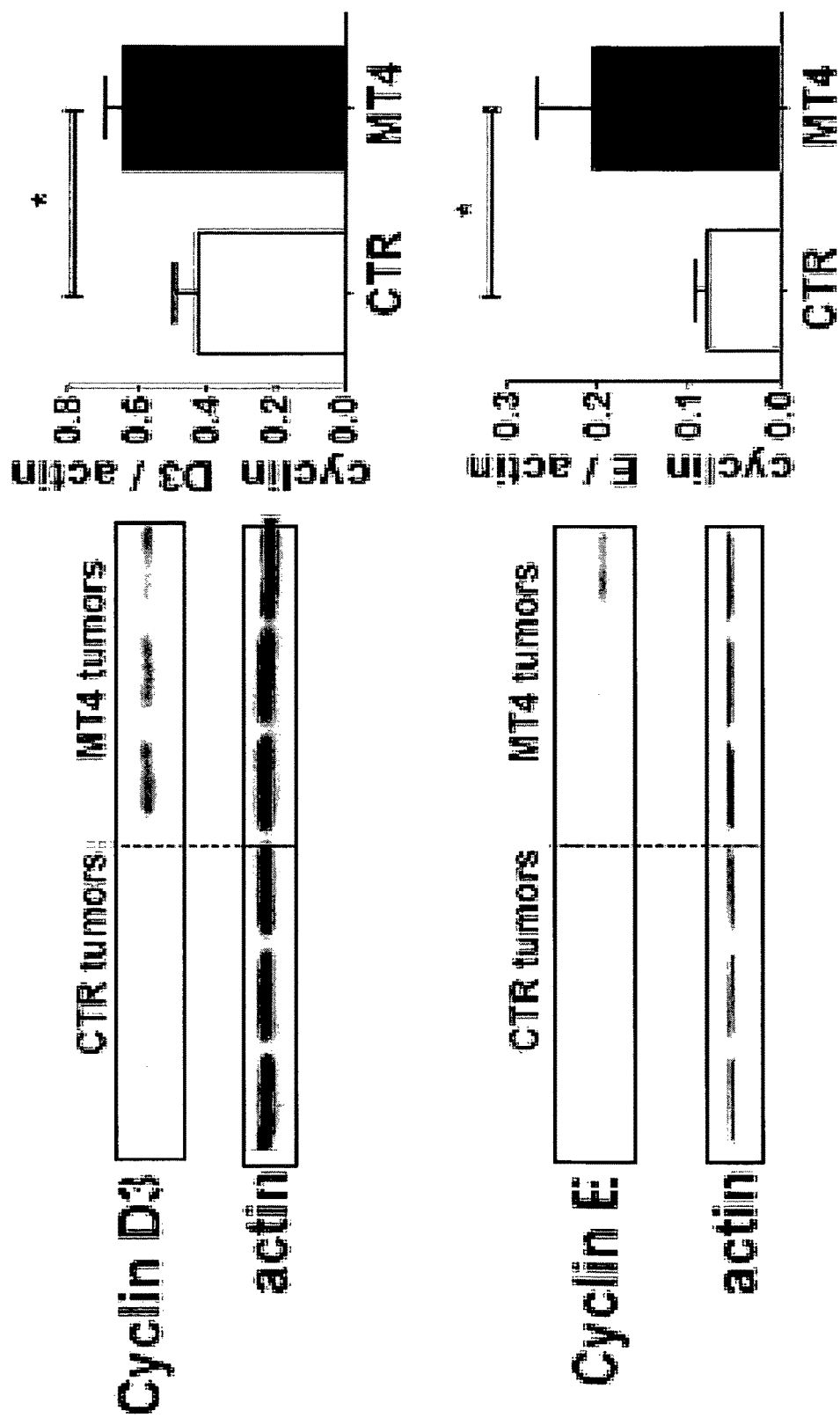
Figure 2D:
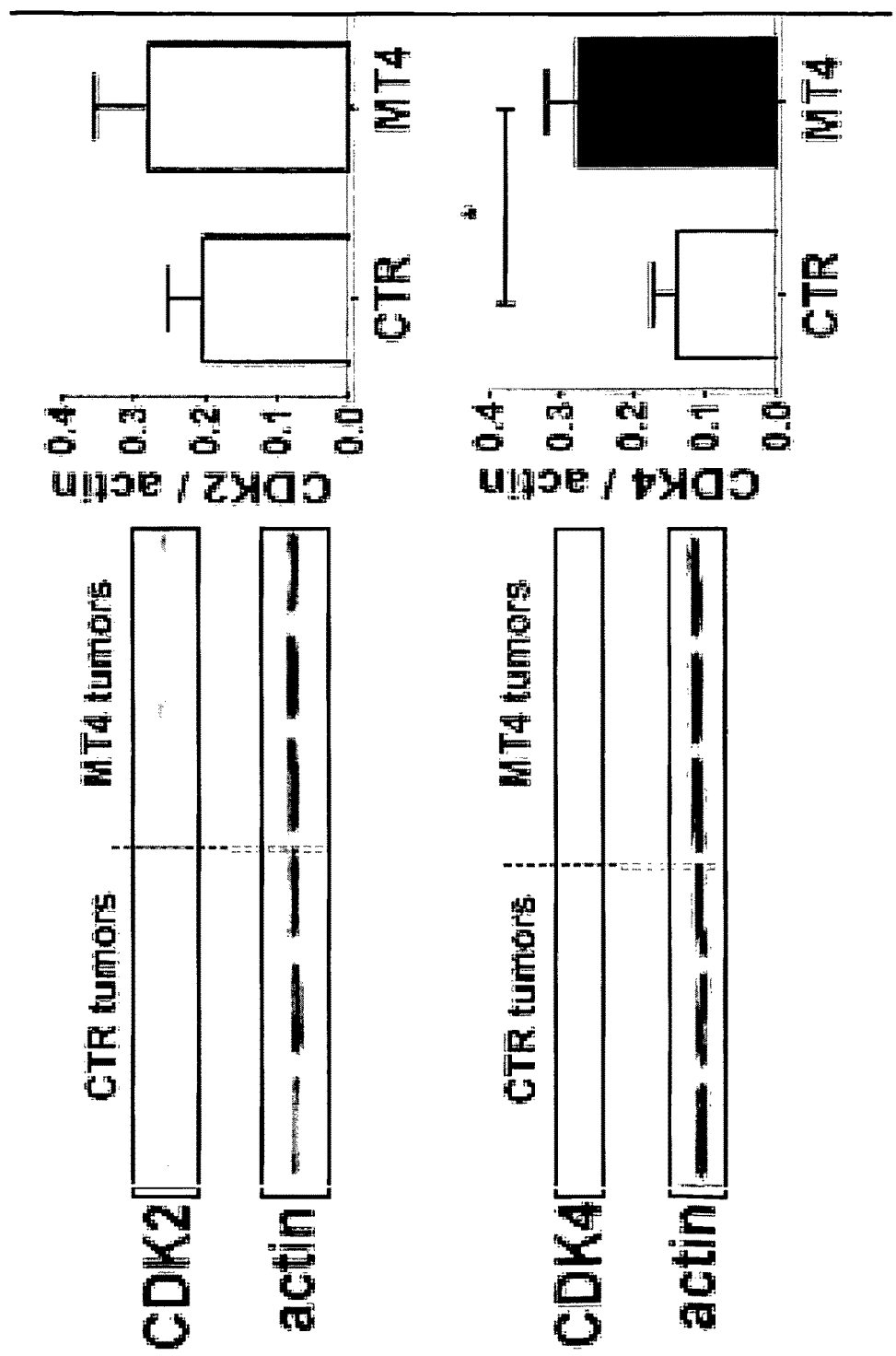
Figure 2E:
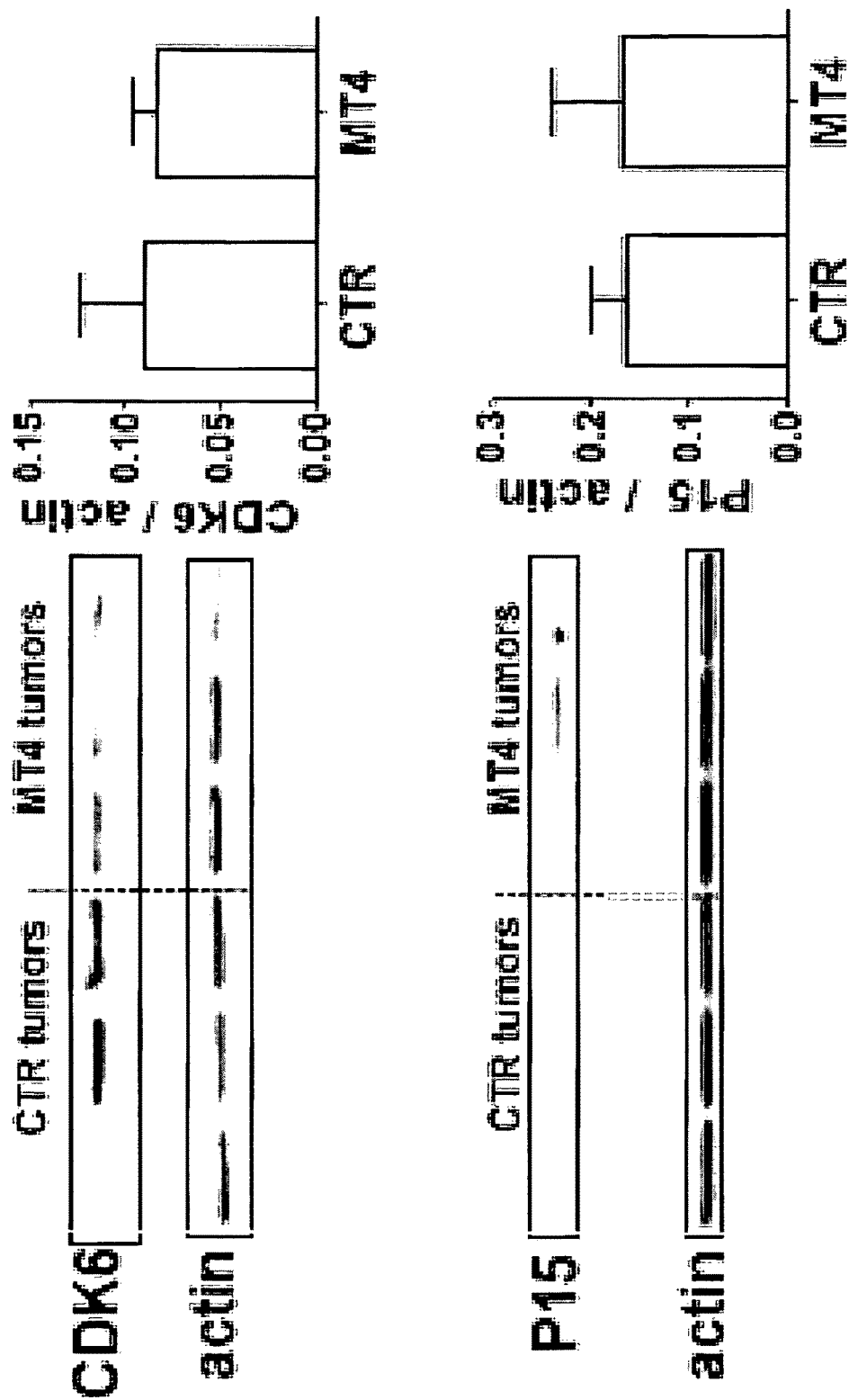
Figure 2F:
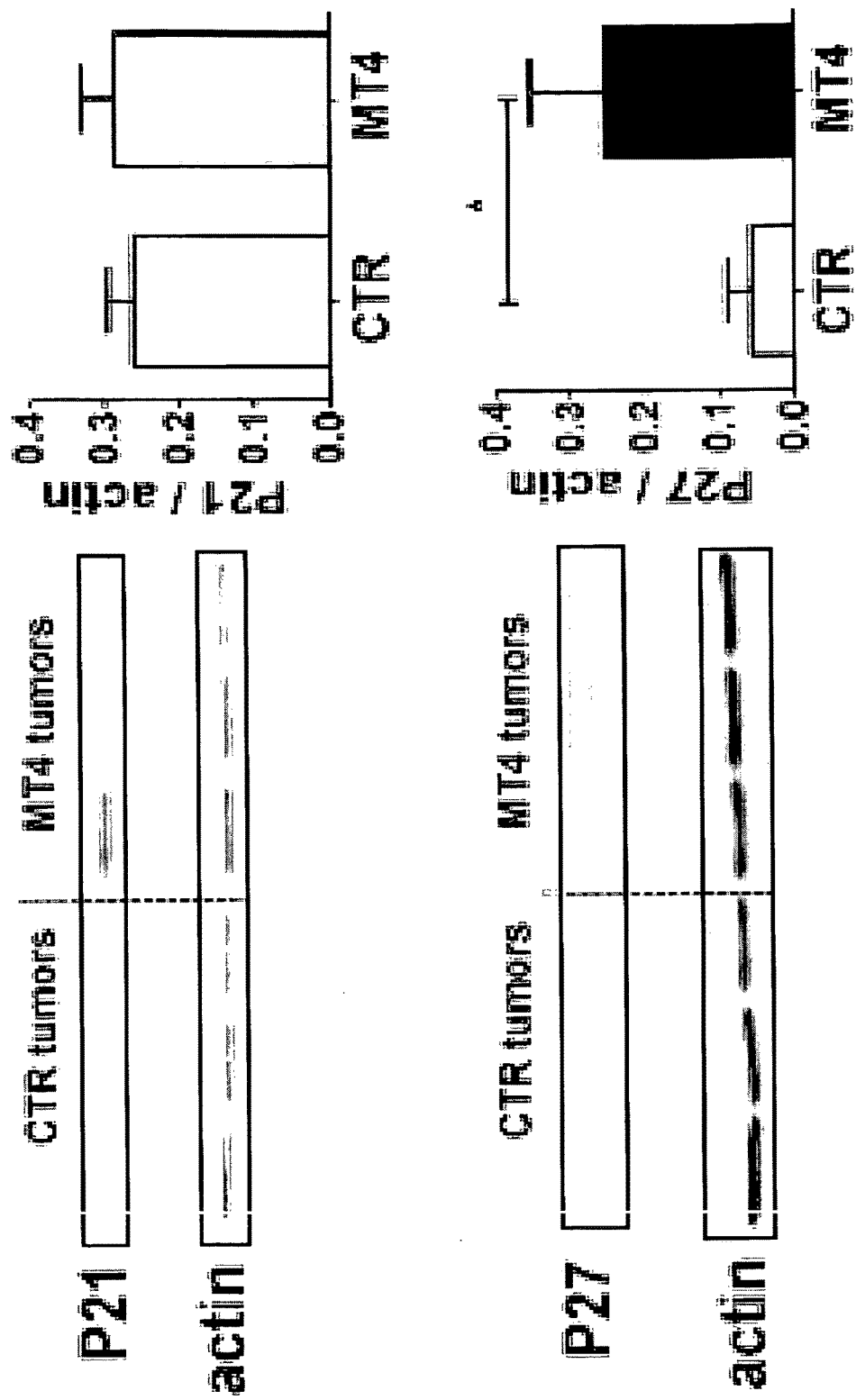
Figure 2G:
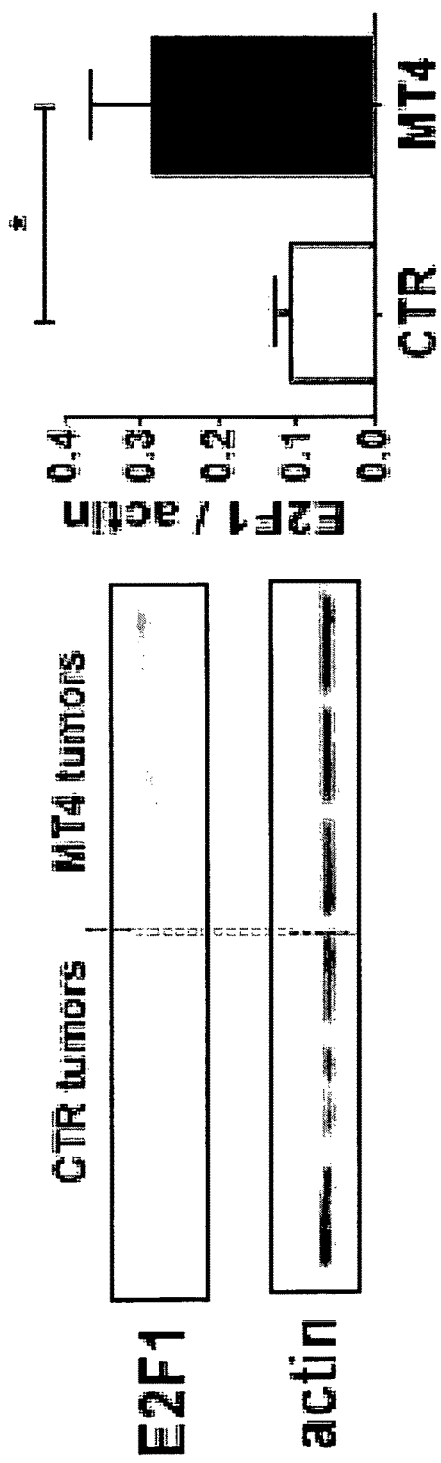

K4H7 VH amino acid sequence (SEQ ID NO: 26)

```
     FW1                          CDR1       FW2                    CDR2
QVQLVQSGGGLVKPGRSLRLSCTASGFTFG    DYAMS    WFRQAPGKGLEWVG    FIRSKAYGGTTEYAASVKG

FW3                              CDR3              FW4
RFTISRDDSKSIAYLQMNSLKTEDTAVYYCTR    GSSGWFLNWFDP    WGQGTLVTVSS
```

K4H7 VL amino acid sequence (SEQ ID NO: 27)

```
     FW1                  CDR1             FW2              CDR2
ETTLTQSPATLSLSPGERATLSC   RASQSISSSYLA   WYQHKPGQAPRLLIY   GASRRAT

FW3                        CDR3            FW4
GIPDRFSGSGSGTDFSLTISRLEPEDFAVYYC    LHYGSSKWT    FGQGTKVEIKR
```

Fig. 17

SEQUENCE LISTING

<160> NUMBER OF SEQ ID NOS: 28

<210> SEQ ID NO 1

```
<211> LENGTH: 603
<212> TYPE: PRT
<213> ORGANISM: Homo sapiens

<400> SEQUENCE: 1

Met Arg Arg Arg Ala Arg Gly Pro Gly Pro Pro Pro Gly Pro
1               5                   10                  15

Gly Leu Ser Arg Leu Pro Leu Pro Leu Leu Leu Leu Ala Leu Gly
            20                  25                  30

Thr Arg Gly Gly Cys Ala Ala Pro Ala Pro Ala Arg Glu Asp
        35                  40                  45

Leu Ser Leu Gly Val Glu Trp Leu Ser Arg Phe Gly Tyr Leu Pro Pro
50                  55                  60

Ala Asp Pro Thr Thr Gly Gln Leu Gln Thr Gln Glu Glu Leu Ser Lys
65                  70                  75                  80

Ala Ile Thr Ala Met Gln Gln Phe Gly Gly Leu Glu Ala Thr Gly Ile
                85                  90                  95

Leu Asp Glu Ala Thr Leu Ala Leu Met Lys Thr Pro Arg Cys Ser Leu
            100                 105                 110

Pro Asp Leu Pro Val Leu Thr Gln Ala Arg Arg Arg Arg Gln Ala Pro
        115                 120                 125

Ala Pro Thr Lys Trp Asn Lys Arg Asn Leu Ser Trp Arg Val Arg Thr
130                 135                 140

Phe Pro Arg Asp Ser Pro Leu Gly His Asp Thr Val Arg Ala Leu Met
145                 150                 155                 160

Tyr Tyr Ala Leu Lys Val Trp Ser Asp Ile Ala Pro Leu Asn Phe His
                165                 170                 175

Glu Val Ala Gly Ser Ala Ala Asp Ile Gln Ile Asp Phe Ser Lys Ala
            180                 185                 190

Asp His Asn Asp Gly Tyr Pro Phe Asp Gly Pro Gly Gly Thr Val Ala
        195                 200                 205

His Ala Phe Phe Pro Gly His His His Thr Ala Gly Asp Thr His Phe
210                 215                 220

Asp Asp Asp Glu Ala Trp Thr Phe Arg Ser Ser Asp Ala His Gly Met
225                 230                 235                 240

Asp Leu Phe Ala Val Ala Val His Glu Phe Gly His Ala Ile Gly Leu
                245                 250                 255

Ser His Val Ala Ala Ala His Ser Ile Met Arg Pro Tyr Tyr Gln Gly
            260                 265                 270

Pro Val Gly Asp Pro Leu Arg Tyr Gly Leu Pro Tyr Glu Asp Lys Val
        275                 280                 285

Arg Val Trp Gln Leu Tyr Gly Val Arg Glu Ser Val Ser Pro Thr Ala
290                 295                 300

Gln Pro Glu Glu Pro Pro Leu Leu Pro Glu Pro Pro Asp Asn Arg Ser
305                 310                 315                 320

Ser Ala Pro Pro Arg Lys Asp Val Pro His Arg Cys Ser Thr His Phe
                325                 330                 335

Asp Ala Val Ala Gln Ile Arg Gly Glu Ala Phe Phe Phe Lys Gly Lys
            340                 345                 350

Tyr Phe Trp Arg Leu Thr Arg Asp Arg His Leu Val Ser Leu Gln Pro
        355                 360                 365

Ala Gln Met His Arg Phe Trp Arg Gly Leu Pro Leu His Leu Asp Ser
370                 375                 380

Val Asp Ala Val Tyr Glu Arg Thr Ser Asp His Lys Ile Val Phe Phe
```

```
                385             390             395             400
Lys Gly Asp Arg Tyr Trp Val Phe Lys Asp Asn Asn Val Glu Glu Gly
                    405             410             415

Tyr Pro Arg Pro Val Ser Asp Phe Ser Leu Pro Pro Gly Gly Ile Asp
                420             425             430

Ala Ala Phe Ser Trp Ala His Asn Asp Arg Thr Tyr Phe Phe Lys Asp
            435             440             445

Gln Leu Tyr Trp Arg Tyr Asp Asp His Thr Arg His Met Asp Pro Gly
    450             455             460

Tyr Pro Ala Gln Ser Pro Leu Trp Arg Gly Val Pro Ser Thr Leu Asp
465             470             475             480

Asp Ala Met Arg Trp Ser Asp Gly Ala Ser Tyr Phe Phe Arg Gly Gln
                485             490             495

Glu Tyr Trp Lys Val Leu Asp Gly Glu Leu Glu Val Ala Pro Gly Tyr
                500             505             510

Pro Gln Ser Thr Ala Arg Asp Trp Leu Val Cys Gly Asp Ser Gln Ala
                515             520             525

Asp Gly Ser Val Ala Ala Gly Val Asp Ala Ala Glu Gly Pro Arg Ala
        530             535             540

Pro Pro Gly Gln His Asp Gln Ser Arg Ser Glu Asp Gly Tyr Glu Val
545             550             555             560

Cys Ser Cys Thr Ser Gly Ala Ser Ser Pro Gly Ala Pro Gly Pro
                565             570             575

Leu Val Ala Ala Thr Met Leu Leu Leu Pro Pro Leu Ser Pro Gly
                580             585             590

Ala Leu Trp Thr Ala Ala Gln Ala Leu Thr Leu
            595             600
```

<210> SEQ ID NO 2
<211> LENGTH: 2429
<212> TYPE: RNA
<213> ORGANISM: Homo sapiens

<400> SEQUENCE: 2

```
ccggcggggg cgccgcggag agcggagggc gccgggcugc ggaacgcgaa gcggagggcg      60
cgggacccug cacgccgccc gcgggcccau gugagcgcca ugcggcgccg cgcagcccgg     120
ggacccggcc cgccgccccc agggcccgga cucucgcggc ugccgcugcc gcugcugcug     180
cugcuggcgc uggggacccg cggggcugc gccgcgcccg cacccgcgcc gcgcgccgag     240
gaccucagcc ugggagugga guggcuaagc agguucgguu accugccccc ggcugacccc     300
acaacagggc agcugcagac gcaagaggag cugucuaagg ccaucacagc caugcagcag     360
uuugguggcc uggaggccac cggcauccug gacgaggcca cccuggcccu gaugaaaacc     420
ccacgcugcu cccugccaga ccucccuguc cugacccagg ucgcaggag acgccaggcu     480
ccagccccca ccaaguggaa caagaggaac cugucgugga gguccggac guucccacgg     540
gacucaccac uggggcacga cacggugcgu gcacucaugu acuacgcccu caaggucugg     600
agcgacauug cgcccugaa cuuccacgag guggcgggca gcgccgccga cauccagauc     660
gacuucucca aggccgacca uaacgacggc uaccccuucg acggcccgg cggcaccgug     720
gcccacgccu ucuuccccgg ccaccaccac accgccgggg acacccacuu ugacgaugac     780
gaggccugga ccuccgcuc ucggaugcc acgggaugg accuguugc agugccguc     840
cacgaguuug gccacgccau ugggguuaagc caugguggccg cugcacacuc caucaugcgg     900
```

-continued

| | |
|---|---|
| ccguacuacc agggcccggu gggugacccg cugcgcuacg ggcuccccua cgaggacaag | 960 |
| gugcgcgucu ggcagcugua cggugugcgg gagucugugu cucccacggc gcagcccgag | 1020 |
| gagccuccc ugcugccgga gccccccagac aaccggucca gcgccccgcc caggaaggac | 1080 |
| gugccccaca gaugcagcac ucacuuugac gcgguggccc agauccgggg ugaagcuuuc | 1140 |
| uucuucaaag gcaaguacuu cuggcggcug acgcgggacc ggcaccuggu guccugcag | 1200 |
| ccggcacaga ugcaccgcuu cuggcggggc cugccgcugc accuggacag cguggacgcc | 1260 |
| guguacgagc gcaccagcga ccacaagauc gucuucuuua aggagacag guacuggug | 1320 |
| uucaaggaca auaacguaga ggaaggauac ccgcgcccg ucccgacuu cagccucccg | 1380 |
| ccuggcggca ucgacgcugc cuucuccugg gcccacaaug acaggacuua uuucuuuaag | 1440 |
| gaccagcugu acuggcgcua cgaugaccac acgaggcaca uggaccccgg cuaccccgcc | 1500 |
| cagagccccc ugugaggg gugccccagc acgcuggacg acgccaugcg cuggucgac | 1560 |
| ggugccuccu acuucuuccg uggccaggag uacuggaaag ugcuggaugg cgagcuggag | 1620 |
| guggcacccg gguacccaca guccacgcc cgggacuggc uggugugugg agacucacag | 1680 |
| gccgauggau cuguggcugc gggcguggac gcggcagagg ggccccgcgc cccuccagga | 1740 |
| caacaugacc agagccgcuc ggaggacggu uacgaggucu gcucaugcac cucuggggca | 1800 |
| uccucucccc cggggggcccc aggcccacug guggcugcca ccaugcugcu gcugcugccg | 1860 |
| ccacugucac caggcgcccu guggacagcg gcccaggccc ugacgcuaug acacacagcg | 1920 |
| cgagcccaug agaggacaga ggcggugga cagccuggcc acagagggca aggacugugc | 1980 |
| cggagucccu gggggaggug cuggcgcggg augaggacgg gccacccugg caccggaagg | 2040 |
| ccagcagagg gcacugcccg ccagggcugg gcaggcucag guggcaagga cggagcuguc | 2100 |
| cccuagugag ggacugugu gacugacgag ccgagggug gccgcuccag aagggugccc | 2160 |
| agucaggccg caccgccgcc agccuccucc ggcccuggag ggagcaucuc gggcuggggg | 2220 |
| cccacccuc ucugugccgg cgccaccaac cccacccaca cugcugccug gugucccgc | 2280 |
| cggcccacag ggcucucgu cccaggucc caguggggca gcccucccca cagacgagcc | 2340 |
| ccccacaugg ugccgcggca cguccccccu gugacgcguu ccagaccaac augaccucuc | 2400 |
| ccugcuuugu aaaaaaaaaa aaaaaaaa | 2429 |

<210> SEQ ID NO 3
<211> LENGTH: 10
<212> TYPE: PRT
<213> ORGANISM: Artificial
<220> FEATURE:
<223> OTHER INFORMATION: synthetic peptide

<400> SEQUENCE: 3

Glu Gln Lys Leu Ile Ser Glu Glu Asp Leu
1               5                   10

<210> SEQ ID NO 4
<211> LENGTH: 45
<212> TYPE: DNA
<213> ORGANISM: Artificial
<220> FEATURE:
<223> OTHER INFORMATION: synthetic DNA

<400> SEQUENCE: 4
gcccccagac tacaaggatg acgacgataa gaaccggtcc agcgc         45

<210> SEQ ID NO 5

```
<211> LENGTH: 45
<212> TYPE: DNA
<213> ORGANISM: Artificial
<220> FEATURE:
<223> OTHER INFORMATION: synthetic DNA

<400> SEQUENCE: 5
gcgctggacc ggttcttatc gtcgtcatcc ttgtagtctg ggggc          45

<210> SEQ ID NO 6
<211> LENGTH: 24
<212> TYPE: DNA
<213> ORGANISM: Artificial
<220> FEATURE:
<223> OTHER INFORMATION: synthetic DNA

<400> SEQUENCE: 6
ggacatgggc caagaagaca tgtt                                 24

<210> SEQ ID NO 7
<211> LENGTH: 24
<212> TYPE: DNA
<213> ORGANISM: Artificial
<220> FEATURE:
<223> OTHER INFORMATION: synthetic DNA

<400> SEQUENCE: 7
ctccttcact gtttggaggt ggtt                                 24

<210> SEQ ID NO 8
<211> LENGTH: 24
<212> TYPE: DNA
<213> ORGANISM: Artificial
<220> FEATURE:
<223> OTHER INFORMATION: synthetic DNA

<400> SEQUENCE: 8
gcaaccactg gaggtgaaga acaa                                 24

<210> SEQ ID NO 9
<211> LENGTH: 24
<212> TYPE: DNA
<213> ORGANISM: Artificial
<220> FEATURE:
<223> OTHER INFORMATION: synthetic DNA

<400> SEQUENCE: 9
ctcatctggg tcgatgagct gaaa                                 24

<210> SEQ ID NO 10
<211> LENGTH: 24
<212> TYPE: DNA
<213> ORGANISM: Artificial
<220> FEATURE:
<223> OTHER INFORMATION: synthetic DNA

<400> SEQUENCE: 10
cctgttcgct ctgggtattg tgtt                                 24

<210> SEQ ID NO 11
<211> LENGTH: 24
<212> TYPE: DNA
<213> ORGANISM: Artificial
<220> FEATURE:
<223> OTHER INFORMATION: synthetic DNA

<400> SEQUENCE: 11
```
cttgtcctcc tgcaccaaaa acct                                                  24

<210> SEQ ID NO 12
<211> LENGTH: 24
<212> TYPE: DNA
<213> ORGANISM: Artificial
<220> FEATURE:
<223> OTHER INFORMATION: synthetic DNA

<400> SEQUENCE: 12
cgtggactct tcggagaact ttca                                                  24

<210> SEQ ID NO 13
<211> LENGTH: 24
<212> TYPE: DNA
<213> ORGANISM: Artificial
<220> FEATURE:
<223> OTHER INFORMATION: synthetic DNA

<400> SEQUENCE: 13
atgatggtgg tggtgacact atgg                                                  24

<210> SEQ ID NO 14
<211> LENGTH: 24
<212> TYPE: DNA
<213> ORGANISM: Artificial
<220> FEATURE:
<223> OTHER INFORMATION: synthetic DNA

<400> SEQUENCE: 14
cgctccctca aggagataag tgat                                                  24

<210> SEQ ID NO 15
<211> LENGTH: 24
<212> TYPE: DNA
<213> ORGANISM: Artificial
<220> FEATURE:
<223> OTHER INFORMATION: synthetic DNA

<400> SEQUENCE: 15
ctcagagttc tccacaaact ccct                                                  24

<210> SEQ ID NO 16
<211> LENGTH: 24
<212> TYPE: DNA
<213> ORGANISM: Artificial
<220> FEATURE:
<223> OTHER INFORMATION: synthetic DNA

<400> SEQUENCE: 16
ccctcatcac tggttgtggt tcat                                                  24

<210> SEQ ID NO 17
<211> LENGTH: 24
<212> TYPE: DNA
<213> ORGANISM: Artificial
<220> FEATURE:
<223> OTHER INFORMATION: synthetic DNA

<400> SEQUENCE: 17
ccacaggagc acagtcatct tgat                                                  24

<210> SEQ ID NO 18
<211> LENGTH: 24
<212> TYPE: DNA

```
<213> ORGANISM: Artificial
<220> FEATURE:
<223> OTHER INFORMATION: synthetic DNA

<400> SEQUENCE: 18
ggagccgact atgactactc agaa                                             24

<210> SEQ ID NO 19
<211> LENGTH: 24
<212> TYPE: DNA
<213> ORGANISM: Artificial
<220> FEATURE:
<223> OTHER INFORMATION: synthetic DNA

<400> SEQUENCE: 19
catgttactg cttccaggtg ctct                                             24

<210> SEQ ID NO 20
<211> LENGTH: 5
<212> TYPE: PRT
<213> ORGANISM: Artificial
<220> FEATURE:
<223> OTHER INFORMATION: synthetic peptide

<400> SEQUENCE: 20

Asp Tyr Ala Met Ser
1               5

<210> SEQ ID NO 21
<211> LENGTH: 19
<212> TYPE: PRT
<213> ORGANISM: Artificial
<220> FEATURE:
<223> OTHER INFORMATION: synthetic peptide

<400> SEQUENCE: 21

Phe Ile Arg Ser Lys Ala Tyr Gly Gly Thr Thr Glu Tyr Ala Ala Ser
1               5                   10                  15

Val Lys Gly

<210> SEQ ID NO 22
<211> LENGTH: 12
<212> TYPE: PRT
<213> ORGANISM: Artificial
<220> FEATURE:
<223> OTHER INFORMATION: synthetic peptide

<400> SEQUENCE: 22

Gly Ser Ser Gly Trp Phe Leu Asn Trp Phe Asp Pro
1               5                   10

<210> SEQ ID NO 23
<211> LENGTH: 12
<212> TYPE: PRT
<213> ORGANISM: Artificial
<220> FEATURE:
<223> OTHER INFORMATION: synthetic peptide

<400> SEQUENCE: 23

Arg Ala Ser Gln Ser Ile Ser Ser Ser Tyr Leu Ala
1               5                   10

<210> SEQ ID NO 24
<211> LENGTH: 7
<212> TYPE: PRT
<213> ORGANISM: Artificial
```

```
<220> FEATURE:
<223> OTHER INFORMATION: synthetic peptide

<400> SEQUENCE: 24

Gly Ala Ser Arg Arg Ala Thr
1               5

<210> SEQ ID NO 25
<211> LENGTH: 9
<212> TYPE: PRT
<213> ORGANISM: Artificial
<220> FEATURE:
<223> OTHER INFORMATION: synthetic peptide

<400> SEQUENCE: 25

Leu His Tyr Gly Ser Ser Lys Trp Thr
1               5

<210> SEQ ID NO 26
<211> LENGTH: 123
<212> TYPE: PRT
<213> ORGANISM: Artificial
<220> FEATURE:
<223> OTHER INFORMATION: synthetic peptide

<400> SEQUENCE: 26

Gln Val Gln Leu Val Gln Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Gly Ser Ser Gly Trp Phe Leu Asn Trp Phe Asp Pro
            100                 105                 110

Trp Gly Gln Gly Thr Leu Val Thr Val Ser Ser
        115                 120

<210> SEQ ID NO 27
<211> LENGTH: 109
<212> TYPE: PRT
<213> ORGANISM: Artificial
<220> FEATURE:
<223> OTHER INFORMATION: synthetic peptide

<400> SEQUENCE: 27

Glu Thr Thr Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Ala Trp Tyr Gln His Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Ser Leu Thr Ile Ser Arg Leu Glu
65                  70                  75                  80
```

```
Pro Glu Asp Phe Ala Val Tyr Tyr Cys Leu His Tyr Gly Ser Ser Lys
                85                  90                  95

Trp Thr Phe Gly Gln Gly Thr Lys Val Glu Ile Lys Arg
            100                 105

<210> SEQ ID NO 28
<211> LENGTH: 251
<212> TYPE: PRT
<213> ORGANISM: Artificial
<220> FEATURE:
<223> OTHER INFORMATION: synthetic peptide

<400> SEQUENCE: 28

Gln Val Gln Leu Val Gln Ser Gly Gly Leu Val Lys Pro Gly Arg
1               5                   10                  15

Ser Leu Arg Leu Ser Cys Thr Ala Ser Gly Phe Thr Phe Gly Asp Tyr
                20                  25                  30

Ala Met Ser Trp Phe Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Gly Ser Ser Gly Trp Phe Leu Asn Trp Phe Asp Pro
                100                 105                 110

Trp Gly Gln Gly Thr Leu Val Thr Val Ser Ser Leu Glu Gly Gly Gly
            115                 120                 125

Gly Ser Gly Gly Gly Gly Ser Gly Gly Gly Gly Ser Glu Leu Glu Thr
    130                 135                 140

Thr Leu Thr Gln Ser Pro Ala Thr Leu Ser Leu Ser Pro Gly Glu Arg
145                 150                 155                 160

Ala Thr Leu Ser Cys Arg Ala Ser Gln Ser Ile Ser Ser Ser Tyr Leu
                165                 170                 175

Ala Trp Tyr Gln His Lys Pro Gly Gln Ala Pro Arg Leu Leu Ile Tyr
            180                 185                 190

Gly Ala Ser Arg Arg Ala Thr Gly Ile Pro Asp Arg Phe Ser Gly Ser
    195                 200                 205

Gly Ser Gly Thr Asp Phe Ser Leu Thr Ile Ser Arg Leu Glu Pro Glu
    210                 215                 220

Asp Phe Ala Val Tyr Tyr Cys Leu His Tyr Gly Ser Ser Lys Trp Thr
225                 230                 235                 240

Phe Gly Gln Gly Thr Lys Val Glu Ile Lys Arg
            245                 250
```

COMBINATION TREATMENT OF CANCER

CROSS-REFERENCE TO RELATED APPLICATIONS

This application is a US National Phase filing of PCT/EP2013/068120, filed on Sep. 2, 2013, which claims priority of 12183618.3 (EP), filed on Sep. 7, 2012, the entire disclosures of which are hereby expressly incorporated by reference.

The present invention relates to MT4-MMP inhibitor and EGFR inhibitor for use in the treatment of cancer, wherein said MT4-MMP inhibitor and EGFR inhibitor are different from each other.

BACKGROUND

Tumor growth relies on the dysregulation of cancer cell properties associated with an intense host tissue remodeling. Mitogenic signals consist of growth factors acting through cell surface receptors, extracellular matrix (ECM) components and cell-cell adhesion molecules. Several proteases are known to control the bioavailability and activity of growth factors, cytokines and chemokines that target specific receptors regulating cell survival, growth, migration, as well as inflammation and angiogenesis. These effects rely on the release of active molecules from the ECM, the cleavage of growth factors binding proteins or the shedding of receptor ligands from the cell surface. Several protease of the zinc-binding endopeptidase family including matrix metalloproteinases (MMPs) and A Disintegrin and Metalloproteinases (ADAMs) are key regulators of molecules acting at the cell surface. They are able to degrade almost all ECM components as well as other molecules including cytokines and growth factors. For instance, MMP9 and MMP2 are responsible for the release of the Vascular Endothelial Growth Factor (VEGF) from the ECM and the activation of Transforming Growth Factor-beta (TGFβ), whereas ADAM10 and TACE (ADAM17) shed several EGFR ligands from the cell surface such as TGFα, amphiregulin and proHB-EGF.

The membrane insertion of ADAMs and membrane type-MMPs (MT-MMPs) helps these proteases to localize to specific membrane microdomains and reach key membrane and pericellular proteins to confer a unique set of regulatory mechanisms. A growing number of evidences underline a functional crosstalk between cell surface-associated proteases and kinases during cancer progression. MT-MMPs that play a key role in cancer progression and vascular diseases are linked to the cell membrane either through a transmembrane domain (MT1-, MT2-, MT3-, MT5-MMP) or a glycosyl phosphatidyl inositol (GPI) anchor (MT4- and MT6-MMP). The transmembrane MT1-MMP has been reported to induce intracellular signaling through Scr and MAP kinases cascade. In sharp contrast to this well documented MT1-MMP-mediated signaling, a putative outside-in cell signaling through the GPI anchored MT-MMPs (MT4 and MT6-MMPs) is unknown. Although, most MMPs are produced by host cells, MT4-MMP (MMP17) is produced by tumor cells in human breast cancer samples (Chabottaux, V. et al. "Membrane-type 4 matrix metalloproteinase promotes breast cancer growth and metastases", Cancer Res 66, 5165-5172 (2006)). MT4-MMP emerged recently as a key intrinsic feature of breast cancer cells that stimulates tumor growth and metastasis into the lung, but into to lymph nodes (Chabottaux, V. et al., Cancer Res 66, 5165-5172 (2006); Chabottaux, V., et al., J Cell Mol Med 13, 4002-4013 (2009); Host, L., et al., Int J Cancer, doi: 10.1002/ijc.27436 (2012)). This impact on hematogenous dissemination is related to changes in blood vasculature characterized by pericyte detachment, vessel enlargement and destabilization (Chabottaux, V., et al., J Cell Mol Med 13, 4002-4013 (2009)). The cellular interaction of MT4-MMP which contributes to tumor aggressiveness was not known before.

The object of the present invention was to determine whether MT4-MMP could contribute to an outside-in signaling involved in tumor aggressiveness and to provide new pharmaceutical compositions for use in the treatment of cancer.

SUMMARY OF THE PRESENT INVENTION

When pursuing the present invention the inventors started studies in order to determine whether this MT4-MMP could contribute to an outside-in signaling involved in tumor aggressiveness, and to determine which signaling pathway is triggered by MT4-MMP and to find new therapies for cancer. The present inventors found that MT4-MMP activates EGFR.

Therefore, the present invention provides MT4-MMP inhibitor and EGFR inhibitor for use in the treatment of cancer, wherein said MT4-MMP inhibitor and EGFR inhibitor are different from each other.

The skilled person understands that the condition which stipulates that MT4-MMP inhibitor and EGFR inhibitor are different from each other, still allows that the inhibitors may belong or not to the same class of substances (such as an antibody or small molecule inhibitor), but have different specificities. This means that the present invention provides MT4-MMP inhibitor and EGFR inhibitor for use in the treatment of cancer, wherein for example an antibody or small molecule inhibitor specifically binding to MT4-MMP and an antibody or small molecule inhibitor specifically binding to EGFR is used.

Preferably, said MT4-MMP inhibitor and said EGFR inhibitor are administered simultaneously, sequentially or separately.

Further preferred, the MT4-MMP inhibitor reduces or inhibits one or more of the effects of MT4-MMP selected from the list: effects of MT4-MMP on the activation (ligand binding and/or receptor phosphorylation), the activity (downstream intracellular signaling, induction of cell responses including proliferation, migration and survival), the bioavailability (stability, internalisation and recycling) or localization at the cell surface, in the cytoplasm or in the nucleus of EGFR. These function blocking activities can be tested in vitro in cells expressing MT4-MMP and EGFR, endogenously or exogenously (transfected cells). Cell response to the inhibitor can be either tested in vitro (phosphorylation of the EGFR or of downstream signaling molecules, cell proliferation assay, cell migration assay, apoptosis assay) in 2D cultures or 3D cultures (Matrigel® assay as described below in example 4) (see FIGS. 3, 4 and 7) or in vivo (Matrigel® plug assay, xenograft) (see FIGS. 1, 2 and 6, and Host, L., et al., Int J Cancer, doi: 10.1002/ijc.27436, 2012).

It is particularly preferred, that the MT4-MMP inhibitor reduces or inhibits the effect of MT4-MMP on the ligand binding of EGFR, resulting into a lower degree of ligand bound to EGFR, compared to the absence of MT4-MMP inhibitor, wherein the ligand preferably is selected from the group consisting of EGF, transforming growth factor-alpha (TGFα), amphiregulin (AR) and heparin-binding EGF-like growth factor (HB-EGF).

It is particularly preferred, that the MT4-MMP inhibitor reduces or inhibits the effect of MT4-MMP on the receptor phosphorylation of EGFR, resulting into a lower degree of phosphorylated amino acid residues of EGFR polypeptide, compared to the absence of MT4-MMP inhibitor, wherein the amino acid position to be phosphorylated preferably is selected from the list consisting of Y992, Y1045, Y1068, Y1148 and Y1173, in particular Y1173.

It is alternatively preferred that the MT4-MMP inhibitor reduces EGFR dependent proliferation of cancer cells resulting in a lower level of cyclin-dependent kinase (CDK4) and/or cyclins (cyclin D1, cyclin D3 and cyclin E), a higher level of the activated tumor suppressor protein (preferably non-phosphorylated Retinoblastoma protein), compared to the absence of MT4-MMP inhibitor.

In another preferred embodiment of the present invention said MT4-MMP inhibitor is selected from the group consisting of monoclonal or polyclonal antibody directed to MT4-MMP, anti-sense nucleic acid or chemical analogue thereof specifically hybridizing to the MT4-MMP mRNA, chemical compound, fragment of MT4-MMP.

In one embodiment the MT4-MMP inhibitor is an antibody which may be a common antibody (which is composed of two heavy protein chains and two light chains), Fab fragments of a common antibody, single-chain variable fragments (scFV) or single-domain antibody (sdAb). Said antibody specifically binds to MT4-MMP, which preferably has an amino acid sequence shown in SEQ ID NO: 1.

In another embodiment the MT4-MMP inhibitor is an antisense nucleic acid. Said antisense nucleic acid hybridises with MT4-MMP mRNA, which preferably has an nucleic acid sequence shown in SEQ ID NO: 2.

In yet another embodiment the MT4-MMP inhibitor is a fragment of MT4-MMP, preferably an extracellular fragment of MT4-MMP which interferes with signaling between MT4-MMP and EGFR. Said fragment of MT4-MMP is at least 8 consecutive amino acid residues and up to 10, 12, 15, 18, 20, 30, 50, 80, 100, 150, 200, 250, 300, 350, 400, 450, 500, 550 consecutive amino acids in length of the amino acid sequence shown in SEQ ID NO: 1. The amino acid sequence of said fragment may have further deletions, additions and replacements of 1 to 20 amino acid residue positions.

The present invention makes use of a combination treatment using MT4-MMP and an EGFR inhibitor. An EGFR inhibitor is an active agent which selectively decreases or blocks the activity (i.e. binding to ligands, phosphorylation and downstream signaling), and the biological effects of EGFR, and/or modifies half-life or subcellular localisation (membrane versus cytoplasmic or nuclear localization; internalisation and recycling) of EGFR. In particular, an EGFR inhibitor is an active agent which selectively decreases or blocks one or more of the following: blockage of ligand binding, inhibition of tyrosine kinase activity, inhibition of induced cell proliferation, inhibition of EGFR internalization, inhibition of translocation into the nucleus.

Said EGFR inhibitor may be a monoclonal or polyclonal antibody specifically binding to EGFR, an anti-sense nucleic acid or chemical analogue thereof specifically hybridizing to EGFR mRNA or a chemical compound.

Still further preferred said EGFR inhibitor is selected from the group consisting of cetuximab, panitumumab, zalutumumab, nimotuzumab, erlotinib, gefitinib, lapatinib, neratinib, canertinib, vandetanib, afatinib, TAK-285 (dual HER2 and EGFR inhibitor), ARRY334543 (dual HER2 and EGFR inhibitor), Dacomitinib (pan-ErbB inhibitor), OSI-420 (Desmethyl Erlotinib) (EGFR inhibitor), AZD8931 (EGFR, HER2 and HER3 inhibitor), AEE788 (NVP-AEE788) (EGFR, HER2 and VEGFR 1/2 inhibitor), Pelitinib (EKB-569) (pan-ErbB inhibitor), CUDC-101 (EGFR, HER2 and HDAC inhibitor), XL647 (dual HER2 and EGFR inhibitor), BMS-599626 (AC480) (dual HER2 and EGFR inhibitor), PKC412 (EGFR, PKC, cyclic AMP-dependent protein kinase and S6 kinase inhibitor), BIBX1382 (EGFR inhibitor) and AP26113 (ALK and EGFR inhibitor) and derivatives and combinations thereof.

It is particularly preferred that the EGFR inhibitor is selected from the group consisting of cetuximab, panitumumab, zalutumumab, nimotuzumab, erlotinib, gefitinib, lapatinib, neratinib, canertinib, vandetanib, afatinib and AP26113 and combinations thereof.

In a particularly preferred embodiment of the present invention said MT4-MMP inhibitor is i) monoclonal or polyclonal antibody specifically binding to MT4-MMP or ii) anti-sense nucleic acid or chemical analogue thereof specifically hybridizing to the MT4-MMP mRNA; and wherein said EGFR inhibitor is selected from the group consisting of cetuximab, panitumumab, zalutumumab, nimotuzumab, erlotinib, gefitinib, lapatinib, neratinib, canertinib, vandetanib, afatinib, TAK-285 (dual HER2 and EGFR inhibitor), ARRY334543 (dual HER2 and EGFR inhibitor), Dacomitinib (pan-ErbB inhibitor), OSI-420 (Desmethyl Erlotinib) (EGFR inhibitor), AZD8931 (EGFR, HER2 and HER3 inhibitor), AEE788 (NVP-AEE788) (EGFR, HER2 and VEGFR 1/2 inhibitor), Pelitinib (EKB-569) (pan-ErbB inhibitor), CUDC-101 (EGFR, HER2 and HDAC inhibitor), XL647 (dual HER2 and EGFR inhibitor), BMS-599626 (AC480) (dual HER2 and EGFR inhibitor), PKC412 (EGFR, PKC, cyclic AMP-dependent protein kinase and S6 kinase inhibitor), BIBX1382 (EGFR inhibitor) and AP26113 (ALK and EGFR inhibitor), and derivatives and combinations thereof.

Said cancer to be treated preferably is characterized in that compared to the respective normal tissue cells one or more of the following features apply: the respective cancer cells i) express MT4-MMP; ii) show an increased MT4-MMP-mediated level of EGFR ligands; iii) show increased expression of EGFR; iv) show an increased activity of EGFR; v) show an increased level of phosphorylated EGFR; vi) show a different subcellular localization of EGFR (membrane, cytoplasmic and/or nuclear). The activity of EGFR can be measured by determining the EGFR phosphorylation. In particular, the EGFR phosphorylation can be analyzed by using specific antibodies directed to phosphorylated EGFR. The phosphorylated EGFR represent active form of EGFR. Such antibodies directed to phosphorylated EGFR do not bind to non-phosphorylated EGFR, which are not active. The increased activity of EGFR may preferably be due to an increased MT4-MMP-mediated activation of EGFR. Measuring an increased activity of EGFR may be partially or completely due to increased EGFR protein expression.

Further preferred, said cancer is characterized in that compared to the respective normal tissue cells the cancer cells show an increased MT4-MMP-mediated level of EGFR ligands. Said ligand of EGFR preferably is selected from the group consisting of EGF, transforming growth factor-alpha (TGFα), amphiregulin (AR) and heparin-binding EGF-like growth factor (HB-EGF).

In another preferred embodiment of the present invention the MT4-MMP-mediated activation of EGFR is effected by direct protein-protein-interaction of MT4-MMP and EGFR.

Further preferred, said cancer to be treated by the combination treatment is EGFR-positive cancer as determined by immunohistochemistry. A cancer tissue or tumor is considered EGFR-positive, if EGFR protein can be detected in the tumor cells by immunohistochemical staining using anti-EGFR antibodies. A tumor tissue or tumor cell is EGFR-positive, if it possesses any staining above background.

In an alternative assessment a cancer tissue or tumor is considered EGFR-positive, if the cancer tissue or tumor shows increased EGFR activity in particular increased EGFR phosphorylation compared to the respective normal (non-disease/non-tumor) tissue. In particular, the EGFR phosphorylation can be analyzed by using specific antibodies directed to phosphorylated EGFR. The phosphorylated EGFR represent active form of EGFR. Such antibodies directed to phosphorylated EGFR do not bind to non-phosphorylated EGFR, which are not active.

Still further preferred said cancer to be treated by the combination treatment is of epithelial cancer type. In a particularly preferred embodiment said cancer to be treated by the combination treatment is selected from the group consisting of non small cell lung cancer (NSCLC), renal cell cancer, glioblastoma, breast cancer, lung cancer, head and neck cancer, colorectal cancer, ovarian cancer, cervical cancer, bladder cancer, oesophagial cancer, gastric cancer, pancreatic cancer, endometrial cancer, thyroid cancer, squamous cell carcinoma and brain cancer, further preferred breast cancer, in particular triple-negative breast cancer (TNBC) subtype or basal-like subtype breast cancer (BLBC). This list of cancer types all belong to the epithelial cancer type.

It is particularly preferred that said cancer is triple-negative breast cancer (TNBC) subtype or basal-like subtype breast cancer (BLBC). Gene expression profilings have made a significant contribution to the understanding of breast cancers with the identification of different clinico-pathological subtypes, which are a) luminal A (estrogen positive and histology low grade), b) luminal B (estrogen positive and histology high grade), c) HER2 positive and d) basal-like subtype which are estrogen receptor (ER), progesterone receptor (PR) and HER2 negative. This latter subgroup of basal-like breast cancer (BLBC) defined by gene-expression profiling shares morphological and genetic abnormalities with the so-called triple-negative breast cancer (TNBC) subtype. Triple-negative breast cancer (TNBC) subtype is estrogen receptor (ER) negative, progesterone receptor (PR) negative and HER2 negative, as determined by immunohistochemistry. TNBC represent about 15% of invasive breast and do not respond to hormonal therapy (such as tamoxifen or aromatase inhibitors) or HER2-targeted therapies such as Herceptin (trastuzumab). They show an aggressive pattern of progression with a high rate of early-occurring metastasis into the lung and the brain, but rarely into liver and lymph node. With BLBC and TNBC, the oncologist faces one of the most challenging subtypes of invasive breast cancer to treat because of the lack of specific therapies. Now according to the present invention, the combination treatment making use MT4-MMP inhibitor and EGFR inhibitor provides a targeted therapy for BLBC and TNBC.

The present invention make use of a combination of antibodies raised against MT4-MMP and EGFR, on human tumor samples by immunohistochemistry, to classify tumors and predict their responsiveness to targeted anti-EGFR therapies.

The present invention further provides an antibody, preferably a monoclonal antibody which specifically binds to MT4-MMP, which is any one selected from the following antibodies:

(a) an antibody comprising
   (i) a heavy chain variable domain which comprises a CDR1 region shown in SEQ ID NO: 20, a CDR2 region shown in SEQ ID NO: 21 and a CDR3 region shown in SEQ ID NO: 22, and
   (ii) a light chain variable domain which comprises a CDR1 region shown in SEQ ID NO: 23, a CDR2 region shown in SEQ ID NO: 24 and a CDR3 region shown in SEQ ID NO: 25;
(b) an antibody having the amino acid sequence shown in SEQ ID NO: 26 as the amino acid sequence of a H chain variable region (VH), and having the amino acid sequence shown in SEQ ID NO: 27 as the amino acid sequence of a L chain variable region (VL);
(c) a scFv (single chain variable fragment) antibody comprising the amino acid sequence shown in SEQ ID NO: 28.

The antibody according to the present invention, hereinafter also described as K4H7, specifically binds to MT4-MMP protein and has neutralizing function, i.e. neutralizes and inhibits the action of MT4-MMP protein.

The present invention also provides a kit or pharmaceutical combination comprising: i) a pharmaceutical formulation comprising MT4-MMP inhibitor and EGFR inhibitor and a pharmaceutically acceptable carrier or diluent; or ii) a first pharmaceutical formulation comprising MT4-MMP inhibitor and a second pharmaceutical formulation comprising EGFR inhibitor, wherein the first and the second pharmaceutical formulation comprises a pharmaceutically acceptable carrier or diluent. The kit or pharmaceutical combination comprising said pharmaceutical formulation or said pharmaceutical formulations is for use in the treatment of cancer.

The present invention also provides a pharmaceutical composition comprising MT4-MMP inhibitor and EGFR inhibitor and a pharmaceutically acceptable carrier or diluent.

In a preferred embodiment of the pharmaceutical composition said MT4-MMP inhibitor is selected from the group consisting of monoclonal or polyclonal antibody specifically binding to MT4-MMP, anti-sense nucleic acid or chemical analogue thereof specifically hybridizing to the MT4-MMP mRNA, chemical compound, fragment of MT4-MMP.

In a further preferred pharmaceutical composition according to the present invention said EGFR inhibitor is selected from the group consisting of cetuximab, panitumumab, zalutumumab, nimotuzumab, erlotinib, gefitinib, lapatinib, neratinib, canertinib, vandetanib, afatinib, TAK-285, ARRY334543, Dacomitinib, OSI-420, AZD8931, AEE788, Pelitinib, CUDC-101, XL647, BMS-599626, PKC412, BIBX1382 and AP26113, and derivatives and combinations thereof.

In a particular preferred embodiment of the pharmaceutical composition according to the present invention said MT4-MMP inhibitor is a monoclonal antibody which specifically binds to MT4-MMP, which is any one selected from the following antibodies:

(a) an antibody comprising
   (i) a heavy chain variable domain which comprises a CDR1 region shown in SEQ ID NO: 20, a CDR2 region shown in SEQ ID NO: 21 and a CDR3 region shown in SEQ ID NO: 22, and
   (ii) a light chain variable domain which comprises a CDR1 region shown in SEQ ID NO: 23, a CDR2 region shown in SEQ ID NO: 24 and a CDR3 region shown in SEQ ID NO: 25;
(b) an antibody having the amino acid sequence shown in SEQ ID NO: 26 as the amino acid sequence of a H chain variable region (VH), and having the amino acid sequence shown in SEQ ID NO: 27 as the amino acid sequence of a L chain variable region (VL);

(c) a scFv (single chain variable fragment) antibody comprising the amino acid sequence shown in SEQ ID NO: 28.

In one embodiment of the pharmaceutical composition the MT4-MMP inhibitor and EGFR inhibitor comprised in said pharmaceutical composition are formulated separately to be used in the form of a kit where they are present together. In another embodiment of the pharmaceutical composition said pharmaceutical composition is formulated so that the MT4-MMP inhibitor and EGFR inhibitor are present in the same dosage form.

The present invention also provides the use of MT4-MMP antibody and EGFR antibody in the analysis of cancer tissue samples. In a preferred use the cellular distribution of EGFR is analyzed, and the presence or absence and/or the degree of the expression of MT4-MMP is detected. In particular, the analysis of the cellular distribution of EGFR is for detecting if EGFR is present intracellularly and/or membrane-associated. Further preferred, the use is for the prediction of the responsiveness of the cancer to anti-EGFR treatment. In a further preferred use said anti-MT4-MMP antibody and said anti-EGFR antibody are used simultaneously or on serial tissue sections of the same cancer tissue sample. In a further preferred embodiment of the use according to the present invention the cancer tissue sample is breast cancer tissue. Further preferred details and features of the breast cancer tissue were already described in this application.

The present invention further provides a method for the analysis of cancer tissue samples, comprising the steps of a) staining the cancer tissue sample with an anti-MT4-MMP antibody; b) staining the cancer tissue sample with an anti-EGFR antibody. In a preferred method steps a) and b) are carried out simultaneously or on serial tissue sections of the same cancer tissue sample. In a further preferred embodiment, the method for the analysis of cancer tissue samples further comprises the step of judging or measuring the degree of the expression of MT4-MMP and the localization of EGFR.

In particular, in a preferred method the cellular distribution of EGFR is analyzed, and the presence or absence and/or the degree of the expression of MT4-MMP is detected. Further preferred, the analysis of the cellular distribution of EGFR is for detecting if EGFR is present intracellularly and/or membrane-associated. In addition, the method allows the prediction of the responsiveness of the cancer to anti-EGFR treatment.

It is particularly preferred, that the method further comprises the step of distinguishing at least the following cancer cell types from each other:

i) MT4-MMP is highly expressed in cancer cells, EGFR is found intracellularly possibly with some labelling at the cell membrane;

ii) MT4-MMP is absent or present at low levels in cancer cells; EGFR is mainly localized at the cell membrane.

In a further preferred embodiment of the method the cancer tissue is breast cancer tissue. Further preferred details and features of the breast cancer tissue were already described in this application.

In the prior art methods for analysis of tumor tissue samples, EGFR expression is mainly searched at the epithelial cell surface. However, when carrying out the studies on which the present invention is based, the present inventors found a functional link between MT4-MMP and EGFR in tumor xenografts and in cell based assays. The presence of EGFR in the cytoplasm is likely reflecting its increased activation, signaling, turnover and internalization in the cancer cells, in particular breast cancer cells. Increased EGFR activation and signaling are known to stimulate cancer cell proliferation and tumor malignancy. Thus, increased cytoplasmic localization EGFR activity in the presence of MT4-MMP in human cancers is likely linked to a malignant cancer phenotype that could correlate with a poor patient outcome.

The present invention also provides a method of treatment of cancer comprising the administration of a subject in need thereof an effective dose of MT4-MMP inhibitor and EGFR inhibitor, wherein said MT4-MMP inhibitor and said EGFR inhibitor are administered simultaneously, sequentially or separately.

Membrane-type matrix metalloproteinases (MT-MMPs) have been implicated in numerous tissue remodeling processes associated to cancer invasion. MT4-MMP (MMP-17) is a glycosylphosphatidyl inositol (GPI) anchored MMP produced by breast cancer cells that promotes tumor vascularization and metastases.

When carrying out the studies of the present invention the present inventors found by using in vivo xenografts and in vitro 3D multicellular spheroids embedded in Matrigel®, that MT4-MMP promotes tumor cell proliferation in vivo and in 3D matrix, but not in 2D-monolayer cultures. The present inventors screened by Western blot analyses oncogenic proteins putatively activated by MT4-MMP. Mechanistical studies were conducted by using pharmacological inhibitors and co-immunoprecipitation assays. The present inventors further found evidence that these mitogenic effects involve Retinoblastoma protein (Rb) phosphorylation, cyclin dependent kinases (CDK4) activation and EGFR signaling pathway. Further, MT4-MMP co-immunoprecipitates with EGFR and enhances its activation in response to TGFα and EGF. The mitogenic effect of MT4-MMP was inhibited by EGFR inhibitors, Rb signaling inhibitors and MMP inhibitor (BB94). Furthermore, in a immunofluorescence experiment, the inventors demonstrated that MT4-MMP co-localizes with EGFR in cancer cells. Moreover, the present inventors demonstrated that combination treatment with MT4-MMP inhibitor and EGFR inhibitor is more efficient than the single inhibition of MT4-MMP or EGFR in respect to inhibition of breast cancer cell proliferation. The present inventors also showed interaction of MT4-MMP with EGFR in three cancer cell lines (MDA-MB231, BT549 and A431 cells). These interactions were demonstrated by the increase of EGFR phosphorylation observed in the presence of its ligands when MT4-MMP is expressed at the cell surface.

In summary, the present inventors identified for the first time an outside-in signaling involving MT4-MMP and established an expected functional link between MT4-MMP and EGFR. In the present invention an unexpected crosstalk between an MMP (namely MT4-MMP) and EGFR surprisingly was recognized as a key driver of breast cancer cell biology.

FIGURES LEGENDS

FIG. 1 shows that MT4-MMP expression promotes cell proliferation in tumors. Control cells (CTR) and MT4-MMP expressing cells (MT4-MMP) were s.c. injected into Rag1 −/− mice. Mice were sacrificed at day 21. (A) Tumor volume. (B) Immunohistochemistry detection of proliferating cells on tumor sections by double immunostaining using human Ki-67 antibody (brown staining) and human vimentin antibody (red staining) (upper panels, primary image).

Images from stained sections were binarized to calculate the percentage of Ki-67 positive cells (brown color) among cells positive for vimentine (red color, lower panels, binary image). Results are expressed as the ratio of Ki-67 positive cells to vimentin positive cells (graph). Statistical analysis was performed using Mann-Whitney test with Prism 5.04 software (GraphPad, San Diego, Calif.). Pvalue: * $p<0.05$; ** $p<0.01$.

FIG. 2 shows that MT4-MMP induces Rb phosphorylation and cyclin-dependent kinase in tumors. Tumors induced by MT4-MMP and control cells in RGA1 −/− mice were harvested at day 21 and analyzed for the production cell proliferation regulators proteins, including Rb and its phosphorylated form at (S807-811), cyclins (-A, -D1, -D2, -D3 and E), cyclin-dependent kinases (CDK2, CDK4 and CDK6) and inhibitors (P15, P21 and P27). MT4-MMP tumors showed hyperphosphorylation of Rb and higher levels of cyclin D1, D3, E, CDK4 and P27. The triplicate loadings are from 3 different tumors out of 5 (n=5) and actin is used as a loading control. Data are those of three independent experiments (n=5). Right panels are the densitometry quantification of western blot data generated from three independent experiments. Statistical analysis was performed using Mann-Whitney test with Prism 5.04 software (GraphPad, San Diego, Calif.). P-value:* $p<0.05$; ** $p<0.01$.

Figure 3:
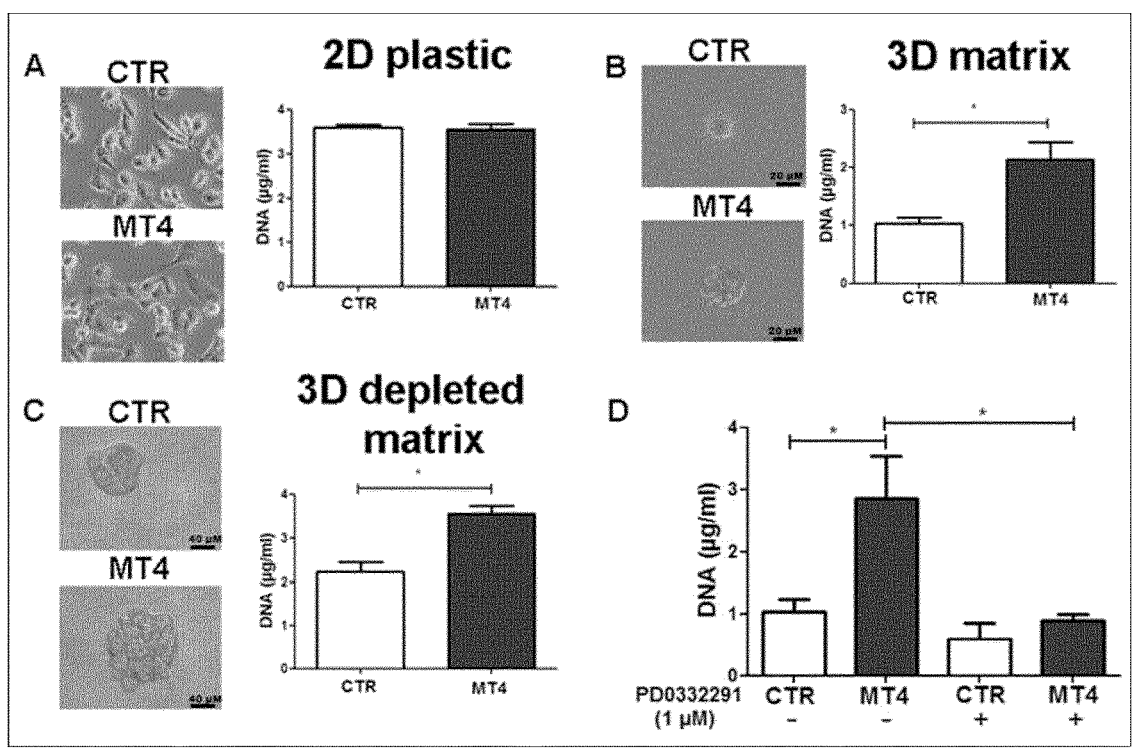
Figure 4A:
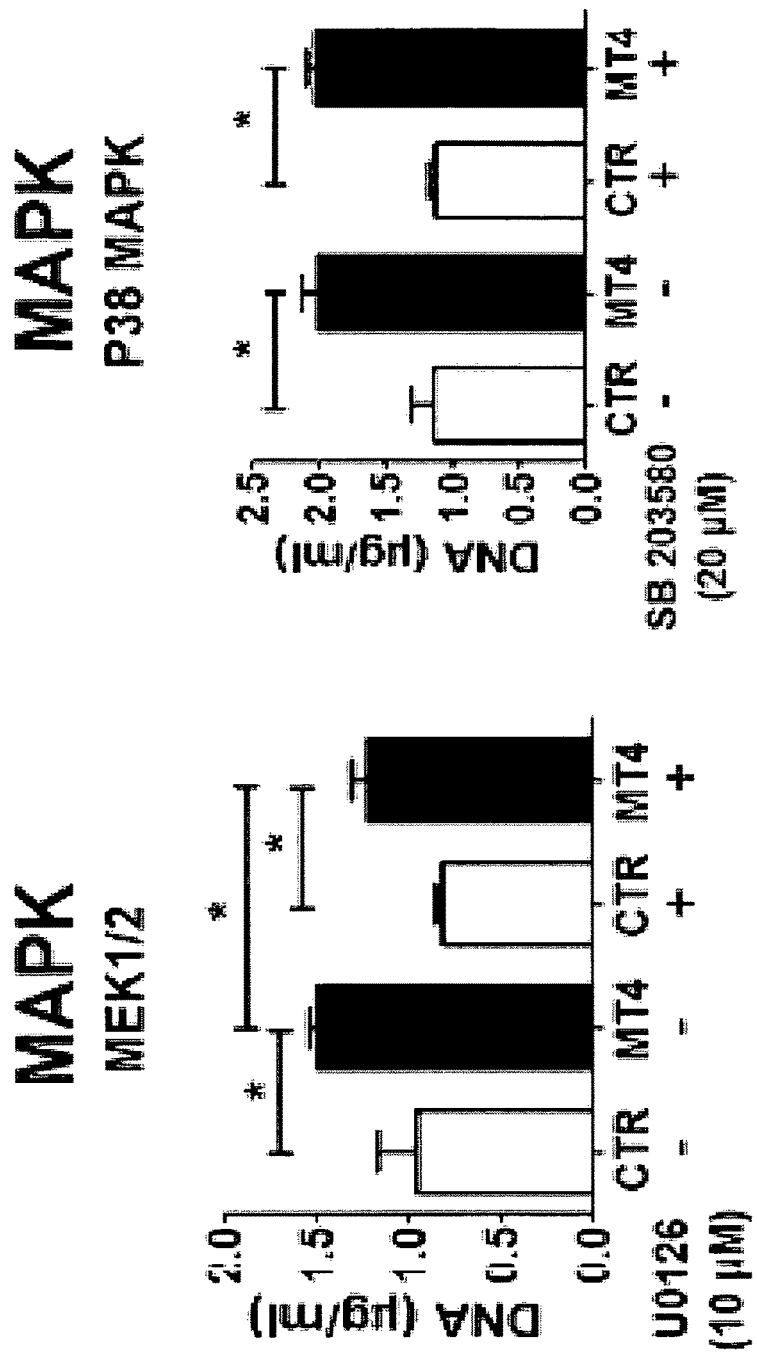
Figure 4B:
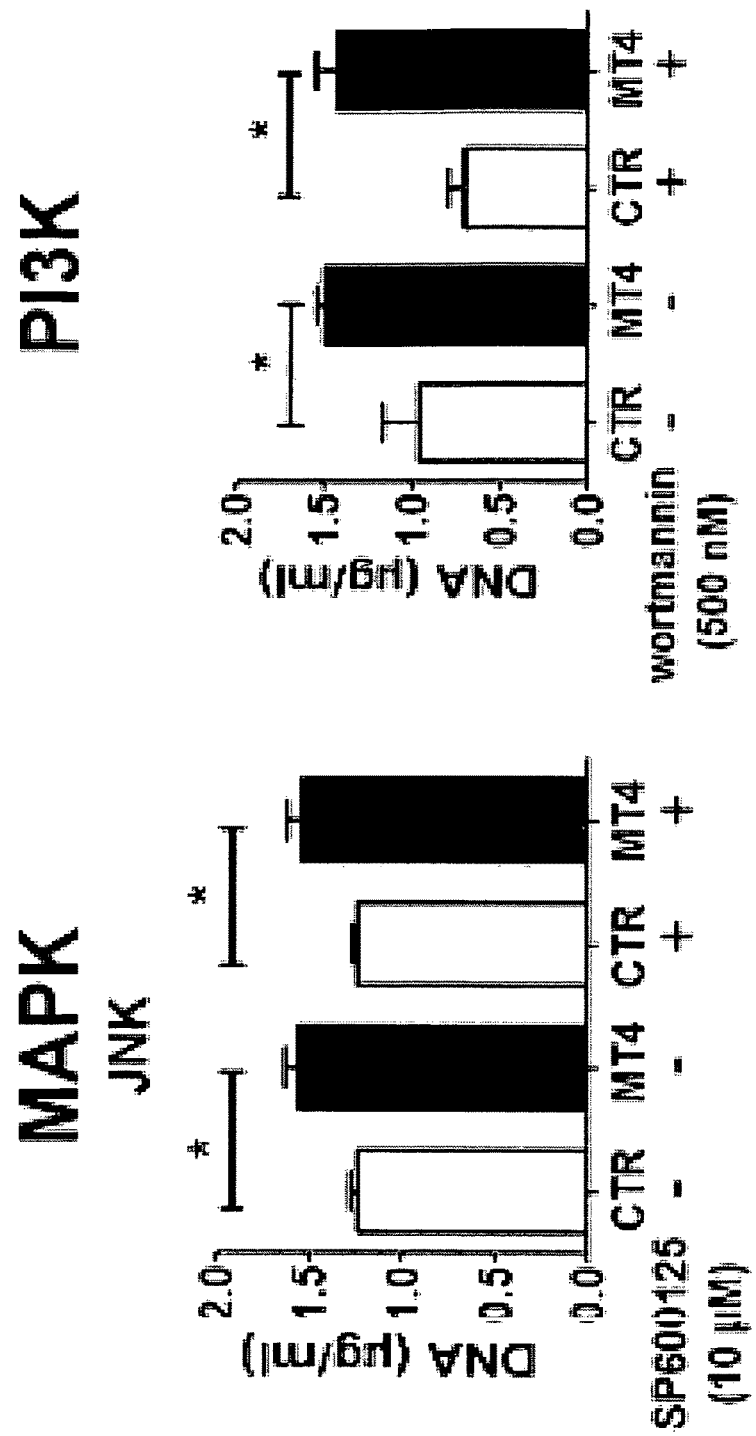
Figure 4C:
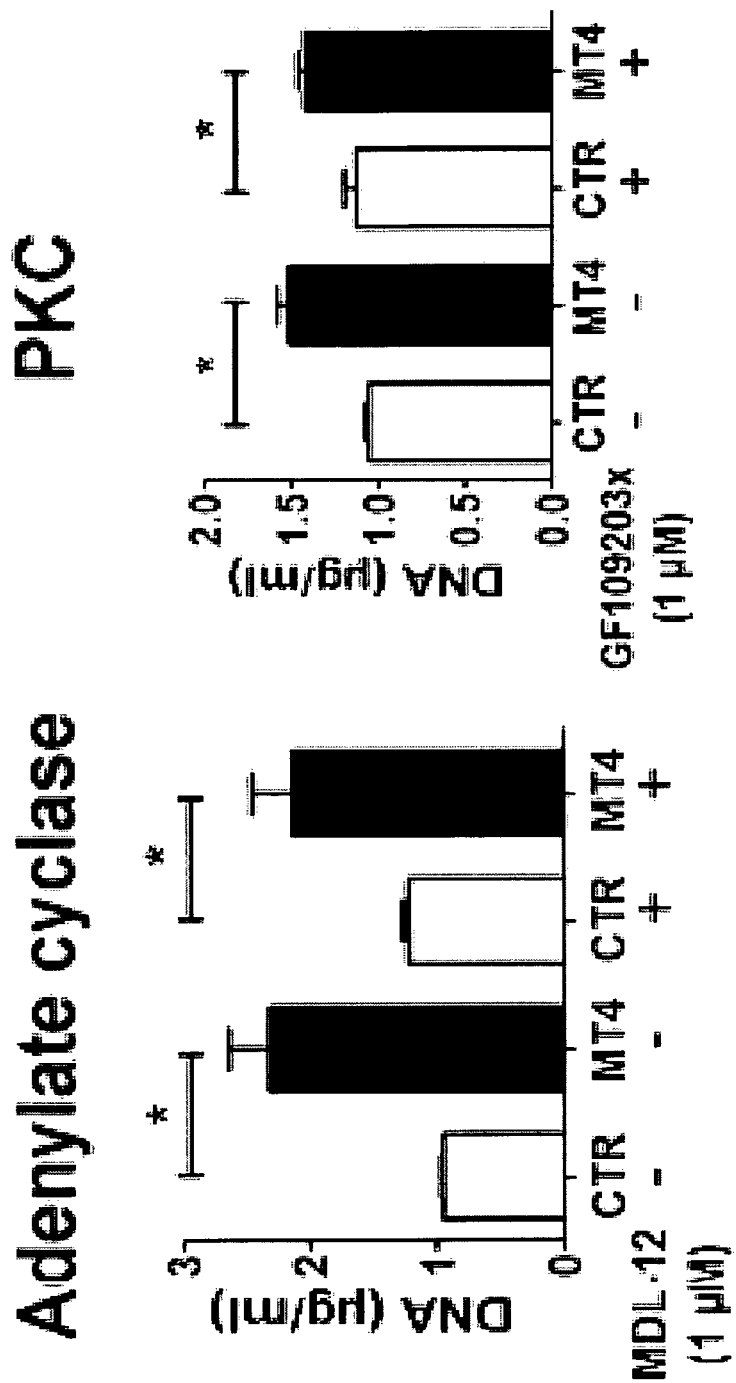
Figure 4D:
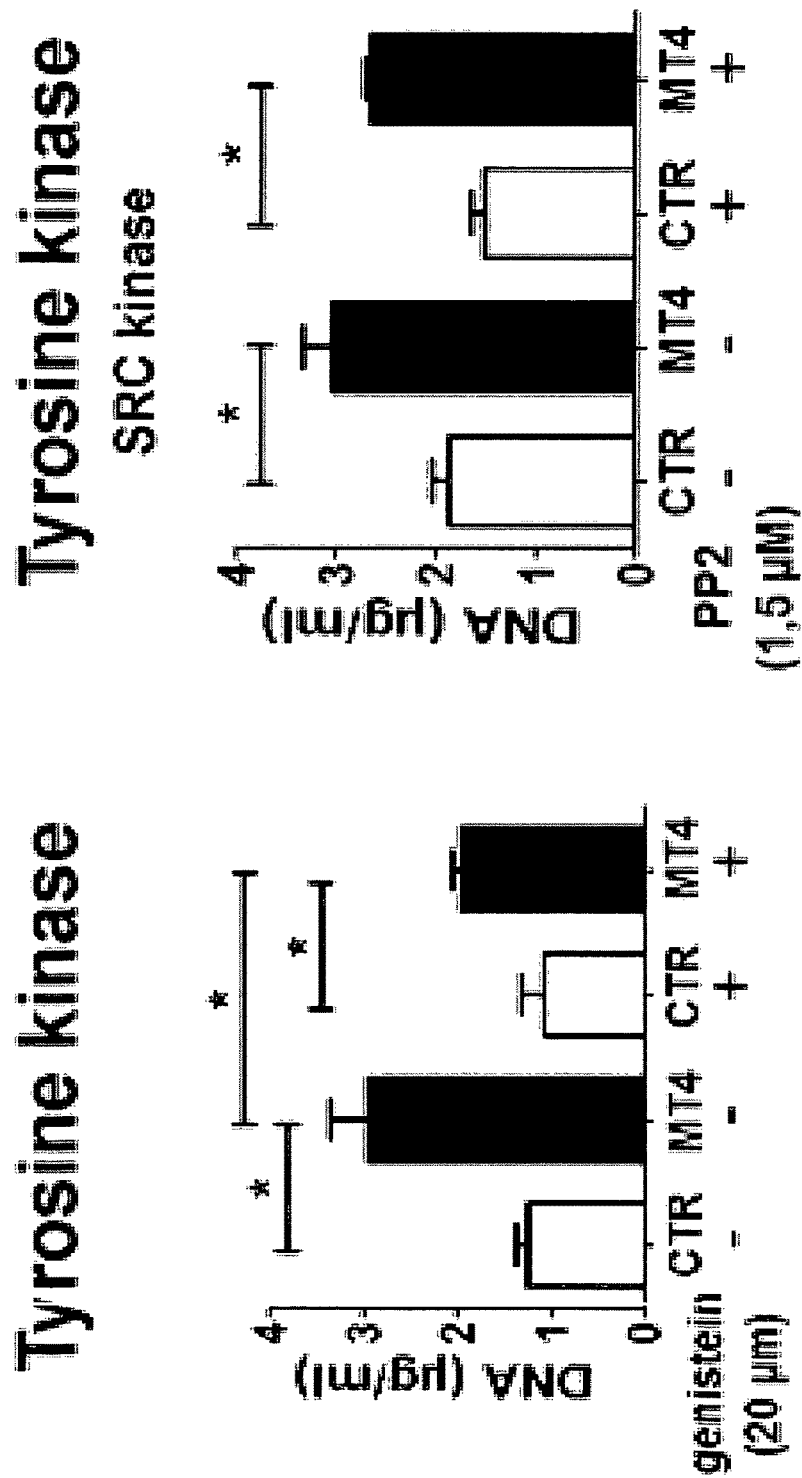
Figure 4E:
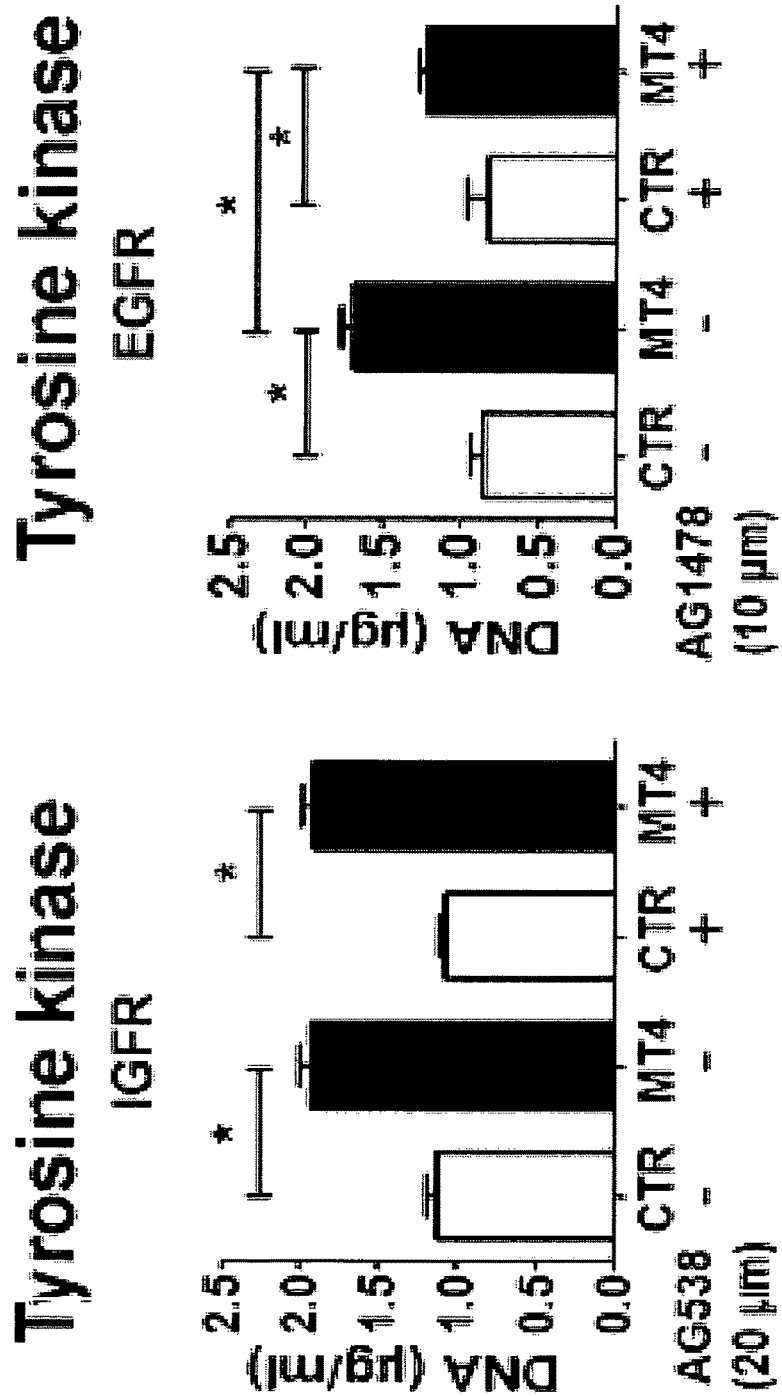

FIG. 3 shows that MT4-MMP induces cell proliferation in 3D culture matrix. MDA-MB231 cells transfected with MT4-MMP (MT4) or control vector (CTR) were incubated in 2D plastic dish (A), in 3D Matrigel® matrix (B) or in growth factor-free 3D Matrigel® "3D depleted matrix" (C). Representative image of cell culture are shown on the left (original magnification 20×). Cell proliferation was assessed by titrating DNA quantity (μg/ml) (graphs). Cells were incubated in the 3D Matrigel® matrix in the presence of CDK4 inhibitor (PD0332991) (D). Data are those of three independent experiments. Statistical analysis was performed using Mann-Whitney test with Prism 5.04 software (GraphPad, San Diego, Calif.). P-value: * $p<0.05$; ** $p<0.01$.

FIG. 4 shows that MT4-MMP-dependent mitogenic effect is dependent on tyrosine kinase activity and EGFR signaling. MDA-MB 231 cells expressing MT4-MMP (MT4) and control (CTR) cells were incubated in 3D Matrigel® matrix in the presence or not of several inhibitors of signaling pathways including MAPK, PI3K, adenylate cyclase, PKC and tyrosine kinase. Cell proliferation was assessed after 7 days of incubation. Results are expressed as DNA content (μg/ml). Data are those of three independent experiments. Statistical analysis was performed using Mann-Whitney test with Prism 5.04 software (GraphPad, San Diego, Calif.). Pvalue: * $p<0.05$; ** $p<0.01$.

Figure 5:
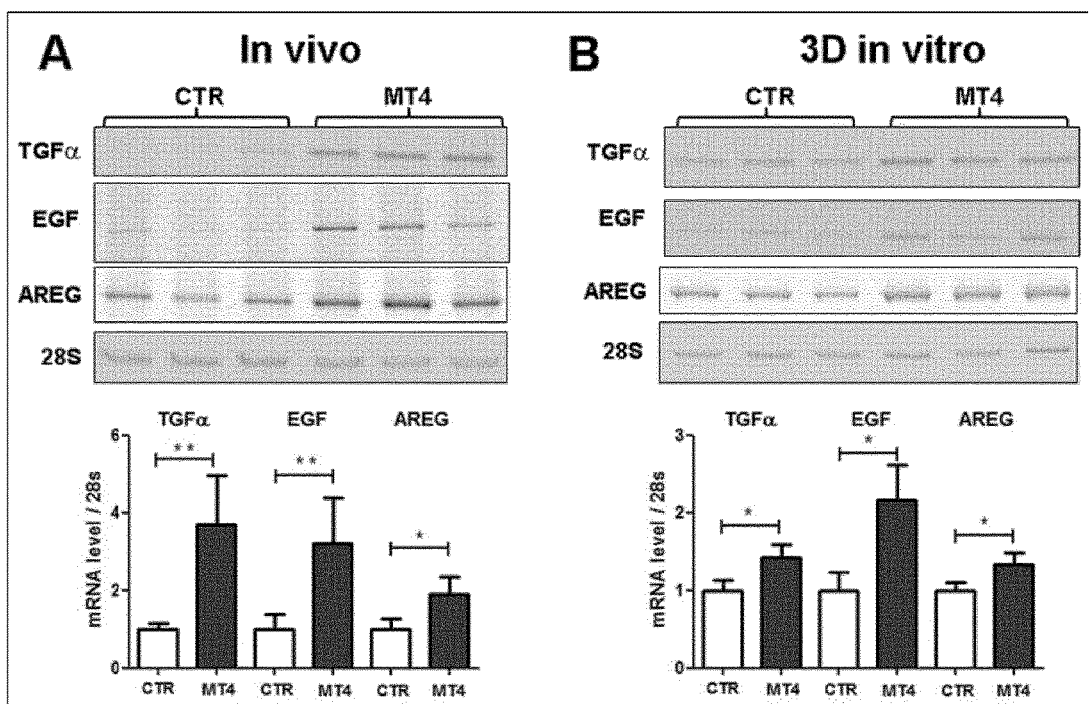

FIG. 5 shows that MT4-MMP promotes EGFR ligand expression in tumors and in 3D culture model. RT-PCR analysis of EGFR ligands in MT4-MMP expressing tumors (MT4) and control (CTR) tumors in vivo (A) and in vitro the 3D culture model (B). Graphs correspond to the densitometric quantification of the RT-PCR analysis showing a significant increase of EGFR ligand mRNA in MT4-MMP tumors and spheroids. Data are those of three independent experiments. Statistical analysis was performed using Mann-Whitney test with Prism 5.04 software (GraphPad, San Diego, Calif.). P-value: * $p<0.05$; ** $p<0.01$.

Figure 6:
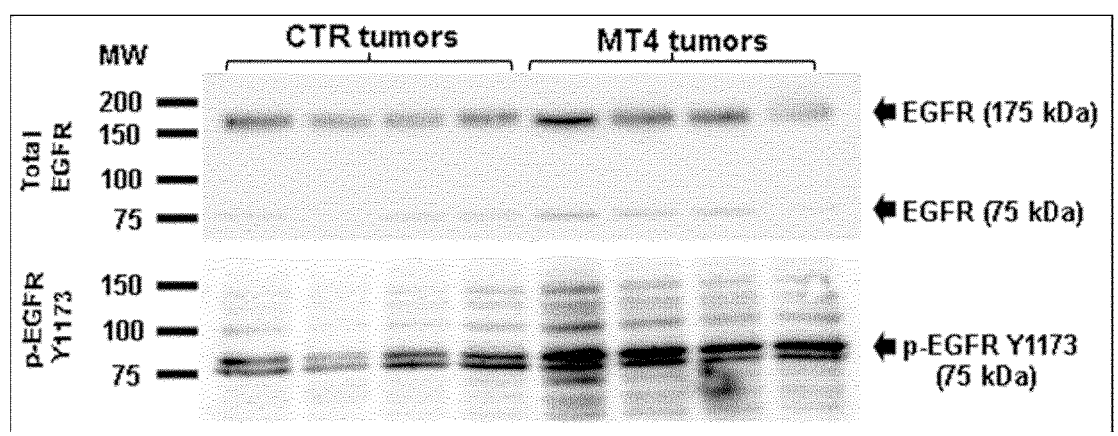

FIG. 6 shows that MT4-MMP promotes EGFR phosphorylation in tumors. MT4-MMP (MT4) and control (CTR) tumor extracts were analyzed by western blot for EGFR (upper panel) and its phosphorylated form at Y1173 (lower panel).

Figure 7:
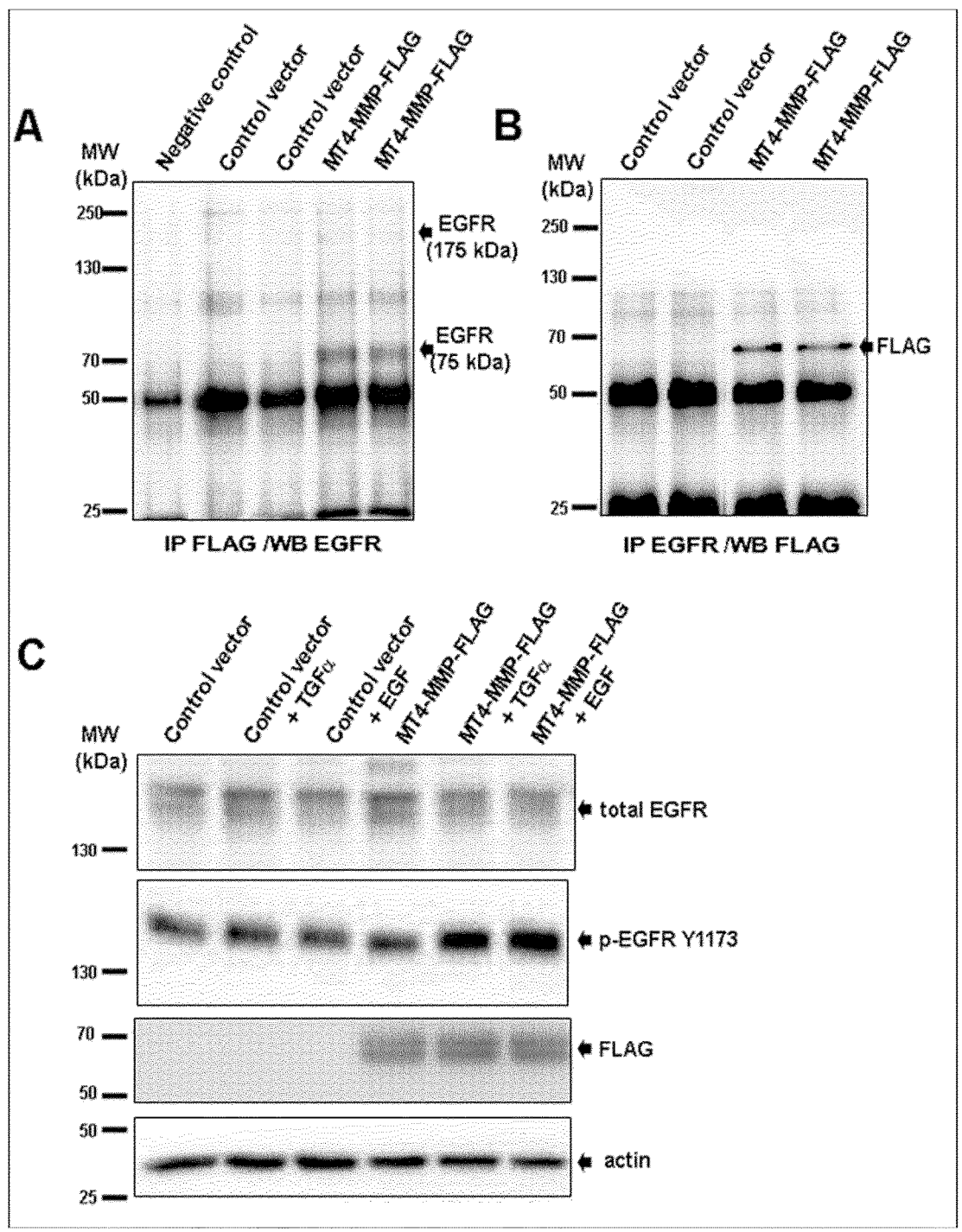

FIG. 7 shows that MT4-MMP interacts with EGFR and promotes its activation through ligand binding. Total cell lysates from COS-1 cells transfected with an empty vector (control vector) or a vector containing MT4-MMP cDNA with a FLAG-tag insertion sequence in the hinge region of the enzyme (MT4-MMP-FLAG) were immunoprecipitated with FLAG antibody prior to EGFR detection (A), EGFR was immunoprecipitated before MT4-MMP detection (B). COS-1 cells transfected with MT4-MMP or control vector were incubated with recombinant TGFα or EGF (C). EGFR, p-EGFR (Y1173) and MT4-MMP production were analyzed by western blot in total cell lysates. Actin is used as loading control for MT4-MMP western blot. Data are those of three independent experiments.

Figure 8:
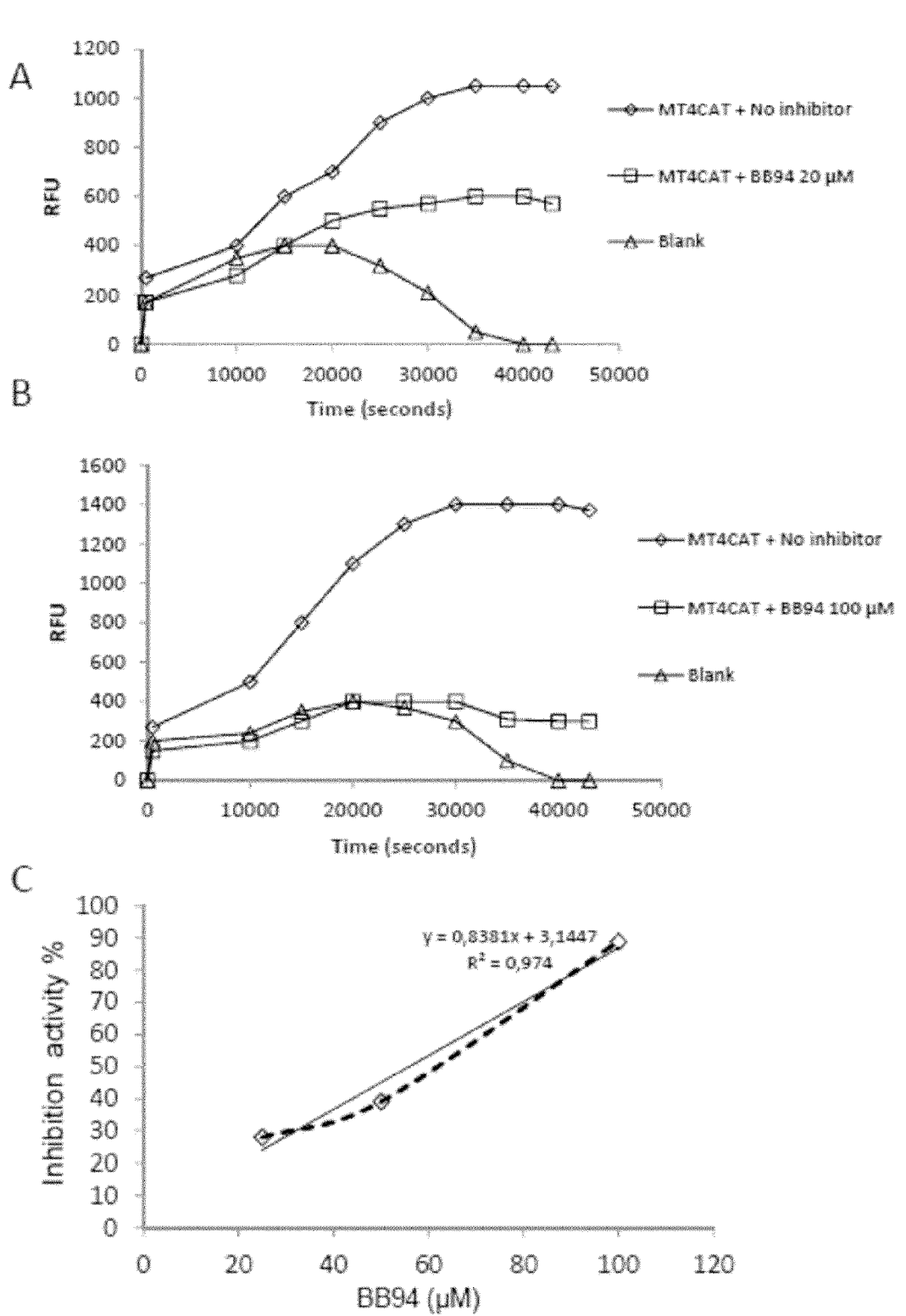

FIG. 8 shows the inhibition of the recombinant catalytic domain of MT4-MMP (MT4CAT) in the presence (20 μM and 100 μM) or absence of a broad spectrum MMP inhibitor BB94 (Batimastat) (FIGS. 8 A and B). A complete inhibition of MT4-MMP activity was achieved at 100 μM (FIG. 8 B). Panel C shows a dose-dependent effect of the inhibitor. This assay demonstrates the capacity of BB94 to inhibit MT4-MMP activity. The catalytic activity of the recombinant catalytic domain of MT4-MMP (MT4CAT) pre-incubated with fluorogenic substrate as described in example 17 was recorded in the presence of various levels of BB94 or no inhibitor (control). The inhibition of the activity was calculated as percentage to control (100% activity or 0% inhibition).

Figure 9:
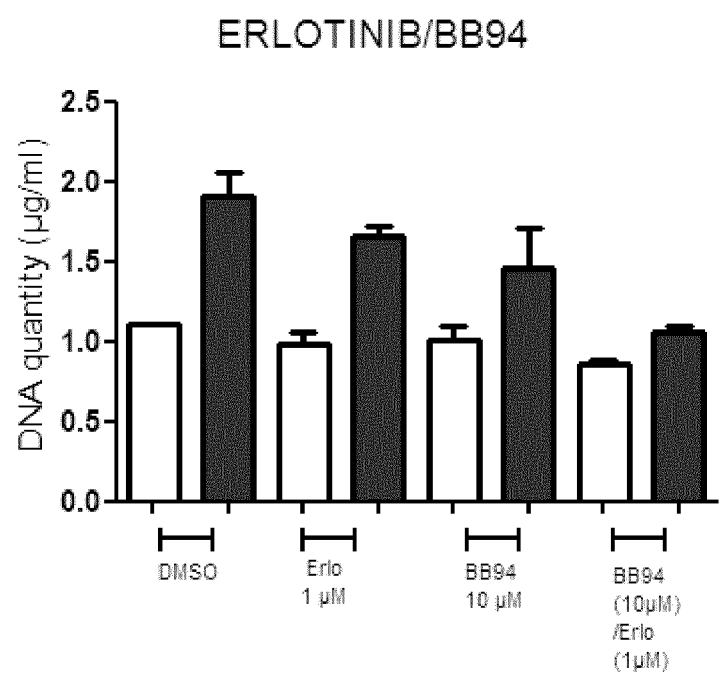

FIG. 9 shows the sensitization of cancer cells to EGFR inhibitor (erlotinib) treatment by using MT4-MMP inhibitor (BB94). MDA-MB 231 cells expressing MT4-MMP (MT4, black columns) and control (CTR, open columns) cells were incubated in 3D Matrigel® matrix in the presence or absence of BB94 and erlotinib. Cell proliferation was assessed after 7 days of incubation by DNA content quantification (μg/ml). The results show that the combined treatment of MT4-MMP inhibitor and EGFR inhibitor results in a stronger reduction of cell proliferation than single treatments.

Figure 10:
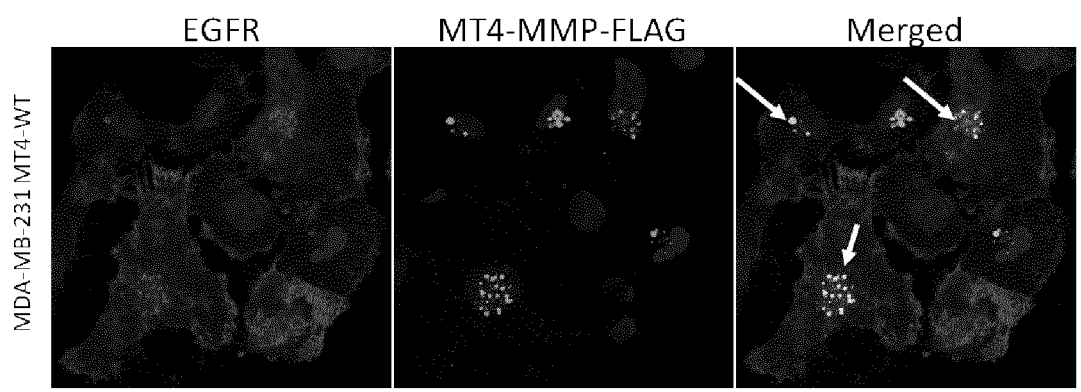

FIG. 10 shows the detection of MT4-MMP and EGFR co-localization in breast cancer cells by immunofluorescence and confocal microscopy. MDA-MB231 cells expressing MT4-MMP were cultured on cover slips and stained with a mouse anti-FLAG and a rabbit anti-EGFR antibodies, followed by secondary anti-mouse Alexa Fluor-488 for FLAG (green color) and anti-rabbit Alexa Fluor-546 (red color) for EGFR. Co-localization of MT4-MMP (middle panel) and EGFR (left panel) are shown as bright spots (arrows in merged image, right panel) at the cell surface and intracellularly.

Figure 11:
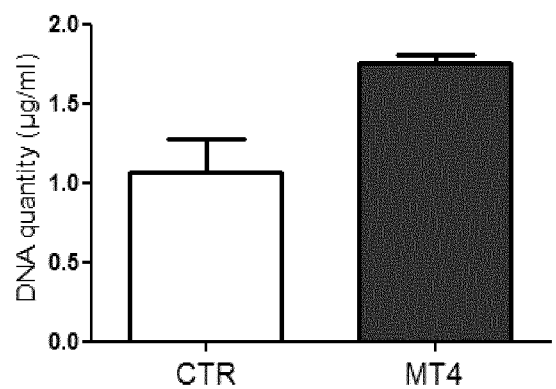
Figure 11:
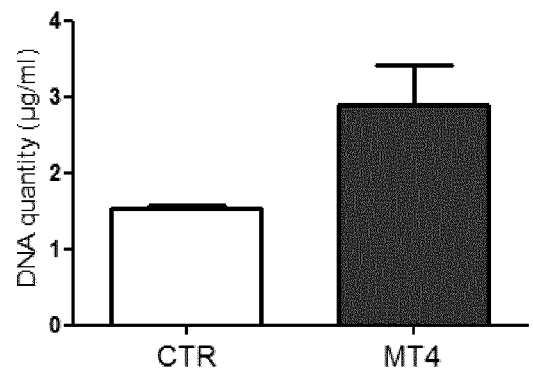

FIG. 11 shows that MT4-MMP induces cell proliferation in 3D matrix in other cell lines. Breast carcinoma BT549 cells and epidermoid A431 cells expressing MT4-MMP were generated by a stable transfection with MT4-MMP cDNA or control vector. Cell proliferation was assessed after 7 days of incubation in 3D Matrigel® and DNA content quantification. The results show that MT4-MMP expression in the different cell lines (MT4) is associated with a significant increase in cell proliferation when compared to control cells (CTR).

Figure 12:
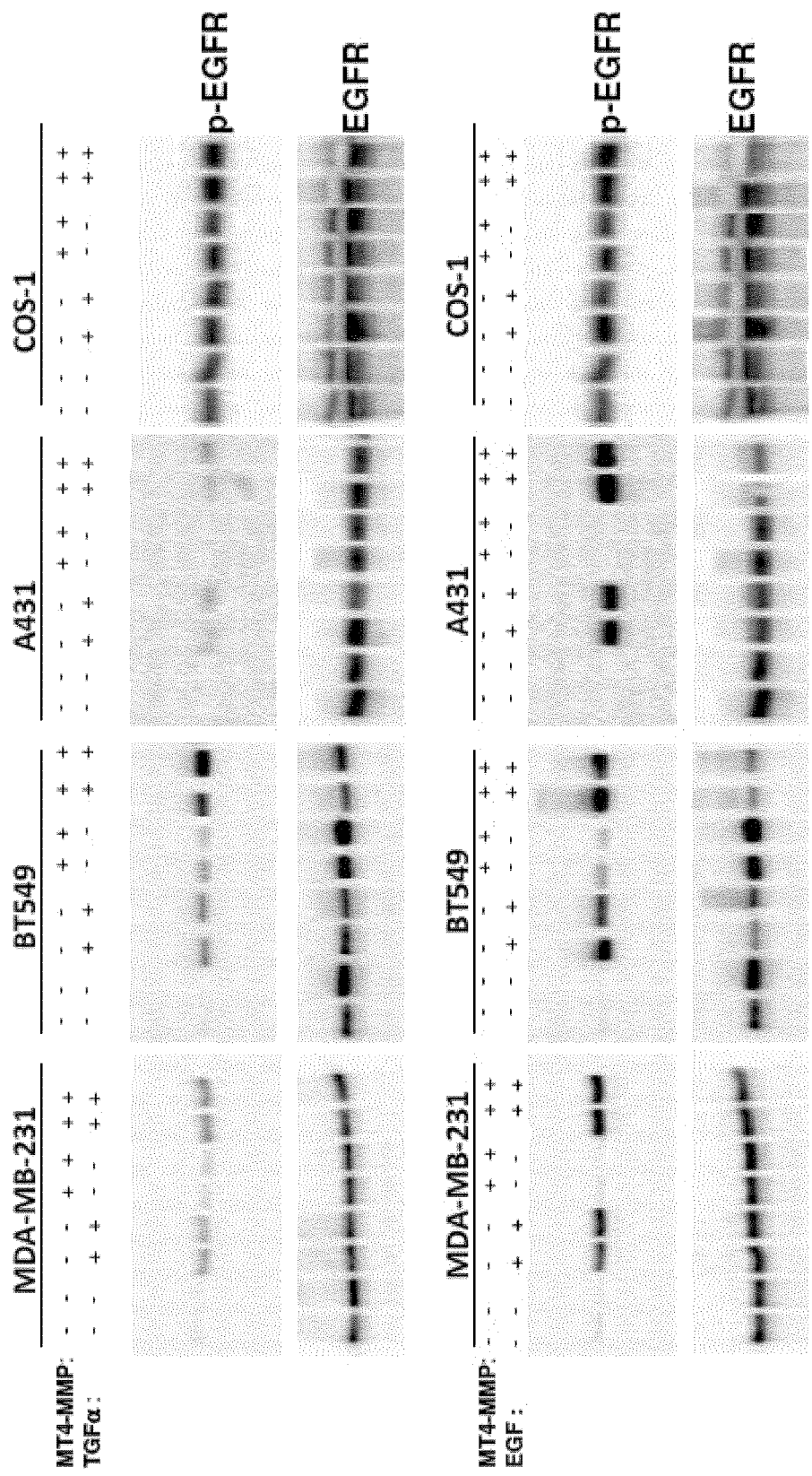

FIG. 12 shows the enhancement of EGFR phosphorylation in the presence of MT4-MMP. Cells were stimulated or not with recombinant pro-TGFα or EGF and EGFR phosphorylation status was analyzed by western blot using antibodies raised against phospho-EGFR and total EGFR. Cell incubation with EGFR ligands induced EGFR phosphorylation in either cells expressing or not MT4-MMP. EGFR phosphorylation in response to ligands was more pronounced in the presence of MT4-MMP in MDA-MB231, BT549, A431 and COS-1 cells. This data demonstrates a functional role of MT4-MMP in promoting EGFR activation and signaling.

Figure 13:
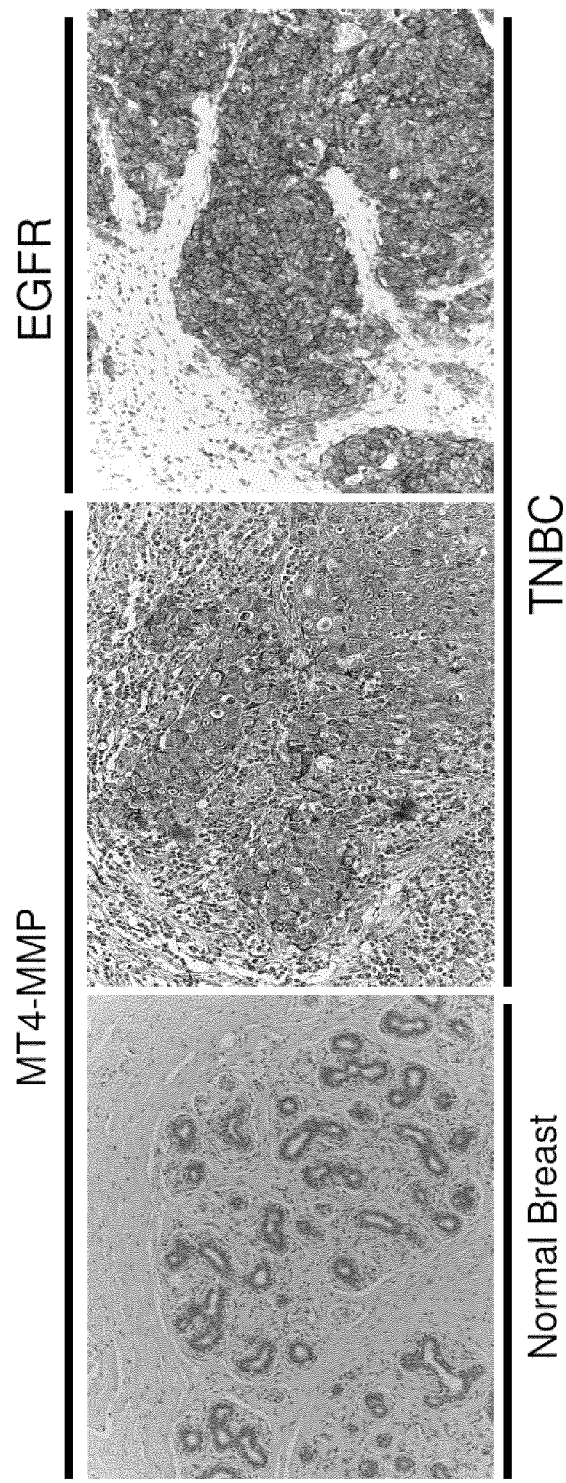
Figure 14A:
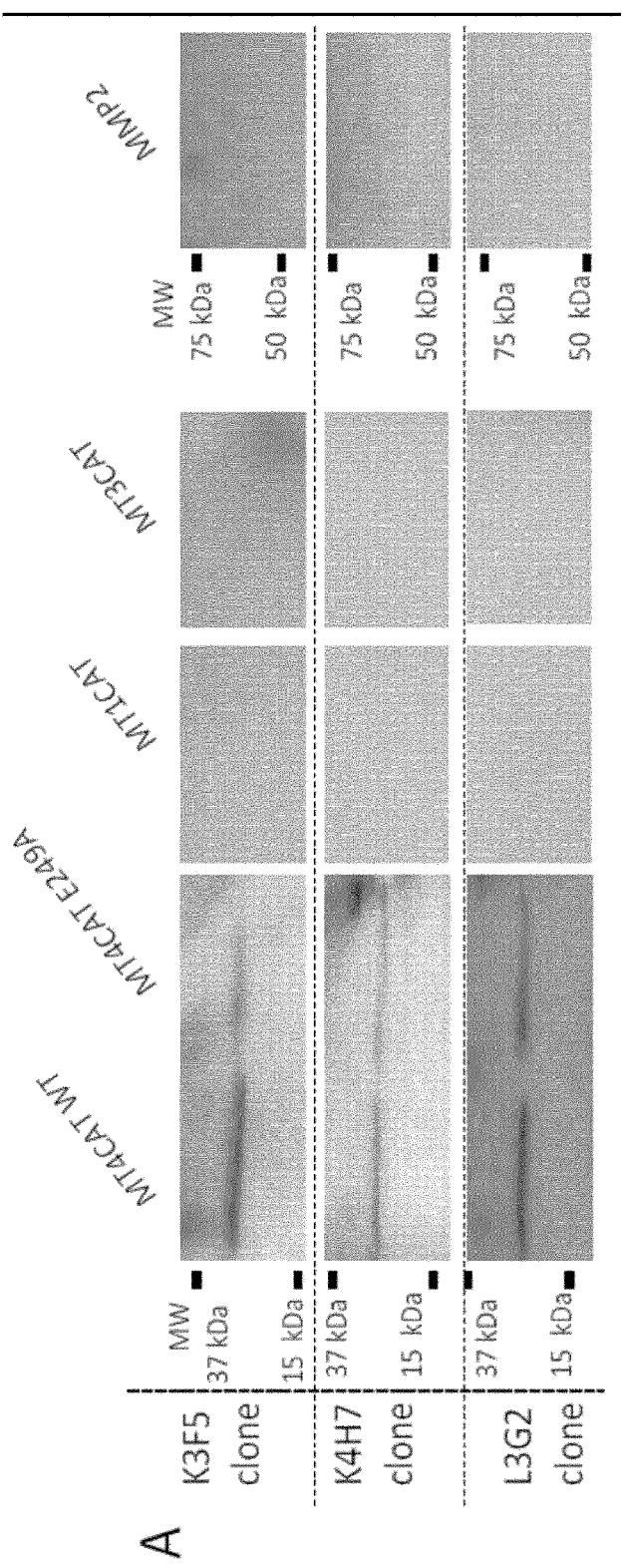
Figure 14B:
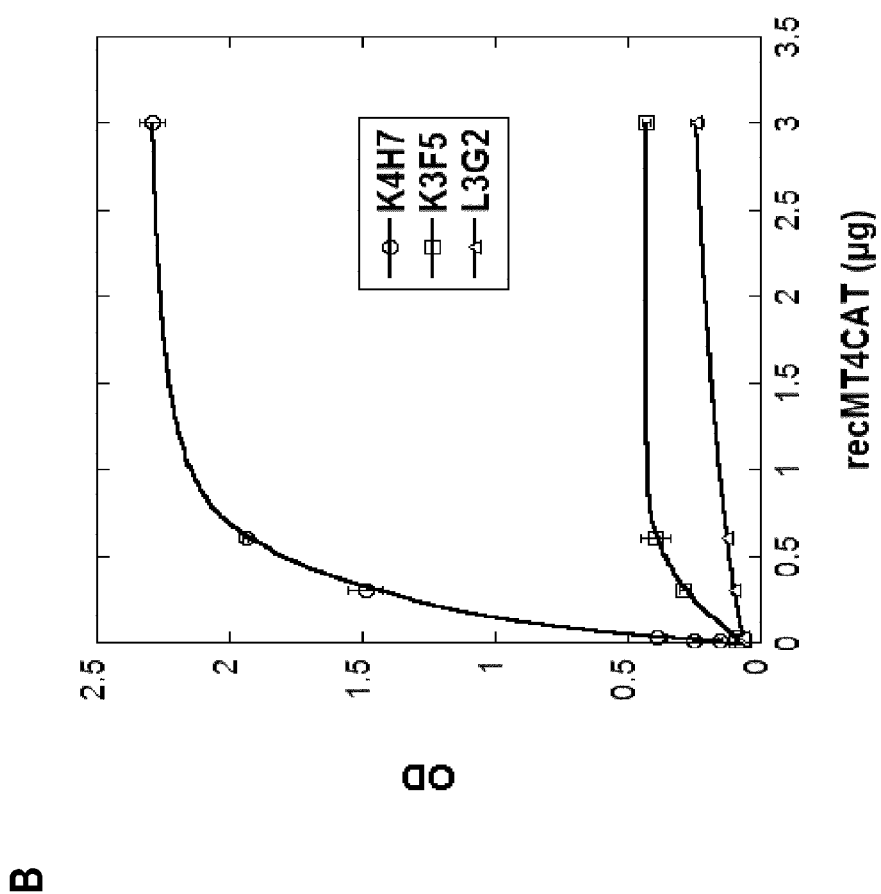
Figure 14C:
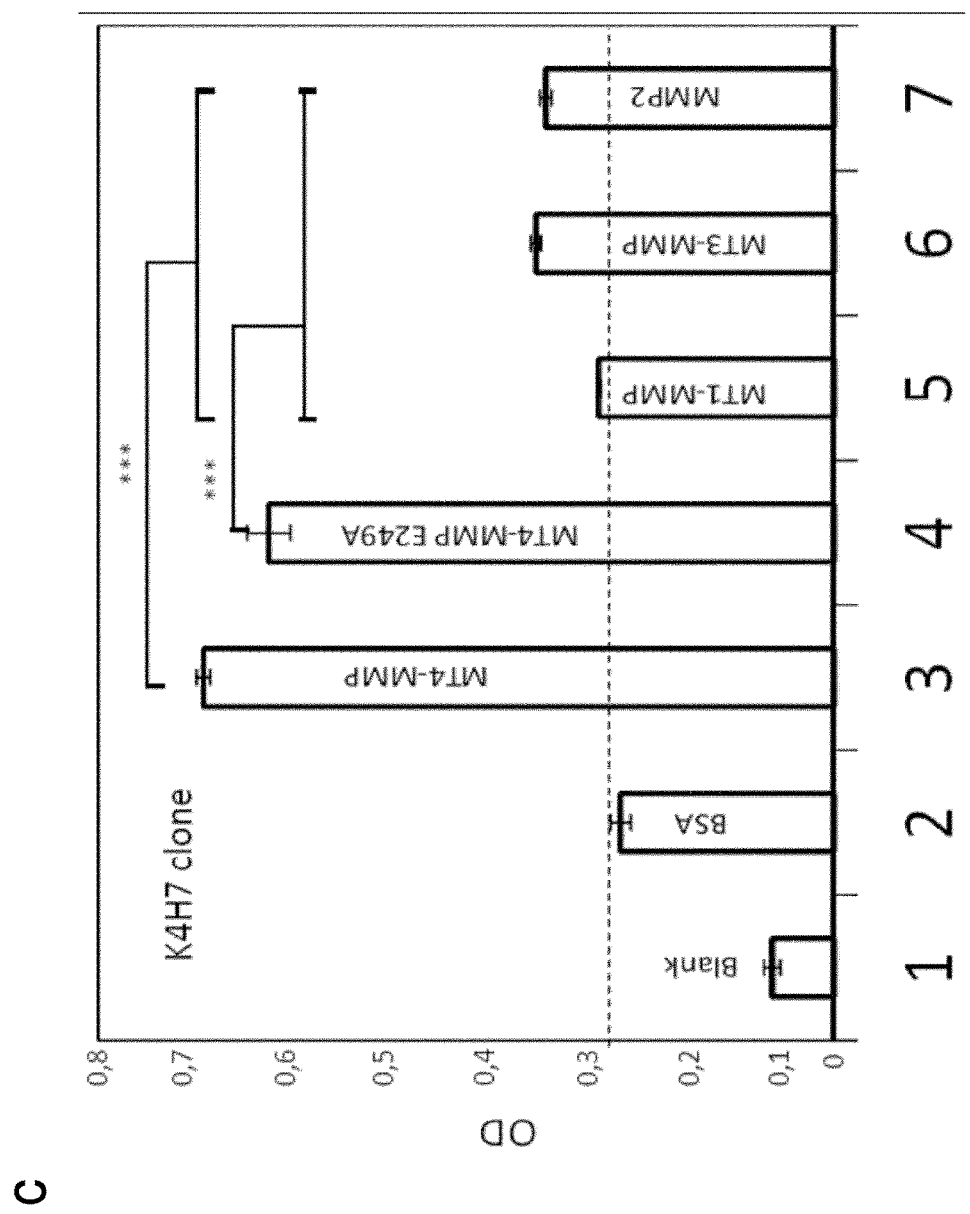
Figure 14D:
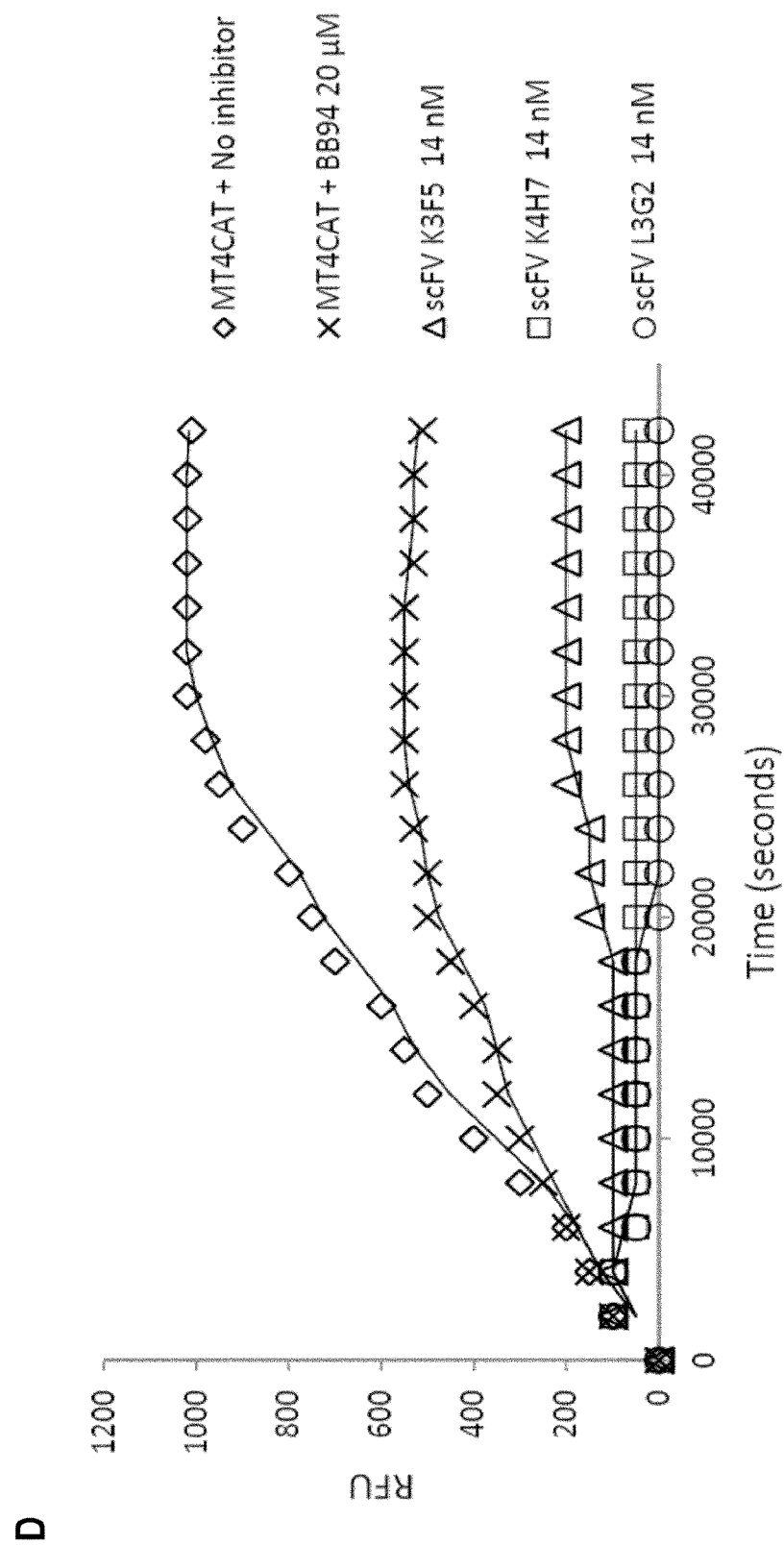

FIG. 13 shows that MT4-MMP and EGFR are expressed in human triple negative breast cancer (TNBC). Immunohistochemical staining for MT4-MMP in normal breast tissues and TNBC sections show that MT4-MMP expression is mainly localized in cancer cells in the TNBC but not in normal tissue. Similarly, EGFR expression is increased in the tumor compartment of TNBC.

FIG. 14 shows the biochemical characterization of the three scFV antibodies (K3F5, L3G2 and K4H7) to MT4-MMP. A) Antibody specificity assessed by Western blot. Recombinant MT4-MMP, its E249A mutant and the catalytic domains of further MMPs were incubated with purified scFV clones that contain a myc tag. The bound antibody was detected with mouse anti-myc antibody followed by incubation with HRP-conjugated anti-mouse antibody. After adding TMB substrate, the absorbance was measured at 450 nm. B) Antibody affinity. Recombinant MT4-CAT protein and BSA (background) was immobilized on 96 well-plates, followed by non-specific blockage. The bound antibody was detected as described for panel A. The K4H7 clone displayed the highest affinity for recombinant MT4-MMP. C) Specificity of K4H7 antibody evaluated by ELISA. The specificity for MT4-MMP was determined by incubating the antibody with of recombinant wild-type MT4-MMP (column 3), inactive mutated form of MT4-MMP (E249A) (column 4) and other recombinant MMPs (column 5: MT1-MMP; column 6: MT3-MMP; column 7: MMP2). BSA (column 2) and the absence of protein (column 1: blank) were used as control. K4H7 clone binds specifically to MT4-MMP and its inactive form, but not to MT1-MMP, MT3-MMP and MMP2 catalytic domains. Similar results were obtained with the clone K3F5. D) Neutralizing capacity of antibodies. The enzymatic activity of the recombinant catalytic domain of MT4-MMP (MT4CAT) was monitored by the cleavage of quenched fluorogenic peptide substrate pro-tumor necrosis factor-α converting enzyme (TACE) and using Luminescence spectrometer as described in example 17. The substrate was incubated with MT4CAT. The cleavage of quenched fluorogenic peptide was monitored by measuring relative fluorescence units (RFU) during the incubation time (seconds) in the absence of inhibitor (MT4CAT+No inhibitor) or in the presence of BB94 (20 µM) or of the scFV clones (14 nM). MT4-MMP enzymatic activity was inhibited completely with the three scFV clones.

Figure 15:
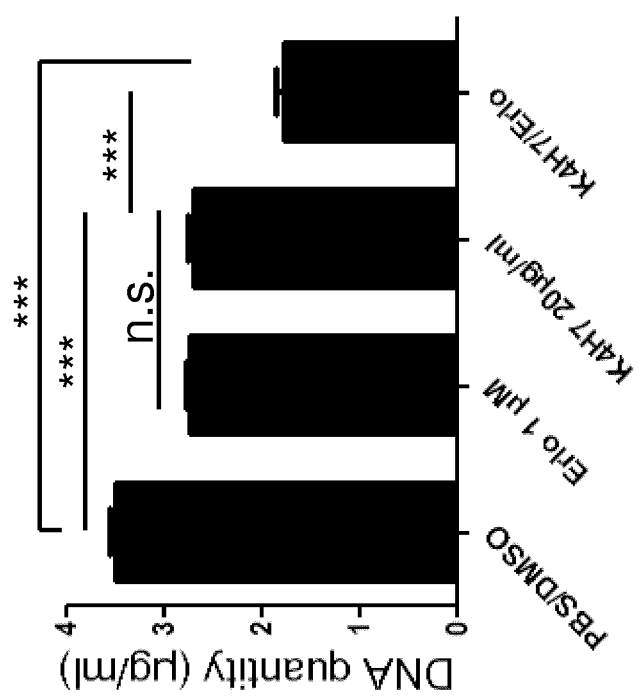

FIG. 15 shows the sensitization of cancer cells to EGFR inhibitor (erlotinib) treatment by using MT4-MMP blocking antibody. MDA-MB 231 cells expressing MT4-MMP were incubated in 3D Matrigel® matrix in the presence or absence (PBS/DMSO) of MT4-MMP blocking antibody (K4H7 clone) at the concentration of 20 µg/ml and erlotinib (Erlo) at 1 µM. Cell proliferation was assessed after 7 days of incubation by DNA content quantification (µg/ml). The results show that the combined treatment of MT4-MMP blocking antibody and EGFR inhibitor results in a stronger reduction of cell proliferation than single treatments.

Figure 16:
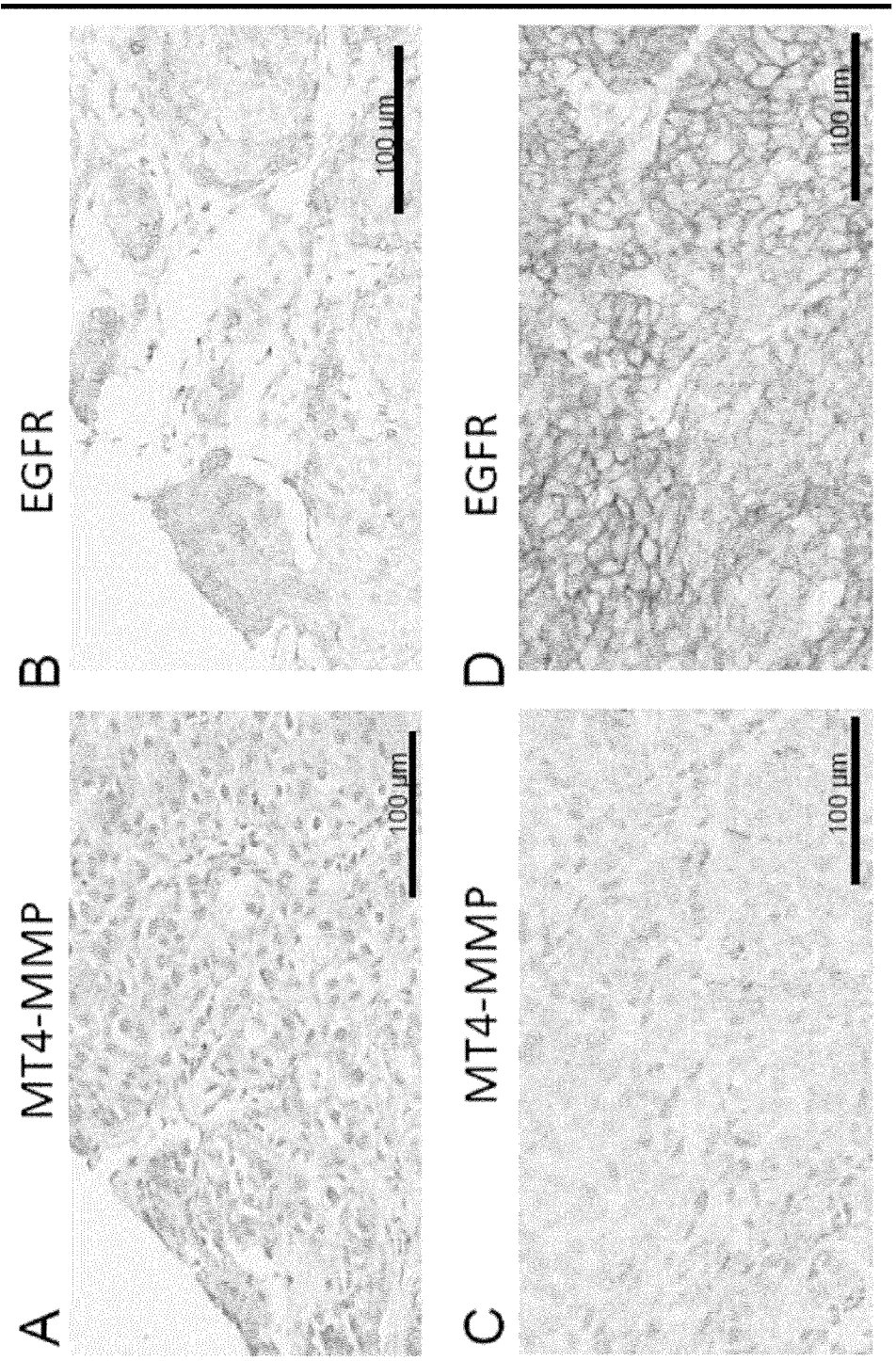

FIG. 16 shows immunohistochemical staining of MT4-MMP and EGFR of two different human breast cancer samples (A/B versus C/D). Serial sections (A/B and C/D) were used. A-B: high MT4-MMP production (A) and cytoplasmic localization of EGFR (B). C-D: low MT4-MMP detection (C) and membrane localization of EGFR (D).

FIG. 17 shows the VH (heavy chain) amino acid sequence (SEQ ID NO: 26) and VL (light chain) amino acid sequence (SEQ ID NO: 27) of the K4H7 scFv antibody of the present invention, which specifically binds to MT4-MMP. The figure indicates the hypervariable regions (CDR1, CDR2 and CDR3) which are embedded within the scaffold FW1-FW4 (FW: framework) of heavy and light chain variable region. The hypervariable regions CDR1, CDR2 and CDR3 are also shown in the sequence listing (heavy chain: CDR1: SEQ ID NO: 20; CDR2: SEQ ID NO: 21; CDR3: SEQ ID NO: 22; light chain: CDR1: SEQ ID NO: 23; CDR2: SEQ ID NO: 24; CDR3: SEQ ID NO: 25). The complete scFv antibody as used in the examples has the amino acid sequence shown in SEQ ID NO: 28.

DETAILED DESCRIPTION OF THE PRESENT INVENTION

The present invention provides a new combination treatment for cancer, wherein MT4-MMP inhibitor and EGFR inhibitor are administered simultaneously, sequentially or separately.

Definitions

As used herein, MT4-MMP inhibitor is an active agent which selectively decreases or blocks the activity of MT4-MMP. For testing if MT4-MMP is inhibited an enzymatic assay is carried out using a recombinant form of MT4-MMP and a fluorogenic peptide as substrate, such as for instance Mca-(endo-1a-Dap(Dnp))-TNF-α (−5 to +6) amide (human) (M-2255, Bachem AG, Switzerland). After immobilization of said peptide this substrate will be brought into contact with MT4-MMP, which will cleave this peptide resulting in a release of a fluorogenic fragment of said peptide, which can be detected and measured. In the presence of an effective inhibitor the cleavage of the peptide and release of the fluorogenic peptide fragment will be reduced or blocked, thereby indicating the inhibiting activity of said inhibitor. In another test an in vitro proliferating assay is carried out using cells expressing MT4-MMP. Overexpression of MT4-MMP increases cell proliferation. In the presence of an effective inhibitor the increase of cell proliferation or cell proliferation as such will be reduced or blocked thereby indicating the inhibiting activity of said inhibitor.

As used herein, MT4-MMP (Membrane-type matrix metalloproteinases, also named MMP17) is a glycosylphosphatidyl inositol (GPI) anchored MMP having amino acid sequence shown in SEQ ID NO: 1. Said MT4-MMP inhibitor may be a monoclonal or polyclonal antibody specifically binding to MT4-MMP, an anti-sense nucleic acid or chemical analogue thereof specifically hybridizing to MT4-MMP mRNA, a chemical compound, fragment of MT4-MMP.

The epidermal growth factor receptor (EGFR; ErbB-1; HER1 in humans) is the cell-surface receptor for members of the epidermal growth factor family (EGF-family) of extracellular protein ligands. EGFR (epidermal growth factor receptor) exists on the cell surface and is activated by binding of its specific ligands, including epidermal growth factor (EGF), transforming growth factor α (TGFα), HB-EGF, amphiregulin, betacellulin, epigen, epiregulin. The epidermal growth factor receptor is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4). Mutations affecting EGFR expression or activity can result in cancer.

Upon activation by its growth factor ligands, EGFR undergoes a transition from an inactive monomeric form to an active homodimer. In addition to forming homodimers after ligand binding, EGFR may pair with another member of the ErbB receptor family, such as ErbB2/Her2/neu, to create an activated heterodimer. EGFR dimerization stimulates its intrinsic intracellular protein-tyrosine kinase activity. As a result, autophosphorylation of several tyrosine (Y) residues in the C-terminal domain of EGFR occurs. These include Y992, Y1045, Y1068, Y1148 and Y1173. This autophosphorylation elicits downstream activation and signaling by several other proteins that associate with the phosphorylated tyrosines through their own phosphotyrosine-binding SH2 domains. These downstream signaling proteins initiate several signal transduction cascades, principally the MAPK, Akt and JNK pathways, leading to DNA synthesis and cell proliferation. These downstream proteins modulate phenotypes such as cell migration, adhesion, and proliferation. Activation of the receptor is important for the innate immune response in human skin. The kinase domain of EGFR can also cross-phosphorylate tyrosine residues of other receptors it is aggregated with, and can itself be activated in that manner.

EGFR-Positive Cancer

According to a preferred embodiment of the present invention, the cancer to be treated by the combination treatment is EGFR-positive cancer. In clinic, EGFR-positive cancer currently are determined by immunohistochemistry. This technique measures the presence of EGFR protein only. EGFR-positive cancers are detected by immunohistochemical staining. For staining routinely-fixed, paraffin-embedded specimens are used. Commercially available assays make use of a monoclonal anti-human EGFR and specifically detects the EGFR protein in EGFR-expressing cells. The binding of the primary monoclonal antibody (anti-EGFR) is detected by a secondary antibody molecules (directed to the anti-EGFR antibody) linked to horseradish peroxidase. The enzymatic conversion of the subsequently added chromogen results in formation of a visible reaction product at the antigen site. Results are interpreted using a light microscope. A tumor cell is EGFR-positive, if it possesses any staining above background. A tumor with no staining above background in any tumor cell is reported as an EGFR-negative tumor.

Inhibition of EGFR and EGFR Inhibitors

Many therapeutic approaches are aimed at the EGFR, namely which reduce or block EGFR. An EGFR inhibitor is an active agent which selectively decreases or blocks the activity, the bioavailability and/or subcellular localisation (membrane versus cytoplasmic or nuclear localization) and biological effects of EGFR. Preferably, an EGFR inhibitor is an active agent which selectively decreases or blocks one or more of the following: blockage of ligand binding, inhibition of tyrosine kinase activity, inhibition of downstream signaling, inhibition of induced cell responses (i.e. proliferation, migration, survival), reduction of EGFR half-life, inhibition of EGFR internalization and recycling, inhibition of translocation into the nucleus. For testing, if EGFR is inhibited diverse assays may be carried out. Such tests involve testing the blockage of ligand binding, inhibition of tyrosine kinase activity, inhibition of induced cell response (proliferation, survival, migration), inhibition of EGFR internalization, inhibition of translocation into the nucleus.

Said EGFR inhibitor may be a monoclonal or polyclonal antibody specifically binding to EGFR, an anti-sense nucleic acid or chemical analogue thereof specifically hybridizing to EGFR mRNA or a chemical compound specifically inhibiting EGFR activation.

According to the present invention the MT4-MMP inhibitor is administrated simultaneously, sequentially or separately with an EGFR inhibitor. Said EGFR inhibitor preferably is selected from the group consisting of cetuximab, panitumumab, zalutumumab, nimotuzumab, erlotinib, gefitinib, lapatinib, neratinib, canertinib, vandetanib, afatinib, TAK-285 (dual HER2 and EGFR inhibitor), ARRY334543 (dual HER2 and EGFR inhibitor), Dacomitinib (pan-ErbB inhibitor), OSI-420 (Desmethyl Erlotinib) (EGFR inhibitor), AZD8931 (EGFR, HER2 and HER3 inhibitor), AEE788 (NVP-AEE788) (EGFR, HER2 and VEGFR 1/2 inhibitor), Pelitinib (EKB-569) (pan-ErbB inhibitor), CUDC-101 (EGFR, HER2 and HDAC inhibitor), XL647 (dual HER2 and EGFR inhibitor), BMS-599626 (AC480) (dual HER2 and EGFR inhibitor), PKC412 (EGFR, PKC, cyclic AMP-dependent protein kinase and S6 kinase inhibitor), BIBX1382 (EGFR inhibitor) and AP26113 (ALK and EGFR inhibitor). The inhibitors cetuximab, panitumumab, zalutumumab, nimotuzumab are monoclonal antibodies. Erlotinib, gefitinib, lapatinib, neratinib, canertinib, vandetanib and afatinib are tyrosine kinase inhibitors.

Cetuximab and panitumumab are examples of monoclonal antibody inhibitors. However the former is of the IgG1 type, the latter of the IgG2 type. It should be noted that consequences on antibody-dependent cellular cytotoxicity can be quite different. Other monoclonals in clinical development are zalutumumab, nimotuzumab, and matuzumab. The monoclonal antibodies block the extracellular ligand binding domain. With the binding site blocked, signal molecules can no longer attach there and activate the tyrosine kinase. Another method is using small molecules to inhibit the EGFR tyrosine kinase, which is on the cytoplasmic side of the receptor. Without kinase activity, EGFR is unable to activate itself, which is a prerequisite for binding of downstream adaptor proteins. Ostensibly by halting the signaling cascade in cells that rely on this pathway for growth, tumor proliferation and migration is diminished. Gefitinib, erlotinib, and lapatinib (dual EGFR and ERBB2 inhibitor) are examples of small molecule kinase inhibitors. There are several quantitative methods available that use protein phosphorylation detection to identify EGFR family inhibitors.

Cetuximab (Erbitux) (IgG1) was developed for the treatment of patients with epidermal growth factor receptor (EGFR)-expressing, KRAS wild-type metastatic colorectal cancer (mCRC), in combination with chemotherapy, and as a single agent in patients who have failed oxaliplatin- and irinotecan-based therapy and who are intolerant to irinotecan.

Cetuximab is also used for the treatment of patients with squamous cell carcinoma of the head and neck in combination with platinum-based chemotherapy for the 1st line treatment of recurrent and/or metastatic disease and in combination with radiation therapy for locally advanced disease.

Panitumumab (Vectibix) (IgG2) is used for the treatment of refractory EGFR-expressing metastatic colorectal cancer in patients with non-mutated (wild-type) KRAS.

Zalutumumab and nimotuzumab are currently under clinical trials.

Erlotinib (Tarceva) is used for the treatment of locally advanced or metastatic non-small cell lung cancer that has failed at least one prior chemotherapy regimen. Further, erlotinib is used in combination with gemcitabine for treatment of locally advanced, unresectable, or metastatic pancreatic cancer.

Gefitinib (Iressa) is used for the treatment of patients with advanced NSCLC (lung cancers).

Lapatinib (Tykerb) is an EGFR and HER2 inhibitor and is used for the treatment of patients with advanced or metastatic breast cancer whose tumors overexpress HER2 (ErbB2).

Neratinib, canertinib and afatinib are currently under clinical trials.

Effects of MT4-MMP on EGFR

The implication of the GPI-anchored MT4-MMP in breast cancer progression was previously supported by clinical data and experimental observations. Until now, MT4-MMP functions have been ascribed to its capacity to regulate tumor vascularization. In the present application a novel mechanism is described by which MT4-MMP promotes breast cancer cell proliferation in vivo and in vitro by promoting an outside-in signaling through the EGFR pathway. The data presented in the present invention highlight a central role for MT4-MMP in breast cancer cell proliferation and identify this enzyme as a co-activator of EGFR increasing tumor cell sensitivity to EGFR ligands. This mitogenic effect of MT4-MMP on breast cancer cells is supported by data generated in vivo in xenografts and in vitro in complex 3D culture systems mimicking the in vivo situation.

The proliferative advantage conferred to tumors by MT4-MMP expression correlated with a strong inactivation of the tumor suppressor Rb protein that plays a pivotal role in the negative control of the cell cycle. The increase in Rb phosphorylation was associated with enhanced expression of cyclins D1, D3, E and CDK4 in MT4-MMP tumors. Rb hypo-phosphorylation represses gene transcription required for 01 to S phase transition, by binding to the promoter of targeted genes as a complex formed with E2F. Interestingly, E2F expression was increased in MT4-MMP tumors, supporting the implication of pRB pathway in MT4-MMP-mediated mitogenic effects in vivo. The inhibition of CDK4 in the 3D in vitro culture model abolished the proliferation of MT4-MMP expressing cells but not that of control cells. These data provide evidence for a novel oncogenic function of MT4-MMP by suppressing Rb activity, thereby promoting cancer cell proliferation.

Through a pharmacological approach, the present inventors identified tyrosine kinases as targets of MT4-MMP-mediated effect and more specifically EGFR as a potential molecular partner. Aberrant EGFR signaling is a major feature of breast cancers and it has been reported that EGFR stimulates cell proliferation through Rb signaling pathway. The present inventors found a significant increase in EGFR ligand (TGFα, EGF and amphiregulin) expression, at the mRNA levels, in MT4-MMP tumors and in 3D cultures. In contrast, the amounts of EGFR were not affected by MT4-MMP status. Notably, a 75 kDa phosphorylated form of EGFR was detected in higher amounts in MT4-MMP expressing tumors than in control tumors. In line with this finding, an intracellular EGFR fragment has been reported previously in breast cancer cell lines which result from a protease activity. Indeed, cytoplasmic localization of EGFR in human samples has been previously reported to be associated with tumor malignancy. Nuclear form of EGFR has been previously reported to regulate cell cycle through its association with transcription factors and to play a role in tumor aggressiveness and resistance to anti-EGFR treatment.

Evidence for an interaction between EGFR forms and MT4-MMP is provided in this invention by immunoprecipitation experiments where EGFR 175 kDa and an abundant 75 kDa fragment were found in MT4-MMP precipitates. Moreover, MT4-MMP was found in EGFR immunoprecipitates obtained with anti-EGFR antibody. In the presence of exogenous EGFR ligands, MT4-MMP promotes EGFR phosphorylation at Y1173 suggesting a role of MT4-MMP as a cofactor for EGFR activation by its specific ligands. The findings of the present inventors clearly established a novel functional link between MT4-MMP and EGFR and give new insight into how a GPI-anchored MMP contributes to EGFR signaling in breast cancers. Although metalloprotease-related enzyme such as ADAM17 and ADAM10 are classically viewed as sheddases of EGFR ligands, the present inventors surprisingly found a cross-talk between the receptor of EGF and a GPI-anchored MT-MMP (MT4-MMP).

A proliferative advantage attributed to cancer cells by membrane-associated MMP expression has been previously reported. Indeed, MT1-MMP overexpression in cancer cells promotes tumor cell proliferation in 3D collagen matrix and tumor growth in vivo. In addition, MT1-MMP expression in breast cancer confers protection against type I collagen-mediated apoptosis. In contrast to MT1-MMP, MT4-MMP endows cells with a proliferative advantage in a 3D basement membrane matrix, but not in a 3D collagen gel. In the studies according to the present invention cell proliferation was not affected by MT4-MMP expression when cells were cultured in 3D type I collagen matrix. Similar results were obtained when cells were first allowed to form spheroids in methyl cellulose and then embedded in type I collagen matrix. The failure of MT4-MMP to induce proliferation when cells are mixed in 3D type collagen matrix might be ascribed to its inability to cleave type I collagen in contrast to MT1-MMP, as reported previously. Alternatively, these observations combined with the absence of a mitogenic effect of MT4-MMP in 2D-cultures as reported previously suggest that MT4-MMP proliferating phenotype is dependent on the 3D conformation of cell aggregates induced by a basement membrane matrix. Culture conformation condition has emerged recently as a factor influencing the transduction of signals through TK. For instance, the culture of SKBR-3 breast cancer cells in 3D conditions stimulate HER2 activation through homodimerization and increased signaling through MAPK, whereas in 2D cultures, HER2 forms oligomers and instead signals through PI3K, as previously reported. One could thus speculate that the 3D matrix conformation influences cell-cell interactions and controls the interactions occurring between MT4-MMP and EGFR. The similar mitogenic effect of MT4-MMP observed in the present studies in complete Matrigel® as well as in growth factor-depleted Matrigel® demonstrates that this effect does not rely on the release of growth factor sequestered in the matrix.

MT-MMPs have long been viewed as regulators of cell migration and angiogenesis. While most important mechanisms described till now are focused on MT1-MMP and its role in migration, angiogenesis, vessel stability and tumor growth, a little attention has been given on the GPI-anchored MT-MMPs that include 2 enzymes MT4-MMP and MT6-MMP. In contrast to MT1-MMP knockout mice, MT4-MMP knockout mice develop normally without any severe phenotype. As previously shown no difference in angiogenesis is detected when Mt4-mmp−/− mice were subjected to aorta ring and corneal burn assays; however, when MT4-MMP is expressed in tumor cells, it induces a rapid tumor growth and metastasis to the lung. MT4-MMP expressing tumors have leaky vessels with reduced pericyte coverage. In line with this observation, it was also previously demonstrated that MT4-MMP induces in vivo an early angiogenic switch, at day 7-post tumor inoculation.

According to the present invention, a novel model of MT4-MMP contribution to cancer progression is proposed according to which the enzyme can promote tumor growth through indirect and direct effects on tumor cells. The indirect MT4-MMP tumor promoting effect relies on an early angiogenic switch detected in vivo as soon as day 7 after cell inoculation. In addition, MT4-MMP can directly affect cell proliferation by the transduction of mitogenic signals through EGFR activation. These two mechanisms of action are not exclusive and likely exert synergistic effects on tumor expansion. Altogether the data according to the present invention establish an unexpected link between MT4-MMP and EGFR pathway and highlight the importance of this poorly studied GPI-anchored MMP in cancer etiology.

Treatment Protocols

The method for treatment of cancerous diseases comprises administering to a patient an effective amount of the compound of the present invention.

The compounds of the invention may be administered singly or in combination with each other or other agents used for the therapy of cancer. Typically, the compounds of the present invention are administered in an amount of about 5 micrograms to 3,000 µg/kg per day, and more preferably about 20 to 1,500 µg/kg per day preferably once or twice daily. However, other amounts, including substantially lower or higher amounts, may also be administered. The compounds of the invention are administered to a human subject in need of treatment by oral, intravenous, intraperitoneal, intramuscular, transdermal, nasal, iontophoretic, subcutaneous, intratumoral, administration or by any other acceptable route of administration.

Different amounts of the compounds of the present invention may also be administered as seen suitable by a practitioner for specific cases. For this or any other application the compounds of this invention may be administered in an amount of about 10 to 3,750 µg/kg, and more preferably about 15 to 1,600 µg/kg. Any means of administration is suitable. The foregoing ranges are, however, suggestive, as the number of variables in regard to an individual treatment regime is large, and considerable excursions from these recommended values are expected.

Formulations and Pharmaceutical Compositions

The following description refers to pharmaceutical compositions which may contain one or more active agents of the present invention. MT4-MMP inhibitor and EGFR inhibitor for use in the treatment of cancer may be are administered simultaneously, sequentially or separately. Therefore, pharmaceutical compositions may comprise both inhibitors in one dosage form for simultaneously administration or in separate dosage forms for sequential or separate administration.

The compositions of the invention will be formulated for administration through ways known in the art and acceptable for administration to a mammalian subject, preferably a human. In some embodiments of the invention, the compositions of the invention can be administered by oral, intravenous, intraperitoneal, intramuscular, transdermal, nasal, iontophoretic, subcutaneous, intratumoral, administration or by any other acceptable route of administration. In further embodiments of the invention the compositions of the invention are administered "locoregionally", i.e., intravesically, intralesionally, and/or topically. In preferred embodiments of the invention, the compositions of the invention are administered systemically by injection, inhalation, suppository, transdermal delivery, etc. In further embodiments of the invention, the compositions are administered through catheters or other devices to allow access to a remote tissue of interest, such as an internal organ. The compositions of the invention can also be administered in depot type devices, implants, or encapsulated formulations to allow slow or sustained release of the compositions.

In order to administer therapeutic agents based on, or derived from, the present invention, it will be appreciated that suitable carriers, excipients, and other agents may be incorporated into the formulations to provide improved transfer, delivery, tolerance, and the like.

A multitude of appropriate formulations can be found in the formulary known to all pharmaceutical chemists: Remington's Pharmaceutical Sciences, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

Any of the foregoing formulations may be appropriate in treatments and therapies in accordance with the present invention, provided that the active agent in the formulation is not inactivated by the formulation and the formulation is physiologically compatible.

The quantities of active ingredient necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients. Animal testing of effective doses for treatment of particular disorders will provide further predictive indication of human dosage. Various considerations are described, for example, in *Goodman and Gilman's the Pharmacological Basis of Therapeutics,* 7th Edition (1985), MacMillan Publishing Company, New York, and *Remington's Pharmaceutical Sciences* 18*th Edition*, (1990) Mack Publishing Co, Easton Penn. Methods for administration are discussed therein, including oral, intravenous, intraperitoneal, intramuscular, transdermal, nasal, iontophoretic administration, and the like.

The compositions of the invention may be administered in a variety of unit dosage forms depending on the method of administration. For example, unit dosage forms suitable for oral administration include solid dosage forms such as powder, tablets, pills, capsules, and dragees, and liquid dosage forms, such as elixirs, syrups, and suspensions. The active ingredients may also be administered parenterally in sterile liquid dosage forms. Gelatin capsules contain the active ingredient and as inactive ingredients powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The compositions of the invention may be administered by use of solid compositions. For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more compositions of the invention, and more preferably at a concentration of 25%-75%.

For aerosol administration, the compositions of the invention are preferably supplied in finely divided form along with a surfactant and propellant. Typical percentages of compositions of the invention are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included, as desired, as with, e.g., lecithin for intranasal delivery.

The compositions of the invention can additionally be delivered in a depot-type system, an encapsulated form, or an implant by techniques well known in the art. Similarly, the compositions can be delivered via a pump to a tissue of interest.

The composition of the invention may also be provided in a kit as a slow-release composition such as a daily, weekly, monthly unit provided as a sponge, dermal patch, subcutaneous implant and the like in a wrapping or container. In this case, the patient may release a unit of the composition from the container and applies it as indicated in the kit instructions. The composition may then be replaced at the end of the specified period by a fresh unit, and so on.

The compound(s) of the present invention may be administered in a composition that also comprises one or more further drugs. The proportion of compounds of the present invention to the other drug(s) and carrier may be adjusted accordingly.

Antibodies

The invention also refers to the antibodies as an antibody directed to MT4-MMP will partially or completely reduce the activity of this protein. The present invention further provides compositions comprising antibodies that specifically bind to MT4-MMP. In a preferred embodiment the protein MT4-MMP is having the amino acid sequence SEQ ID NO: 1. The antibodies may be monoclonal antibodies, polyclonal antibodies, antibody fragments or any combination thereof. In particular, said antibody may be a common antibody (which is composed of two heavy protein chains and two light chains), Fab fragments of a common antibody, single-chain variable fragments or single-domain antibody (sdAb). The antibodies may be formulated with a pharmaceutically acceptable carrier. In a preferred embodiment the antibodies specifically recognize and bind to MT4-MMP having the amino acid sequence SEQ ID NO: 1. Further preferred the antibodies specifically recognize an epitope (a stretch of 5 or more consecutive amino acid residues within the amino acid sequence shown in SEQ ID NO: 1).

The term "antibody," as used herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, including an antibody fragment. "Antibody" and "immunoglobulin" are used synonymously herein. An antibody fragment is a portion of an antibody such as F(ab')2, F(ab)2, Fab', Fab, Fv, scFv, Nanobodies and the like. Nanobodies (or single-domain antibodies (sdAb)) are antibody-derived therapeutic proteins that contain the unique structural and functional properties of naturally-occurring heavy-chain antibodies. The Nanobody technology was originally developed following the discovery that camelidae (camels and lamas) possess fully functional antibodies that lack light chains. These heavy-chain antibodies contain a single variable domain (VHH) and two constant domains ($C_H2$ and $C_H3$). Importantly, the cloned and isolated VHH domain is a perfectly stable polypeptide harbouring the full antigen-binding capacity of the original heavy-chain antibody. The antibodies could be obtained using immunization in human and animals (mouse, rabbit, camel, lama, hen, goat).

Regardless of structure, an antibody fragment binds with the same antigen that is recognized by the full-length antibody, and, in the context of the present invention. Methods of making and screening antibody fragments are well-known in the art.

An anti-MT4-MMP antibody according to the present invention may be prepared by a number of different methods. For example, the antibodies may be obtained from subjects administered the recombinant polypeptide according to the present invention. In some embodiments, the antibodies may be made by recombinant methods. Techniques for making recombinant monoclonal antibodies are well-known in the art. Recombinant polyclonal antibodies can be produced by methods analogous to those described in U.S. Patent Application 2002/0009453, using the recombinant polypeptide according to the present invention as the immunogen(s). Said antibody obtained in accordance with the invention may be a murine, human or humanized antibody. A humanized antibody is a recombinant protein in which the CDRs of an antibody from one species; e.g., a rodent, rabbit, dog, goat, horse, camel, lama or chicken antibody (or any other suitable animal antibody), are transferred from the heavy and light variable chains of the rodent antibody into human heavy and light variable domains. The constant domains of the antibody molecule are derived from those of a human antibody. Methods for making humanized antibodies are well known in the art. More recently, it was reported that it is possible to generate hybridomas directly from human B-cells. Consequently, the recombinant polypeptide according to the present invention could be used to stimulate proliferation of human B-cell before to proceed to the generation of hybridomas.

The above-described antibodies can be obtained by conventional methods. For example, the recombinant polypeptide according to the present invention can be administered to a subject and the resulting IgGs can be purified from plasma harvested from the subject by standard methodology.
Antibody Compositions The invention also refers to the preparation of antibodies and antibody compositions suitable for administration, such as compositions comprising an antibody and a pharmaceutically acceptable carrier. The antibody compositions may be formulated for any route of administration, including intravenous, intramuscular, subcutaneous and percutaneous, by methods that are known in the art. In one embodiment, the antibody composition provides a therapeutically effective amount of antibody, i.e., an amount sufficient to achieve a therapeutically beneficial effect.

In one embodiment, the antibody composition is an IVIG composition. As used herein, "IVIG" refers to an immunoglobulin composition suitable for intravenous administration. IVIG compositions may contain, in addition to immunoglobulin, a pharmaceutically acceptable carrier. The IVIG compositions may be "specific IVIG," meaning that the IVIG contains immunoglobulins that specifically bind to the antigen(s) represented by the recombinant polypeptide according to the present invention.

In one embodiment, the specific IVIG composition comprises both an antibody that specifically binds to MT4-MMP and an antibody that specifically binds to another antigen (and that optionally neutralizes this other antigen). The antibodies and antigens may be any of those previously described. For example, the other antigen may be such as EGFR.

Methods of Making IVIG Compositions

The present invention also provides methods of making IVIG compositions, including specific IVIG compositions. An IVIG composition is prepared by administering the recombinant polypeptide according to the present invention to a subject, then harvesting plasma from the subject and purifying immunoglobulin from the plasma.

The subject that is challenged, or administered, the antigen(s), such as the recombinant polypeptide according to the present invention, may be a human or may be another animal, such as a mouse, a rabbit, a rat, a chicken, a horse, a dog, a non-human primate, or any other suitable animal. Antibodies that specifically bind the antigen(s) may be obtained from the animal's plasma by conventional plasma-fractionation methodology.

Antibodies raised against peptides of the invention may also be used to detect the presence of those peptides in various assays. Preferred assays are enzyme immunoassays or radioimmunoassay. The antibodies could be also used to develop affinity chromatography to purify specific proteins or macromolecules.

Treatment of Cancer with Antibody Compositions

The present invention also refers to a method of treating cancer by administering the above-described antibody compositions, such as the above-described IVIG compositions, to a subject in need thereof. A target patient population for the treatment of cancer includes mammals, such as humans, who suffer of cancer.

In accordance with one embodiment, the invention provides a method for treating cancer using compositions comprising an antibody or antibodies directed to MT4-MMP according to the present invention, and a pharmaceutically acceptable carrier. In yet another embodiment, the antibodies are monoclonal antibodies.

A therapeutically effective amount of the antibody compositions can be determined by methods that are routine in the art. Skilled artisans will recognize that the amount may vary according to the particular antibodies within the composition, the concentration of antibodies in the composition, the frequency of administration, the severity of disease to be treated, and subject details, such as age, weight and immune condition. In some embodiments, the dosage will be at least 50 mg IVIG composition per kilogram of body weight (mg/kg), including at least 100 mg/kg, at least 150 mg/kg, at least 200 mg/kg, at least 250 mg/kg, at least 500 mg/kg, at least 750 mg/kg and at least 1000 mg/kg. Dosages for monoclonal antibody compositions typically may be lower, such as 1/10 of the dosage of an IVIG composition, such as at least about 5 mg/kg, at least about 10 mg/kg, at least about 15 mg/kg, at least about 20 mg/kg, or at least about 25 mg/kg. The route of administration may be any of those appropriate for a passive vaccine. Thus, intravenous, subcutaneous, intramuscular, intraperitoneal, intratumorally and other routes of administration are envisioned. As noted above, a therapeutically effective amount of antibody is an amount sufficient to achieve a therapeutically beneficial effect. A protective antibody composition may decrease tumor size and prevent spreading and metastasis.

The antibody composition may be administered in conjunction with an anti-cancer agent. The anti-cancer agents may be combined prior to administration, or administered concurrently or sequentially with the IVIG composition.

Antisense Oligonucleotides

The MT4-MMP inhibitor may be an antisense oligonucleotide being at least 8 nucleotides in length, preferably 8 to 2410, further preferred 8 to 500, still further preferred 8 to 200, even further preferred 8 to 80 nucleotides and particularly preferred 12 to 50, 13 to 40 and 15 to 30 nucleotides in length, which specifically hybridises with a nucleic acid molecule encoding MT4-MMP, or which specifically hybridises a nucleic acid having the nucleotide sequence shown in SEQ ID NO: 2, and is capable of inhibiting MT4-MMP expression.

In one embodiment the antisense oligonucleotide is 100% complementary to the nucleic acid molecule encoding MT4-MMP.

The relationship between an antisense compound such as an oligonucleotide and its reverse complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent.

In the present invention, the targets are nucleic acids encoding MT4-MMP; in other words, a gene encoding MT4-MMP, or mRNA expressed from the MT4-MMP gene. mRNA which encodes MT4-MMP is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formyl-methionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding MT4-MMP, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal role of the target molecule to cause a loss of function or activity, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include any vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The locations on the target nucleic acid to which the preferred antisense compounds hybridize are hereinbelow referred to as "target segments." As used herein the term "target segment" is defined as at least an 8-nucleotide portion of a target region to which an active antisense compound is targeted. While not wishing to be bound by theory, it is presently believed that these target segments represent portions of the target nucleic acid which are accessible for hybridization.

While the specific sequences of certain target segments are set forth herein, one of skill in the art will recognize that these serve to illustrate and describe particular embodiments within the scope of the present invention. Additional target segments may be identified by one having ordinary skill.

Target segments 8-80 nucleotides in length comprising a stretch of at least eight consecutive nucleotides selected from within the illustrative preferred target segments are considered to be suitable for targeting as well.

Target segments can include DNA or RNA sequences that comprise at least the 8 consecutive nucleotides from the 5'-terminus of one of the illustrative target segments (the remaining nucleotides being a consecutive stretch of the same DNA or RNA beginning immediately upstream of the 5'-terminus of the target segment and continuing until the DNA or RNA contains about 8 to about 80 nucleotides). Similarly target segments are represented by DNA or RNA sequences that comprise at least the 8 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 8 to about 80 nucleotides). It is also understood that antisense target segments may be represented by DNA or RNA sequences that comprise at least 8 consecutive nucleotides from an internal portion of the sequence of an illustrative preferred target segment, and may extend in either or both directions until the oligonucleotide contains about 8 to about 80 nucleotides.

One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The overall effect of interference with mRNA function is decrease of the expression of MT4-MMP. This decrease can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

As used herein the term "oligomeric compound" is defined as a polymeric compound substantially comprising nucleic acid based monomer subunits. Oligomeric compounds include oligonucleotides and their analogs, mimics or mimetics.

Oligomer and Monomer Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside linkage or in conjunction with the sugar ring the backbone of the oligonucleotide. The normal internucleoside linkage that makes up the backbone of RNA and DNA is a 3' to 5' phosphodiester linkage.

Modified Internucleoside Linkages

Specific examples of preferred antisense oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Certain preferred oligomeric compounds of the invention can have one or more modified internucleoside linkages. A preferred phosphorus containing modified internucleoside linkage is the phosphorothioate internucleoside linkage.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage.

Oligonucleotide Mimetics

Another group of compounds of the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone.

The nucleobases are retained and are bound directly or indirectly to aza nitrogen atoms of the amide portion of the backbone.

Modified Nucleobases/Naturally Occurring Nucleobases

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deazaadenine, 7-deazaguanosine, 2-aminopyridine and 2-pyridone.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides. These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini.

In the case of antisense, effective inhibition of the mRNA requires that the antisense DNA have a very high binding affinity with the mRNA. Otherwise the desired interaction between the synthetic oligonucleotide strand and target mRNA strand will occur infrequently, resulting in decreased efficacy.

Antisense Compositions and Formulations

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

Pharmaceutical Compositions and Routes of Administration

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

In some embodiments, an oligonucleotide may be administered to a subject via an oral route of administration. In some embodiments, non-parenteral (e.g. oral) oligonucleotide formulations according to the present invention result in enhanced bioavailability of the oligonucleotide. In this context, the term "bioavailability" refers to a measurement of that portion of an administered drug which reaches the circulatory system (e.g. blood, especially blood plasma) when a particular mode of administration is used to deliver the drug. Enhanced bioavailability refers to a particular mode of administration's ability to deliver oligonucleotide to the peripheral blood plasma of a subject relative to another mode of administration.

Oligonucleotide compositions of the present invention may be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. A common requirement for these modes of administration is absorption over some portion or all of the alimentary tract and a need for efficient mucosal penetration of the oligonucleotides or mimetics thereof so administered.

A "pharmaceutical carrier" or "excipient" may be a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a an oligonucleotide and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB); and wetting agents (e.g., sodium lauryl sulphate, etc.).

The following examples illustrate the present invention and are not intended to limit the same.

EXAMPLES

Description of Materials and Methods

Example 1: Cell Culture and Plasmids

Human breast cancer MDA-MB-231, BT49 and A431 and COS-1 monkey epithelial cells were purchased from American Type Culture Collection (ATCC). Cells were grown in Dulbecco's Modified Eagle's Medium (DMEM) supplemented with 10% fetal bovine serum (FBS), L-Glutamine (2 mM), penicillin (100 U/ml) and streptomycin (100 µg/ml) at 37° C. in a 5% $CO_2$ humid atmosphere. All culture reagents were purchased from Gibco-Life Technologies (Invitrogen, Paisley, UK). Parental MDA-MB-231 cells were stably transfected by electroporation with empty pcDNA3-neo vector containing neomycin resistance gene (control plasmid, CTR) or with the same plasmid carrying the full-length active (MT4) human MT4-MMP cDNA designed as previously described (Chabottaux et al., *Cancer Res* 66, 5165-5172 (2006); Host et al. *Int J Cancer, doi:* 10.1002/ijc.27436 (2012)). Stable transfectants were cultured in medium containing 500 µg/ml of G418 (Life Technologies). In some assays, cells were treated with 10 ng/ml recombinant pro-TGFα (Cell Signaling Beverly, Mass., USA) or 20 ng/ml recombinant EGF (Sigma, St. Louis, Mo., USA). COS-1 cells were transiently transfected with a plasmid containing a FLAG-tag and carrying or not MT4-MMP cDNA (MT4-FLAG). Transient transfections were performed for 48 h using Xtream® gene transfection reagent and according to the manufacturer's recommendations (Roche, Mannheim, Germany). FLAG peptide sequence (EQKLISEEDL (SEQ ID NO: 3)) was inserted in the hinge region of MT4-MMP using quick change site directed mutagenesis kit (Stratagene, La Jolla, Calif.) and primers containing MT4-MMP hinge region and FLAG nucleotide sequence (underlined nucleotides), as follows: 5'-GCC-CCC-AGA-CTA-CAA-GGA-TGA-CGA-CGA-TAA-GAA-ACC G-GTC-CAG-CGC (forward) (SEQ ID NO: 4) and 5'-GCG-CTG-GAC-CGG-TTC-TTA-TCG-TCG-TCA-TCC-TTG-TAG-TCT-GGG-GGC (reverse) (SEQ ID NO: 5). The resulted PCR fragment was sequenced and inserted in the pcDNAzeo vector for cell transfection.

Example 2: In Vivo Tumorigenicity

Subconfluent MDA-MB-231 cells were trypsinized, resuspended in serum-free medium ($5 \times 10^6$ cells/ml) and mixed with an equal volume of cold Matrigel® according to previous report (26). Cell suspension (106 cells/400 µl) was injected s.c. into RAG-1 immunodeficient mice in both flanks (n=6).

Tumor growth was assessed by measuring the length and width of tumors every 3 to 4 days. Tumor volumes were estimated as previously described (length×width$^2$×0.4).

Example 3: RNA Extraction and Semi Quantitative RT-PCR Analysis

Total RNA was extracted from tumor samples or cell cultures using the Trizol reagent (Invitrogen) according to manufacturer's recommendations. RT-PCR was done on 10 ng RNA using specific primers (Eurogentec, Seraing, Belgium) and run in cycles of amplification for 15 seconds at 94° C., 20 seconds at 68° C., and 10 seconds at 72° C. PCR products were quantified by fluorimetric scanning (LAS-4000, Fujifilm, Wavre, Belgium). Quantification was performed by normalization of the values obtained for 28S rRNA amplification. The nucleotide sequences of the primers used were:

```
cyclin c:
                                    (SEQ ID NO: 6)
5'-GGACATGGGCCAAGAAGACATGTT-3'      (forward)
and (SEQ ID NO: 7)
5'-CTCCTTCACTGTTTGGAGGTGGTT-3'      (reverse);

cdc25a:
                                    (SEQ ID NO: 8)
5'-GCAACCACTGGAGGTGAAGAACAA-3'      (forward)
and (SEQ ID NO: 9)
5'-CTCATCTGGGTCGATGAGCTGAAA-3'      (reverse);

TGF alpha:
                                    (SEQ ID NO: 10)
5'-CCTGTTCGCTCTGGGTATTGTGTT-3'      (forward)
and (SEQ ID NO: 11)
5'-CTTGTCCTCCTGCACCAAAAACCT-3'      (reverse);

E2F1:
                                    (SEQ ID NO: 12)
5'-CGTGGACTCTTCGGAGAACTTTCA-3'      (forward)
and E2F1
                                    (SEQ ID NO: 13)
5'-ATGATGGTGGTGGTGACACTATGG-3'      (reverse);

EGFR:
                                    (SEQ ID NO: 14)
5'-CGCTCCCTCAAGGAGATAAGTGAT-3'      (forward)
and (SEQ ID NO: 15)
5'-CTCAGAGTTCTCCACAAACTCCCT-3'      (reverse);

EGF:
                                    (SEQ ID NO: 16)
5'-CCCTCATCACTGGTTGTGGTTCAT-3'      (forward)
and
```

-continued

```
                               (SEQ ID NO: 17)
5'-CCACAGGAGCACAGTCATCTTGAT-3' (reverse);

Amphiregulin:
                               (SEQ ID NO: 18)
5'-GGAGCCGACTATGACTACTCAGAA-3' (forward)
and (SEQ ID NO: 19)
5'-CATGTTACTGCTTCCAGGTGCTCT-3' (reverse).
```

Example 4: Preparation of Protein Cell Extracts and Immunoblot Analysis

Portions of tumor tissue frozen in liquid nitrogen were homogenized in 800 µl of lysis buffer (Cell Signaling) containing protease inhibitors and phosphatase inhibitors (Roche), using a MagnaLyser® (Roche).

Tissue lysates were centrifuged at 12,000×g for 10 min to remove insoluble debris and protein concentration in the supernatant was measured by using the DC protein Assay Kit (Bio-Rad Laboratories, Hercules, Calif., USA). Samples (40 µg of total protein extracts) were separated under reducing conditions on 8.5 to 15 polyacrylamide gels (depending on the molecular weight) and transferred onto polyvinylidene difluoride membranes (NEN, Boston, Mass., USA). Membranes were saturated for 2 hours with casein (1%, w/v) in PBS-Tween-20 (0.1%, v/v). Antigenic bands were detected by exposing the membranes to human primary antibodies targeting the following proteins: p-Rb [Ser807-811], p-Rb [Ser780], p-Rb [Ser795], total Rb (4H1), cyclin D1 (DCS6), Cyclin D3 (DCS22), CDK4 (DCS156), CDK6 (DCS83), p21 Waf1/Cip1 (DCS60), P27 Kip1, P15INK4b, total EGFR, p-EGFR [Tyr1173] (53A5) and pro-TGFα (Cell Signaling Technology, Beverly, Mass., USA), p-EGFR [Tyr1173] and CDK2 (M2) antibodies (Santa Cruz, Calif., USA) or antibodies to Cyclin E (HE12) and Cyclin A (BD Biosciences, Franklin Lakes, N.J., USA) or antibody to pRb [T821] (Invitrogen). After washes, membranes were incubated with a secondary horseradish peroxydase (HRP)-conjugated goat anti-rabbit antibody (1:2000, DakoCytomation) or sheep anti-mouse antibody (1:1000, DakoCytomation). Immunocomplexes were visualized by chemiluminescence reaction on a luminescent image analyzer (LAS-4000; Fujifilm, Wavre, Belgium). For loading control, membranes were stripped and reincubated with anti β-actin antibody (Sigma-Aldrich). Intensity of bands was quantified using Quantity-One software (Bio-Rad Laboratories) and normalized with respect to the total form of the studied protein or to β-actin amounts.

Example 5: Co-Immunoprecipitation Assay

COS-1 cells were transfected with full length MT4-MMP cDNA containing a FLAG tag inserted in the hinge region. After 48 h, cells were lyzed in lysis buffer (Cell Signaling) containing Protease Inhibitor Cocktail (complete, Roche) and Phosphatase Inhibitor Cocktail (PhosSTOP, Roche). Cell debris were removed by spinning at 13,000×g and MT4-MMP was immunoprecipitated from the lysate (200 µg) using 2 µg of a mouse monoclonal anti-Flag antibody (cloneM2, Sigma) and 40 µl of 50% slurry protein G coupled to dynabeads (Invitrogen). The precipitate was subject to western blotting using a rabbit polyclonal anti-EGFR antibody (Cell Signaling Technology) and HRP-conjugated secondary antibody. For coimmunoprecipitation of EGFR with MT4-MMP, cell extracts (500 µg of proteins) were incubated with 3 µg of rabbit polyclonal EGFR antibody (clone, D38B1, Cell Signaling Technology) and protein G dynabeads (Invitrogen). The precipitate was subjected to western blotting with a mouse monoclonal anti-FLAG antibody and HRP-conjugated secondary antibody.

Example 6: Immunohistochemistry

Proliferating cells in tumors were visualized by co-immunostaining with an anti-human-Ki-67 mouse monoclonal antibody and an anti-human-vimentin mouse antibody (DakoCytomation, Glostrup, Danemark)(Host et al. *Int J Cancer*, doi: 10.1002/ijc.27436 (2012)). For antigen retrieval, paraffin sections were autoclaved for 11 min at 126° C. in Target Retrieval Solution (Dako, S1699). Nonspecific binding was prevented by slide incubation in PBS/BSA 10% (Fraction V, Acros Organics, NJ) for 1 h. Ki-67 labeling was first performed by a 1 h incubation with anti-Ki-67 antibody (1:100) followed by saturation for 15 min and incubation for 30 min with the power vision poly-HRP anti-Mouse/Rabbit/Rat IgG kit (DVPB+110HRP, Immunologic, Duiven, The Nederlands). Slides revealed with Vector DAB (SK-4100, Vector Laboratories, Burlingame, Calif., USA) were then subjected to endogenous peroxydase blockade with 3% H202/H20 for 20 minutes. The anti-vimentin antibody (1:750, diluted in Tris-HCl/Normal Goat Serum) was next incubated overnight at 4° C. Slides were saturated for 15 min and incubated for 30 min with the power vision poly-AP anti-Mouse/Rabbit/Rat IgG kit (DVPB+110AP, Immunologic, Duiven, Nederlands) and colored with Permanent Red (K0640, Dako). For quantitative measurement of human Ki-67 related to human vimentin staining, an automatic computer-assisted image analysis was applied on 50 sections by using Application Software (3.2)(Host et al. *Int J Cancer*, doi: 10.1002/ijc.27436 (2012)). In RGB images, human vimentin appears in red and Ki-67 appears in brown colors. After separation of those components, red and brown images were binarized automatically and these binarized images were used to determine the colocalization of vimentin and ki-67 using a logical operator (AND). Results are expressed as colocalization area density.

Example 7: In Vitro 3-Dimensional Proliferation Assay and DNA Quantification

Matrigel® mixed with an equal volume of culture medium was coated onto 24-well plates (300 µl/plate). Cells (104) suspended in 250 µl of medium were mixed with the same volume of cold Matrigel® and seeded on the previously coated Matrigel® layer. In some assays, growth factor-free Matrigel® was used (BD, Bioscience). For signaling pathway inhibition in the 3D culture model, cells were incubated in Matrigel® matrix and 24 h later several inhibitors were added to the culture medium at the indicated concentrations:
SB203580, Genistein, U0126, Wortmannin, PP2, SP600125, AG538 (Sigma), PD0332991 (Axon Medchem, Groningen, The Nederlands), MDL-12, GF109203x, AG1478 (Calbiochem, Gibbstown, N.J.). The medium was changed every three days. After 7 days, cells were recovered from 3D cultures upon treatment with 500 µl of Dispase (BD, Bioscience) for 2 h at 37° C. After two washes in PBS, cell pellet was diluted in PBS (1 ml) and sonicated. Fluorimetric DNA titration was performed (Labarca, C., and Paigen, K., *Anal Biochem* 102, 344-352 (1980)) by measuring fluorescence in a Spectra Max Gemini Xs (Molecular Devices, Sunnyvale, Calif., USA) at 356 nm excitation and 460 nm emission.

Example 8: Inhibition of MT4-MMP Activity

Inhibition of enzymatic activity of MT4-MMP was quantified by measuring the cleavage of quenched fluorogenic peptide substrate by the recombinant catalytic domain of MT4-MMP (MT4-CAT) in the presence or absence of MT4-MMP blocking antibodies (scFV). MT4-CAT (4.5 µM) was pre-incubated with MT4-MMP blocking antibodies (14 nM) for 30 min at 4° C. in buffer containing (50 mM Tris-HCl (pH 7.4); 5 mM $CaCl_2$; $ZnCl_2$ 1 µM; 0.005%, Brij, 2% DMSO) before incubation with 30 µM of the fluorogenic substrate (pro-tumor necrosis factor-α converting enzyme (TACE) fluorogenic peptide substrate; Mca-(endo-1a-Dap (Dnp))-TNF-α (−5 to +6) amide (human), M-2255, Bachem AG, Switzerland). The inhibition of the activity was monitored by measuring the fluorescence with Luminescence spectrometer Spectra Max Gemini Xs (Molecular Devices, Sunnyvale, Calif., USA) at 320 nm excitation and 405 nm emission.

Example 9: Inhibition of MT4-MMP and/or EGFR Activity in a Cell Based Assay

Inhibition of MT4-MMP-dependent mitogenic effect of cancer cells was performed in 3D culture matrix. Matrigel® mixed with an equal volume of culture medium was coated onto 24-well plates (300 µl/plate). Cells ($10^4$) suspended in 250 µl of medium were mixed with the same volume of cold Matrigel® and seeded on the previously coated Matrigel® layer. For MT4-MMP or EGFR inhibition in the 3D culture model, cells were incubated in Matrigel® matrix and 24 h later MT4-MMP blocking antibodies (1-10 µg/ml) and/or EGFR inhibitor AG1478 (10 µM) (Calbiochem, Gibbstown, N.J.) were added to the culture medium. The medium was changed every three days. After 7 days, cells were recovered from 3D cultures upon treatment with 500 µl of Dispase (BD, Bioscience) for 2 h at 37° C. After two washes in PBS, cell pellet was diluted in PBS (1 ml) and sonicated. Fluorimetric DNA titration was performed by measuring fluorescence in a Spectra Max Gemini Xs (Molecular Devices, Sunnyvale, Calif., USA) at 356 nm excitation and 460 nm emission.

Example 10: Statistical Analysis

Differences between experimental groups were assessed using Mann-Whitney test. Ps<0.05 (*) were considered as significant. Statistical analyses were carried out using the Prism 4.0 and Prism 5.04 software, respectively, (GraphPad, San Diego, Calif.).

B. Description of Results

Example 11: MT4-MMP Promotes Tumor Cell Proliferation In Vivo

MDA-MB231 cells overexpressing MT4-MMP or control cells were sub-cutaneously injected into RAG-1 −/− mice as previously described (Chabottaux et al., Cancer Res, 66, 5165-5172 (2006); Host et al. Int J Cancer, doi: 10.1002/ijc.27436 (2012)). In accordance with previous reports, MT4-MMP expression resulted in increased tumor growth as reflected by the higher volumes of MT4-MMP expressing tumors than those of control tumors (FIG. 1A). To assess the proliferation index in vivo, tumors collected at day 21 were double-immunostained with human Ki-67 for proliferating cells and human vimentin for cancer cells (FIG. 1B). A computerized method based on image binarization was used to determine the density of proliferating cancer cells (Ki-67 and human vimentin positive). A significant enhancement of the proliferation index was observed in tumors expressing MT4-MMP at day 21 (FIG. 1C).

The phosphorylation status of Retinoblastoma protein (Rb) was next analyzed by western blot analysis in MT4-MMP tumors (FIG. 2). The inactivation of Rb upon hyperphosphorylation had been known to stimulate cell proliferation through the transcription of early genes required at the 01/S-phase transition. A significant increase in Rb phosphorylation at S807/811 was found in MT4-MMP expressing tumors, as compared to control tumors. Rb hyperphosphorylation at S807/811 appears specific for MT4-MMP expressing tumors, since other sites such as [S780], [S795] and [Thr 821] were not affected. Rb inactivation is known to be dependent on a concurrent increased expression or activation of the cyclin/CDK/E2F pathway or on downregulation of endogenous cyclin inhibitors. The immunoblot analysis of these putative regulators revealed a significant increase in the amounts of cyclin D1, cyclin D3, cylin E and CDK4 in MT4-MMP expressing tumors (FIG. 2, P<0.005). P27 protein cyclin/CDK complex inhibitor was also increased in MT4-MMP expressing tumors. This protein had been reported before to play a dual role in cell proliferation, either inhibiting cell proliferation or contributing to cylin/CDK complex assembly leading to cell proliferation. The other cell cycle regulators tested (cyclin A, cyclin D2, CDK2, CDK6, p15 and p21) were not affected by MT4-MMP expression. Finally, E2F protein, the central transcription factor downstream of Rb pathway was upregulated in MT4-MMP expressing tumors (FIG. 2). Altogether, these data demonstrated that MT4-MMP expression promoted breast cancer cell proliferation growth in vivo by controlling the Rb pathway.

Example 12: MT4-MMP Promotes Tumor Cell Proliferation In Vitro in a 3D Culture Model Using MDA-MB231 Cells When the proliferation rate of cells expressing or not MT4-MMP was assessed in vitro, no difference between these two cell types was seen in 2D-cultures on plastic dish (FIG. 3A). In accordance with a previous study (Chabottaux et al., Cancer Res 66, 5165-5172 (2006)), this result confirmed that MT4-MMP tumor promoting effect is dependent on the tumor microenvironment. In view of this observation cells were then embedded in a 3D matrix (Matrigel®) in order to mimic the in vivo situation. After 7 days, MDA-MB231 cells formed spheroids that were larger upon MT4-MMP expression (FIG. 3B). In these culture conditions, a significant increase in the proliferation rate of MT4-MMP expressing cells was evidenced by DNA quantification (FIG. 3B). Moreover, MT4-MMP promoted cell proliferation in Matrigel® depleted with growth factors (FIG. 3C), which is further supporting that MT4-MMP dependent mitogenic effect does not rely on the release of growth factors sequestered in Matrigel®.

Remarkably, cell proliferation induced by MT4-MMP production was inhibited upon treatment with CDK4 inhibitor PD0332991, confirming the key involvement of Rb pathway in vitro (FIG. 3D). Together, these observations highlighted the suitability of this 3D-culture system to investigate the outside-in signaling pathway activated by MT4-MMP and resulting in enhanced tumor cell proliferation.

Example 13: MT4-MMP Exerts its Mitogenic Effect Through EGFR Signaling

A pharmacological approach using small molecule inhibitors was next applied to provide further insights into the mechanisms underlying MT4-MMP action (FIG. 4). Neither the inhibitors of phosphatidylinositol 3-kinase pathway (wortmannin), adenylate cyclase pathway (MDL-12), protein kinase C pathway (GF109203x), MAPK/P38 kinase pathway (SB203580), nor MAPK/JNK pathway (SP600125) affected the MT4-MMP-mediated mitogenic effect (FIG. 4). In contrast, U0126, a MAPK/MEK1/2 inhibitor markedly inverted the proliferative phenotype in MT4-MMP expressing cells without affecting the proliferative rate in control cells (FIG. 4). Similarly, genistein, a broad spectrum tyrosine kinase inhibitor (TKIs), strongly inhibited MT4-MMP-mediated mitogenic effect (FIG. 4). These data pointed a functional interplay between MT4-MMP and TKs which results in downstream MAPKK activation and cell proliferation.

The implication of receptor or non-receptor tyrosine kinases was then explored by treating cells with specific inhibitors of Src (PP2 or 4-amino-5-(4-chlorophenyl)-7-(t-butyl)pyrazol[3,4-d]pyrimidine), Insulin-like Growth Factor Receptor (IGFR) (AG538) or EGFR (AG1478) (FIG. 4). No change in the proliferation rate of MT4-MMP expressing cells was observed with PP2 and IGFRI. However, the inhibition of EGFR signaling with AG1478 significantly reduced the MT4-MMP-mediated-mitogenic effect (FIG. 4). This data suggested that MT4-MMP effects are mediated through EGFR signaling.

Example 14: MT4-MMP is Associated in Protein Complexes with EGFR

Considering that EGFR and its ligands (EGF, TGFα, HB-EGF and amphiregulin) are commonly expressed by breast cancer cells, it was hypothesized that MT4-MMP might regulate EGFR ligand expression. RT-PCR analyses revealed that MT4-MMP expression led to enhanced mRNA levels of EGFR ligands (EGF, TGFα and amphiregulin) in vivo, in MT4-MMP expressing xenografts (FIG. 5A) and in vitro, in the 3D culture model (FIG. 5B). The EGFR phosphorylation status was then examined by western blot (FIG. 6). A band corresponding to full-length EGFR form (175 kDa) was similarly detected in tumors expressing or not MT4-MMP (FIG. 6). Interestingly, a 75 kDa form of EGFR phosphorylated at Y1173 was present at higher amount in MT4-MMP tumors than in control tumors. In sharp contrast, no 175 kDa phosphorylated EGFR form was detected in the two tumor types.

To determine whether MT4-MMP interacts with EGFR at the cell surface, COS-1 cells known to produce high amounts of EGFR receptor were transiently transfected with FLAG-tagged MT4-MMP (MT4-FLAG) and whole cell extracts were subjected to immunoprecipitation (IP) with an anti-FLAG antibody to pull down MT4-MMP before immunodetection with an anti-EGFR antibody (FIG. 7A). Both the full length EGFR form of 175 kDa and a species of 75 kDa were co-immunoprecipitated with MT4-MMP in cells transfected with MT4-MMP cDNA, whereas no signal was detected in cells transfected with the control vector. Furthermore, MT4-MMP co-immunoprecipitated with EGFR when IP was conducted with an anti-EGFR antibody prior immunodetection for FLAg-tag. Again, no MT4-MMP was detected in control cells (FIG. 7B). This reverse IP further supported the finding that MT4-MMP physically interacts with EGFR.

Example 15: MT4-MMP Promotes EGFR Activation in Response to Ligands

The data obtained by the previous experiments prompted the inventors to check whether MT4-MMP interaction with EGFR can affect the outside-in signaling in the presence of EGFR ligands. Therefore, COS-1 cells expressing or not MT4-MMP were stimulated in vitro with recombinant TGFα or EGF and EGFR phosphorylation status was assessed by western blot. Total EGFR levels were not affected by the addition of ligands. In contrast, EGFR phosphorylation was increased in response to TGFα. Notably, such an enhancement of EGFR phosphorylation was higher in MT4-MMP expressing cells than control cells (FIG. 7B). This finding provided a mechanistic evidence for enhanced TGFα and EGF signaling through EGFR by the membrane-associated MT4-MMP.

Example 16: Generation of Antibodies Against MT4-MMP by Phage Display Technology Antibodies against MT4-MMP were isolated from the naïve human scFv phage display libraries of VTT Biotechnology. The VTT naïve human scFv phage display libraries $V_H V_\kappa$ and $V_H V_\lambda$ (both containing approximately 108 clones) have been cloned from a pool of human lymphocytes of 50 healthy donors. Two different selection approaches were used for the development of MT4-MMP specific antibodies; selection using a recombinant MT4-MMP and selection using a cell-line over-expressing the MT4-MMP antigen. The recombinant MT4-MMP and the overexpression cell-line were provided by the University of Liege. In the first selection approach, recombinant MT4-MMP purified from inclusion bodies were used as the antigen. This selection strategy enriched antibodies recognising a linear epitope of the MT4-MMP. In the second selection approach a cell-line over-expressing the MT4-MMP was used. In this case antibodies binding native MT4-MMP was enriched.

1. Isolation of MT4-MMP Antibodies Using the Recombinant MT4-MMP as the Selection Antigen The DNAs of the naïve human scFv phage display libraries of VTT Biotechnology were transformed into *E. coli* XL1-Blue cells and phage display libraries (~$10^{12}$ pfu/ml) were produced.

The recombinant MT4-MMP protein was immobilised onto microtiter plate wells (1 µg of MT4-MMP/well). Background binding was analysed during the selection steps using BSA as the antigen, BSA is also used as the blocking agent in the scFv phage stocks. The scFv libraries, $V_H V_\kappa$ and $V_H V_\lambda$ scFv, were selected parallel. Four selection rounds were performed. The enrichment of the MT4-MMP specific scFv phages was analysed by tittering the amount of phages bound to MT4-MMP or BSA during the selection rounds. During the selection rounds, the stability of the scFv expression unit in the phagemid vector were analysed by restriction enzyme digestions. The stability of the scFv expression unit indicates that the selection procedure is functional.

The binding specificity of the isolated scFv phage stocks isolated from the selection rounds was analysed by an ELISA using MT4-MMP and BSA coating first. Individual soluble scFv-myc-pIII clones were cultivated on microtiter plates from the selection rounds showing highest enrichment against MT4-MMP (deduced from the ELISA result and the enrichment of MT4-MMP specific scFv phages during selection rounds). The binding specificity of the individual scFv clones was analysed by an ELISA using MT4-MMP and BSA coating. The nucleotide sequences of the scFv expression unit of 20 individual MT4-MMP specific clones were determined.

The binding characteristics of five (5) selected MT4-MMP specific scFv clones were analysed also by a Western blot approach (clones binding to a linear epitope) and by a FACS analysis of the MT4-MMP over-expressing cell-line (clones binding to native MT4-MMP). In these analyses either phage stocks or soluble myc-pIII fusion of the single scFv clones were used. Five (5) positive scFv clones were subcloned into a bacterial expression vector (pKKtac) enabling production of soluble scFv-myc-his fusions.

2. Isolation of MT4-MMP Antibodies Using a Cell-Line Over-Expressing the MT4-MMP as the Selection Antigen The DNAs of the naïve human scFv phage display libraries of VTT Biotechnology were transformed into *E. coli* XL1-Blue cells and phage display libraries (~$10^{11}$ pfu/ml) were produced. The scFv phage stocks were first pre-incubated with a "control" cell line to deplete binders against major cell surface antigens. After the pre-incubation step, the scFv phages that were not bound to the "control" cell-line were subjected to selection with the cell-line over-expressing the MT4-MMP. The scFv libraries $V_H V_\kappa$ and $V_H V_\lambda$ scFv were selected in parallel. Four selection rounds were performed. The enrichment of the MT4-MMP specific scFv phages was analysed by titering the amount of phages bound to MT4-MMP over expressing cell-line and to the "control" cell-line during the selection rounds. During the selection rounds, the stability of the scFv expression unit in the phagemid vector was analysed by restriction enzyme digestions. The stability of the scFv expression unit indicates that the selection procedure was functional. The binding specificity of the isolated scFv phage stocks isolated from the selection rounds was analysed by FACS using the MT4-MMP over-expressing and "control" cell lines. Individual scFv phage clones were cultivated on micotiter plates from the selection rounds showing highest enrichment against MT4-MMP over-expressing cell-line. The binding specificity of the individual scFv clones was analysed by Accuri C6 cytometry. The nucleotide sequences of the scFv expression unit of individual MT4-MMP specific clones were determined.

The binding characteristics of five selected MT4-MMP specific scFv clones were further analysed by a FACS analysis of the MT4-MMP over-expressing cell-line. In these analyses phage stocks of the scFv clones were used. Five positive scFv clones were subcloned into a bacterial expression vector (pKKtac) enabling production of soluble scFv-myc-his fusions.

As result, antibodies against MT4-MMP were isolated which specifically recognized and bound MT4-MMP polypeptide. Three scFV clones (K3F5, L3G2 and K4H7) were produced, purified and further characterized.

The binding capacity of three antibodies selected (K3F5, K4H7 and L3G2) was further studied by Western blotting. The antibodies tested recognized specifically active wild type recombinant MT4-MMP and MT4-MMP inactivated by a punctual mutation in its catalytic site (replacement of E249 by A). In sharp contrast, they do not recognize other recombinant MMPs such as MMP2, MT1-MMP (MMP14) or MT3-MMP (MMP16) (FIG. 14 A). These scFV antibodies were produced, purified and further characterized for their affinity for different concentrations of the recombinant MT4-MMP coated in 96 well plates (FIGS. 14 B and C). The antibody K4H7 clone displays the highest capacity to bind MT4-MMP (FIGS. 14 B and C). The three antibodies were able to inhibit the activity of the recombinant MT4-MMP toward a fluorescent substrate (FIG. 14 D).

In detail, antibody specificity was assessed by Western blot. Recombinant MT4-MMP (1 µg) was incubated with purified scFV clones (1 µg/ml) that contain a myc tag. Membranes were first incubated with a monoclonal mouse anti-myc antibody (clone 9E10, Sigma M5546) (1/1000) and then with HRP conjugated anti-mouse antibody (FIG. 14 A).

For determining antibody affinity recombinant MT4-CAT protein and BSA (background) was immobilized on 96 well-plates [0-3 µg of MT4-CAT in 15 mM Na-bicarbonate (pH 9.6)/well] for 18 h, at +4° C. Non-specific blockage was carried out by incubation of 3% (w/v) BSA/PBS, 0.01% (v/v) Tween-20, for 1 h, at +4° C. The detection of the bound antibody was carried out with 1:2000 diluted mouse anti-myc antibody (clone 9E10, Sigma M5546) incubated for 1 h, at room temperature, followed by 15 min incubation with HRP-conjugated anti-mouse antibody. After adding TMB substrate, the absorbance was measured at 450 nm Multi-skan FC (Thermo Scientific, Rockford, USA). The K4H7 clone displayed the highest affinity for recombinant MT4-MMP (FIG. 14 B).

The specificity of K4H7 antibody evaluated by ELISA. The specificity for MT4-MMP was determined by incubating the antibody with 3 µg of recombinant wild-type MT4-MMP (see column 3 of FIG. 14 C), inactive mutated form of MT4-MMP (E249A) (column 4) and other recombinant MMPs (5:MT1-MMP; 6: MT3-MMP; 7: MMP2). BSA (column 2) and the absence of protein (column 1: blank) were used as control. K4H7 clone binds specifically to MT4-MMP and its inactive form, but not to MT1-MMP, MT3-MMP and MMP 2 catalytic domains. Similar results were obtained with the clone K3F5, however the clone L3G2 was discarded because of its lack of specificity to MT4-MMP (data not shown).

Neutralizing capacity of antibodies. The enzymatic activity of the recombinant catalytic domain of MT4-MMP (MT4CAT) was monitored by the cleavage of quenched fluorogenic peptide substrate pro-tumor necrosis factor-α converting enzyme (TACE) (M-2255, BACHEM) and using Luminescence spectrometer (SPECTRA MAX; GIMINI). The substrate (Mca-(endo-1a-Dap(Dnp))-TNF-α (−5 to +6) amide (human), M-2255, Bachem AG, Switzerland)) used at 30 µM was incubated with MT4CAT 3 nM at 37° C. in a buffer containing 50 mM Tris (pH 7.4), 10 mM $CaCl_2$, 10 µM $ZnCl_2$, 0.005% Brij-35 and 2% DMSO. The cleavage of quenched fluorogenic peptide was monitored by measuring relative fluorescence units (RFU) during the incubation time (seconds) in the absence of inhibitor (MTCAT+No inhibitor) or in the presence of BB94 (20 µM) or of the scFV clones (14 nM). MT4-MMP enzymatic activity was inhibited completely with the three scFV clones (FIG. 14 D).

Sequence Analysis of K4H7 scFv Antibody

The sequences of K4H7 antibody was analysed. The heavy chain and light chain variable, the hypervariable regions CDR1, CDR2 and CDR3 as well as the framework regions 1 to 4 (FW1-4) are shown in FIG. 17. The VH (heavy chain) amino acid sequence (SEQ ID NO: 26) and VL (light chain) amino acid sequence (SEQ ID NO: 27) are indicated and linked together by a linker sequence (not shown. The complete scFv antibody as used in the examples has the amino acid sequence shown in SEQ ID NO: 28. The figure indicates the hypervariable regions (CDR1, CDR2 and CDR3) which are embedded within the scaffold FW1-FW4 (FW: framework) of heavy and light chain variable region. The hypervariable regions CDR1, CDR2 and CDR3 are also shown in the sequence listing (heavy chain: CDR1: SEQ ID NO: 20; CDR2: SEQ ID NO: 21; CDR3: SEQ ID NO: 22; light chain: CDR1: SEQ ID NO: 23; CDR2: SEQ ID NO: 24; CDR3: SEQ ID NO: 25).

Example 17: Inhibition of MT4-MMP by Broad Spectrum Inhibitor BB94

In order to interfere with MT4-MMP activity, a broad spectrum MMP inhibitor (BB94, Batimastat) was tested. Enzymatic activity of the recombinant catalytic domain of MT4-MMP (MT4CAT) was monitored by the cleavage of quenched fluorogenic peptide substrate pro-tumor necrosis factor-α converting enzyme (TACE) (M-2255, BACHEM) and using Luminescence spectrometer (SPECTRA MAX; GIMINI). The substrate (M-2255, Bachem AG, Switzerland) used at 30 µM was incubated with MT4CAT 3 nM at 37° C. in a buffer containing 50 mM Tris (pH 7.4), 10 mM $CaCl_2$, 10 µM $ZnCl_2$, 0.005% Brij-35 and 2% DMSO. The cleavage of quenched fluorogenic peptide was monitored in the absence of inhibitor or in the presence of 20 µM or 100 µM of the inhibitor BB94. The inhibition of MT4CAT activity with increasing concentrations of inhibitor showed a BB94 dose-dependent inhibition of MT4-MMP activity. The results are shown in FIG. 8. This assay demonstrates the capacity of BB94 to inhibit MT4-MMP activity.

Example 18: Combined Treatment with MT4-MMP Inhibitor and EGFR Inhibitor to Block Cancer Cell Proliferation This example was prepared to show whether the combined inhibition of MT4-MMP and EGFR signaling affect more efficiently cancer cell proliferation in 3D matrix than their single inhibition. With this aim, erlotinib, an EGFR inhibitor used in clinic was applied. The combined inhibition of BB94 and erlotinib was then evaluated in a cell-based assay using MDA-MB231 cells expressing MT4-MMP (FIG. 9). Cell proliferation was assessed after 7 days of incubation by DNA content quantification (µg/ml). Statistical analysis was performed using one-way ANOVA test with Prism 5.04 software (Graph Pad, San Diego, Calif.). Pvalue: * $p<0.05$; ** $p<0.01$. As outlined above, the expression of MT4-MMP led to increased tumor cell proliferation. Single doses of either BB94 (10 µM) or erlotinib (1 µM) partially inhibited the proliferation of cancer cells (FIG. 9). Notably, the combined treatment with BB94 and erlotinib abolished completely the MT4-MMP-mediated effect. These data demonstrated that MMP inhibitor treatment sensitized cancer cells to erlotinib, i.e. that the combined treatment of MT4-MMP inhibitor and EGFR inhibitor results in a stronger reduction of cell proliferation than the respective single treatment.

Example 19: Detection of MT4-MMP and EGFR Co-Localization in Breast Cancer Cells by Immunofluoresence and Confocal Microscopy The interaction between MT4-MMP and EGFR was demonstrated by immunoprecipitation experiments showing that MT4-MMP and EGFR are both present in the immune complexes (Example 5, FIG. 7). This example was established to show this interaction by confocal analysis showing a co-distribution of MT4-MMP and EGFR on breast cancer cells (MDA-MB231 cells) (FIG. 10). For this experiment MDA-MB231 cells expressing MT4-MMP were cultured on cover slips and stained with a mouse anti-FLAG and a rabbit anti-EGFR antibodies, followed by secondary anti-mouse Alexa Fluor-488 for FLAG (green color) and anti-rabbit Alexa Fluor-546 (red color) for EGFR. Image acquisition and analyses were performed with confocal microscopy using Olympus AV-100 microscope and FV-100 software. Co-localization of MT4-MMP and EGFR were shown as bright spots (arrows in merged image of FIG. 10) at the cell surface and intracellularly.

Example 20: MT4-MMP Promotes Tumor Cell Proliferation In Vitro in a 3D Culture Model Using BT549 Breast Carcinoma and A431 Epidermoid Carcinoma Cells MT4-MMP induction of cancer cell proliferation described in breast cancer MDA-MB231 cells (Example 12) was confirmed in two additional cell lines: BT549 breast carcinoma cells and A431 epidermoid carcinoma cells. Breast carcinoma BT549 cells and epidermoid A431 cells expressing MT4-MMP were generated by a stable transfection with MT4-MMP cDNA or control vector. Cell proliferation was assessed after 7 days of incubation in 3D Matrigel® in order to mimic the in vivo situation and DNA content quantification. MT4-MMP expression in the different cell lines (MT4) was associated with a significant increase in cell proliferation when compared to control cells (CTR) as evidenced by DNA quantification (FIG. 11 A, B). Statistical analysis was performed using Mann-Whitney test with Prism 5.04 software (GraphPad, San Diego, Calif.). P-value: * $p<0.05$ Example 21: Enhancement of EGFR Phosphorylation in the Presence of MT4-MMP In order to show that EGFR activation is enhanced by the expression of MT4-MMP the phosphorylation of EGFR was analyzed in 4 cell lines transfected with MT4-MMP cDNA or control vector and stimulated or not with recombinant pro-TGFα (10 ng/ml) or EGF (20 ng/ml) for 20 min. Then EGFR phosphorylation status was analyzed by western blot using antibodies raised against phosphor-EGFR and total EGFR (FIG. 12). Cell incubation with EGFR ligands induced EGFR phosphorylation in either cells expressing or not MT4-MMP. EGFR phosphorylation in response to ligands was shown to be significantly enhanced in all cells expressing MT4-MMP and EGFR: MDA-MB231, BT549, A431 and COS-1 cells. This data demonstrated a functional role of MT4-MMP in promoting EGFR activation and signaling.

Example 22: Expression of MT4-MMP and EGFR in Human Triple Negative Breast Cancer (TNBC)

The clinical relevance of a link between MT4-MMP and EGFR was investigated by immunohistochemistry analysis in breast cancer samples (FIG. 13). For this, immunohistochemical staining for MT4-MMP in normal breast tissues and TNBC sections were carried out. Human breast cancer samples and mammary reduction tissues were formalin (4%) fixed and paraffin embedded. Samples were provided by the bio-bank at CHU university of Liege, Belgium. For MT4-MMP immunohistochemistry, tumor sections (6 µm thick) were incubated in citrate buffer (DAKO S2031) for 1 h at 80° C. Endogenous peroxidases were subsequently blocked by 3% $H_2O_2/H_2O$ for 20 minutes, and nonspecific binding was prevented by incubation in PBS/10% bovine serum albumin (Fraction V, Acros Organics, NJ) for 1 hour. Slides were incubated over night at 4° C. with a rabbit polyclonal anti-human-MT4-MMP antibody (1/500) (Abcam®, AB39028). Slides were then incubated with a HRP-conjugated anti-rabbit secondary antibody (Envision System Labeled Polymer-HRP, DAKO, K4003) for 30 min at room temperature. For staining, 3-3' diaminobenzidine hydrochloride (DAKO, K3468) was incubated for 3 minutes. Slides were finally counterstained with hematoxylin and mounted with Eukitt medium for microscope observation. After antigen retrieval with EDTA buffer, EGFR immunohistochemistry was performed by incubating a rabbit monoclonal anti-EGFR antibody (5B7) (Venatana, 790-4347) for 32 min, and using an amplification kit (VENTA 760-080) in a series automated slide strainer (Discovery XT, ventata, Roche). Finally, sections were incubated with an universal secondary antibody (VENTANA, 760-4205) for 32 min and signal was detected with DAB Map detection kit (VENTANA, 760-124). Counterstaining was performed with hematoxylin II (VENTANA, 790-2208). Omission of the first antibody served as negative control.

The results showed that MT4-MMP expression is mainly localized in cancer cells in the TNBC but not in normal tissue. Similarly, EGFR expression is increased in the tumor compartment of TNBC. As a strong staining for MT4-MMP was observed in human TNBC samples, whereas the normal breast sections were negative and these tumors express high level of EGFR the results support strongly the functional role of MT4-MMP interaction with EGFR in cancer progression.

Example 23: Effect of Combined Treatment Using MT4-MMP Inhibitor and EGFR Inhibitor in a 3D Matrigel® Matrix Model The evidence of treatment efficacy by the combination of inhibition of MT4-MMP and EGFR in breast adenocarcinoma MDA-MB231 cells transfected with MT4-MMP cDNA was obtained by using the anti-MT4-MMP antibody (scFV clone K4H7) and erlotinib.

MDA-MB 231 cells expressing MT4-MMP were incubated in 3D Matrigel® matrix in the presence or absence (PBS/DMSO) of MT4-MMP blocking antibody (K4H7 clone) at the concentration of 20 µg/ml and erlotinib (Erlo) at 1 µM. Cell proliferation was assessed after 7 days of incubation by DNA content quantification (µg/ml). The experimental data showed the sensitization of cancer cells to EGFR inhibitor (erlotinib) treatment by using MT4-MMP blocking antibody.

The combined treatment of MT4-MMP blocking antibody and EGFR inhibitor resulted in a stronger reduction of cell proliferation than single treatments. While a single treatment with MT4-MMP blocking antibody at 20 µg/ml or erlotinib (1 µM) reduced cell proliferation in 3D culture matrix, a combination of both inhibitors had an even stronger inhibitory effect, demonstrating the efficacy of a combined treatment. The results are shown in FIG. 15.

Example 24: Analysis of Cancer Using MT4-MMP Antibody and EGFR Antibody in Immunohistochemistry Incubations with MT4-MMP antibody and EGFR antibody were performed on serial sections of breast cancer tissues.

Incubation of a Tissue Sample with MT4-MMP Antibody

Human breast cancer samples were formalin (4%) fixed and paraffin embedded. Tumor sections (6 µm thick) were incubated in citrate buffer (DAKO S2031) for 1 h at 80° C. Endogenous peroxidases were subsequently blocked by 3% $H_2O_2/H_2O$ for 20 minutes, and nonspecific binding was prevented by incubation in PBS/bovine serum albumin 10% (Fraction V, Acros Organics, NJ) for 1 hour. Slides were incubated over night at 4° C. with a rabbit polyclonal anti-human-MT4-MMP antibody (Abcam®, AB39028) at dilution of 1/500 in buffer (DAKO, S2022). Slides were then incubated with a HRP-conjugated anti-rabbit secondary antibody (Envision System Labeled Polymer-HRP, DAKO, K4003) for 30 min at room temperature. Coloring was done with 3-3' diaminobenzidine hydrochloride (DAKO, K3468) for 3 minutes. Slides were finally counterstained with hematoxylin and mounted with Eukitt medium for microscope observation.

Incubation of Tissue Sample with EGFR Antibody

Human breast cancer samples were formalin (4%) fixed and paraffin embedded. Tumor sections (6 µm thick) were incubated in EDTA buffer and incubated for 32 min with a rabbit monoclonal anti-EGFR antibody (5B7) (VENTANA®, 790-4347, Roche) ready to use and using a series automated slide strainer (Discovery XT, VENTANA®, Roche) and amplification kit (VENTANA® 760-080, Roche). Finally, sections were incubated with the universal secondary antibody (VENTANA®, 760-4205, Roche) for 32 min and signal detection with DAB Map detection kit (VENTANA®, 760-124, Roche). Counterstaining was performed with hematoxylin II (VENTANA®, 790-2208, Roche). Omission of the first antibody served as negative control.

Result and Interpretation

The results of the staining are shown in FIG. 16. Panels A and B refer to a first cancer tissue sample and panels C and D refer to a different cancer tissue sample. Panel A shows a high MT4-MMP production and panel B shows a cytoplasmic localization of EGFR. Panel C shows low MT4-MMP production and a membrane localization of EGFR.

Therefore, the analysis of MT4-MMP expression by IHC revealed its localisation either in cancer cells or in some stromal cells. MT4-MMP staining was mainly localized in the cytoplasm. EGFR was localized at the cell surface and/or intracellularly.

Therefore, it was concluded as follows: when MT4-MMP is highly expressed in cancer cells, EGFR can be found intracellularly with some labelling at the cell membrane (FIG. 16, panels A and B). However, when EGFR is mainly localized at the cell membrane, MT4-MMP is absent or present at low levels in cancer cells (FIG. 16, panels C and D).

The invention claimed is:

1. A monoclonal antibody which specifically binds to MT4-MMP, which is any one selected from the following antibodies:

(a) an antibody comprising
(i) a heavy chain variable domain which comprises a CDR1 region shown in SEQ ID NO: 20, a CDR2 region shown in SEQ ID NO: 21 and a CDR3 region shown in SEQ ID NO: 22, and
(ii) a light chain variable domain which comprises a CDR1 region shown in SEQ ID NO: 23, a CDR2 region shown in SEQ ID NO: 24 and a CDR3 region shown in SEQ ID NO: 25;

(b) an antibody having the amino acid sequence shown in SEQ ID NO: 26 as the amino acid sequence of a H chain variable region (VH), and having the amino acid sequence shown in SEQ ID NO: 27 as the amino acid sequence of a L chain variable region (VL); and (c) a scFv (single chain variable fragment) antibody comprising the amino acid sequence shown in SEQ ID NO: 28.

2. A pharmaceutical composition comprising a MT4-MMP inhibitor, wherein said MT4-MMP inhibitor is a monoclonal antibody which specifically binds to MT4-MMP, which is any one selected from the following antibodies:
- (a) an antibody comprising
  - (i) a heavy chain variable domain which comprises a CDR1 region shown in SEQ ID NO: 20, a CDR2 region shown in SEQ ID NO: 21 and a CDR3 region shown in SEQ ID NO: 22, and
  - (ii) a light chain variable domain which comprises a CDR1 region shown in SEQ ID NO: 23, a CDR2 region shown in SEQ ID NO: 24 and a CDR3 region shown in SEQ ID NO: 25;
- (b) an antibody having the amino acid sequence shown in SEQ ID NO: 26 as the amino acid sequence of a H chain variable region (VH), and having the amino acid sequence shown in SEQ ID NO: 27 as the amino acid sequence of a L chain variable region (VL); and
- (c) a scFv (single chain variable fragment) antibody comprising the amino acid sequence shown in SEQ ID NO: 28.

3. The pharmaceutical composition of claim 2, further comprising an EGFR inhibitor.

4. The pharmaceutical composition according to claim 3, characterized in that the MT4-MMP inhibitor and EGFR inhibitor comprised in said pharmaceutical composition are formulated separately to be used in the form of a kit where they are present together.

5. The pharmaceutical composition according to claim 3, characterized in that said pharmaceutical composition is formulated so that the MT4-MMP inhibitor and EGFR inhibitor are present in the same dosage form.

* * * * *